US 10,085,899 B2

(12) United States Patent
Komatsubara

(10) Patent No.: US 10,085,899 B2
(45) Date of Patent: Oct. 2, 2018

(54) DISPOSABLE DIAPER FOR PETS

(71) Applicant: UNI-CHARM CORPORATION, Ehime (JP)

(72) Inventor: Daisuke Komatsubara, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 347 days.

(21) Appl. No.: 14/651,666

(22) PCT Filed: Nov. 21, 2013

(86) PCT No.: PCT/JP2013/081454
§ 371 (c)(1),
(2) Date: Jun. 12, 2015

(87) PCT Pub. No.: WO2014/091901
PCT Pub. Date: Jun. 19, 2014

(65) Prior Publication Data
US 2015/0313776 A1 Nov. 5, 2015

(30) Foreign Application Priority Data

Dec. 13, 2012 (JP) .................................. 2012-272377

(51) Int. Cl.
*A61F 13/15* (2006.01)
*A61F 13/62* (2006.01)
(Continued)

(52) U.S. Cl.
CPC .............. *A61F 13/62* (2013.01); *A01K 23/00* (2013.01); *A61D 99/00* (2013.01);
(Continued)

(58) Field of Classification Search
CPC .......... A61F 13/49017; A61F 13/49413; A61F 13/53; A61F 13/5638; A61F 13/62;
(Continued)

(56) References Cited

U.S. PATENT DOCUMENTS 4,917,683 A    4/1990 Thompson
5,234,421 A    8/1993 Lowman
(Continued)

FOREIGN PATENT DOCUMENTS

CN    2281647 Y    5/1998
CN    200987318 Y    12/2007
(Continued)

OTHER PUBLICATIONS

Office Action in CN Application No. 201380065183.9, dated Jan. 18, 2017.
(Continued)

*Primary Examiner* — Bradley Philips
(74) *Attorney, Agent, or Firm* — Hauptman Ham, LLP

(57) ABSTRACT

A disposable diaper for pets, having: a rear-side waist area; a stomach-side waist area; a crotch area; a rear-side flap section; a stomach-side flap section; and a tail insertion opening. At least either the rear-side flap section or the stomach-side flap section have an identification area. A determination can be made that there is a problem with the state of the rear-side flap section, on the basis of visual inspection information about the identification area, said visual inspection being performed externally on the disposable diaper for pets.

16 Claims, 42 Drawing Sheets

(51) Int. Cl.
    *A61D 99/00*     (2006.01)
    *A01K 23/00*     (2006.01)
    *A61F 13/49*     (2006.01)
    *A61F 13/494*    (2006.01)
    *A61F 13/53*     (2006.01)
    *A61F 13/56*     (2006.01)

(52) U.S. Cl.
    CPC .. *A61F 13/49017* (2013.01); *A61F 13/49413* (2013.01); *A61F 13/53* (2013.01); *A61F 13/5638* (2013.01); *A61F 13/627* (2013.01); *A61F 2013/15186* (2013.01); *A61F 2013/49041* (2013.01)

(58) Field of Classification Search
    CPC .......... A61F 13/627; A61F 2013/15186; A61F 2013/49041
    See application file for complete search history.

(56) References Cited

U.S. PATENT DOCUMENTS

| | | | |
|---|---|---|---|
| 5,555,847 | A | 9/1996 | Kelly |
| 5,954,015 | A | 9/1999 | Ohta |
| 6,142,105 | A | 11/2000 | McKnight |
| 8,020,523 | B2 | 9/2011 | Ikegami et al. |
| 9,265,234 | B2 | 2/2016 | Komatsubara et al. |
| 9,332,731 | B2 | 5/2016 | Komatsubara et al. |
| 2005/0154367 | A1 | 7/2005 | Ikegami |
| 2006/0217678 | A1* | 9/2006 | Ikegami .................. A01K 23/00 604/386 |
| 2007/0142798 | A1* | 6/2007 | Goodlander ........ A61F 13/4902 604/361 |
| 2007/0149941 | A1* | 6/2007 | Ikegami .................. A01K 23/00 604/385.09 |
| 2009/0247980 | A1* | 10/2009 | Aiken ..................... A61F 13/84 604/385.01 |
| 2010/0229803 | A1 | 9/2010 | Meissner et al. |
| 2011/0192357 | A1 | 8/2011 | Pellegrini |
| 2011/0209675 | A1 | 9/2011 | Esperon |
| 2012/0226252 | A1 | 9/2012 | Yago et al. |
| 2012/0245550 | A1 | 9/2012 | Sakaguchi et al. |
| 2014/0076246 | A1 | 3/2014 | Komatsubara et al. |
| 2015/0196009 | A1 | 7/2015 | Komatsubara et al. |
| 2015/0272713 | A1 | 10/2015 | Komatsubara |
| 2015/0327517 | A1 | 11/2015 | Komatsubara |
| 2016/0008183 | A1 | 1/2016 | Komatsubara |

FOREIGN PATENT DOCUMENTS

| | | |
|---|---|---|
| CN | 102573738 A | 7/2012 |
| EP | 0692188 A1 | 1/1996 |
| EP | 1535509 A1 | 6/2005 |
| EP | 1709870 A1 | 10/2006 |
| JP | 10-75679 A | 3/1998 |
| JP | 11-73 A | 1/1999 |
| JP | 2003-102313 A | 4/2003 |
| JP | 2003-210062 A | 7/2003 |
| JP | 2003-220090 A | 8/2003 |
| JP | 2003-245024 A | 9/2003 |
| JP | 2004-159591 A | 6/2004 |
| JP | 3625203 B2 | 3/2005 |
| JP | 3112749 U | 8/2005 |
| JP | 2006-34872 A | 2/2006 |
| JP | 2006-271212 A | 10/2006 |
| JP | 2006-281545 A | 10/2006 |
| JP | 2007-135412 A | 6/2007 |
| JP | 2007-159420 A | 6/2007 |
| JP | 2007-228884 A | 9/2007 |
| JP | 2008-193920 A | 8/2008 |
| JP | 4445422 B2 | 4/2010 |
| JP | 4467512 B2 | 5/2010 |
| JP | 2012-110299 A | 6/2012 |
| JP | 2012-139128 A | 7/2012 |
| JP | 2012-183045 A | 9/2012 |
| JP | 2012-200206 A | 10/2012 |
| WO | 02/03901 A1 | 1/2002 |
| WO | WO 2012132886 A1 | 10/2012 |

OTHER PUBLICATIONS

Office Action in CN Application No. 201380065627.9, dated Jan. 24, 2017.
Office Action in CN Application No. 201380065637.2, dated Jan. 10, 2017.
Office Action in CN Application No. 201380065333.6, dated Jan. 22, 2017.
Office Action in CN Application No. 201380065247.5, dated Feb. 14, 2017.
Written Opinion of ISA in International Application No. PCT/JP2013/081454, dated Feb. 10, 2014.
Extended European Search Report in EP Application No. 13862655.1, dated Aug. 1, 2016.
Office Action in U.S. Appl. No. 14/651,227, dated Jun. 12, 2017.
Office Action in U.S. Appl. No. 14/651,228, dated Jun. 1, 2017.
Office Action in U.S. Appl. No. 14/651,229, dated Jun. 2, 2017.
Office Action in U.S. Appl. No. 14/651,230, dated Jun. 14, 2017.
Office Action in U.S. Appl. No. 14/651,231, dated May 30, 2017.
Office Action in U.S. Appl. No. 14/651,667, dated Jun. 13, 2017.
Office Action in U.S. Appl. No. 14/651,668, dated Jun. 13, 2017.
Notice of Allowance in U.S. Appl. No. 14/651,648, dated May 30, 2017.
Office Action in CN Patent Application No. 201380065150.4, dated Dec. 28, 2016.
Extended European Search Report corresponding to EP13861857.4, dated Jun. 22, 2016.
Extended European Search Report corresponding to EP13862081.0, dated Jun. 16, 2016.
Extended European Search Report in EP Application No. 13861809.5, dated Jul. 20, 2016.
Extended European Search Report in EP Application No. 13861991.1, dated Jul. 15, 2016.
Extended European Search Report in EP Application No. 13862127.1, dated Jul. 28, 2016.
Extended European Search Report in EP Application No. 13862288.1, dated Jul. 15, 2016.
Extended European Search Report in EP Application No. 13863278.1, dated Jul. 15, 2016.
International Preliminary Report on Patentability in PCT/JP2013/082890, dated Jun. 16, 2015.
International Search Report in PCT/JP2013/080346, dated Feb. 10, 2014.
International Search Report dated Feb. 10, 2014 in International Application No. PCT/JP2013/080347.
International Search Report dated Feb. 10, 2014 in International Application No. PCT/JP2013/080348.
International Search Report dated Feb. 10, 2014 in International Application No. PCT/JP2013/080951.
International Search Report dated Feb. 10, 2014 in International Application No. PCT/JP2013/080953.
International Search Report dated Feb. 10, 2014 in International Application No. PCT/JP2013/081453.
International Search Report dated Feb. 10, 2014 in International Application No. PCT/JP2013/081455.
International Search Report dated Feb. 10, 2014 in International Application No. PCT/JP2013/082890.
International Search Report dated Feb. 18, 2014 in International Application No. PCT/JP2013/082891.
Office Action (2nd) in CN Application No. CN201380065617.5, dated Oct. 21, 2016.
Office Action in CN Application No. 201380065150.4, dated Apr. 19, 2016.
Office Action in CN Application No. 201380065183.9, dated May 26, 2016.
Office Action in CN Application No. 201380065247.5, dated Apr. 25, 2016.

(56) References Cited

OTHER PUBLICATIONS

Office Action in CN Application No. 201380065333.6, dated May 23, 2016.
Office Action in CN Application No. 201380065354.8, dated Mar. 7, 2016.
Office Action in CN Application No. 201380065617.5, dated Feb. 29, 2016.
Office Action in CN Application No. 201380065627.9, dated May 6, 2016.
Office Action in CN Patent Application No. 201380065672.4, dated Feb. 29, 2016.
Office Action in JP Application No. 2012-272355, dated Jun. 8, 2016.
Office Action in JP Application No. 2012-272362, dated Aug. 25, 2015.
Office Action in JP Application No. 2012-272366, dated Aug. 25, 2015.
Office Action in JP Application No. 2012-272371, dated Jun. 10, 2016.
Office Action in JP Application No. 2012-272379, dated Jun. 10, 2016.
Office Action in JP Application No. 2012-272383, dated Jun. 10, 2016.
Office Action in U.S. Appl. No. 14/651,227, dated Dec. 13, 2016.
Office Action in U.S. Appl. No. 14/651,228, dated Nov. 18, 2016.
Office Action in U.S. Appl. No. 14/651,229, dated Nov. 21, 2016.
Office Action in U.S. Appl. No. 14/651,230, dated Nov. 2, 2016.
Office Action in U.S. Appl. No. 14/651,231, dated Nov. 1, 2016.
Office Action in U.S. Appl. No. 14/651,648, dated Nov. 2, 2016.
Office Action in U.S. Appl. No. 14/651,667, dated Dec. 13, 2016.
Office Action in U.S. Appl. No. 14/651,668, dated Nov. 25, 2016.
Written Opinion in International Application No. PCT/JP2013/080346, dated Feb. 10, 2014.
Written Opinion in International Application No. PCT/JP2013/080348, dated Feb. 10, 2014.
Written Opinion in International Application No. PCT/JP2013/080953, dated Feb. 10, 2014.
Written Opinion in International Application No. PCT/JP2013/081453, dated Feb. 10, 2014.
Written Opinion in International Patent Application No. PCT/JP2013/080347, dated Feb. 10, 2014.
Written Opinion in PCT/JP2013/081455, dated Feb. 10, 2014.
Written Opinion of ISA in International Application No. PCT/JP2013/082891, dated Feb. 18, 2014.
International Search Report dated Feb. 10, 2014 in International Application No. PCT/JP2013/081454.
Office Action in JP Application No. 2012-272390, dated Jun. 10, 2016.
Extended European Search Report in EP13862226.1, dated Jun. 21, 2016.
Notice of Allowance in U.S. Appl. No. 14/651,227, dated Oct. 6, 2017, 20pp.
Notice of Allowance in U.S. Appl. No. 14/651,667, dated Oct. 17, 2017, 20pp.
Supplemental Notice of Allowability in U.S. Appl. No. 14/651,668, dated Nov. 8, 2017, 5pp.
Office Action in CN Patent Application No. 201380065333.6, dated Jul. 31, 2017. 21pp.
Notice of Allowance in U.S. Appl. No. 14/651,230, dated Oct. 2, 2017. 7pp.
Office Action in U.S. Appl. No. 14/651,228, dated Sep. 27, 2017. 24pp.
Office Action in U.S. Appl. No. 14/651,229, dated Sep. 27, 2017. 15pp.
Office Action in U.S. Appl. No. 14/651,231, dated Sep. 21, 2017. 13pp.
Office Action in CN Application No. 201380065183.9, dated Aug. 21, 2017. 17pp.
Notice of Allowance in U.S. Appl. No. 14/651,668 , dated Oct. 5, 2017. 8pp.
Office Action in U.S. Appl. No. 14/651,669, dated Oct. 10, 2017. 16pp.
Office Action in CN Patent Application No. 201380065627.9, dated Jul. 20, 2017.
Notice of Allowance in U.S. Appl. No. 14/651,648, dated Aug. 23, 2017.
Office Action in EP Application No. 13863278.1, dated Apr. 25, 2018, 5pp.
Office Action in EP Application No. 13861991.1, dated Apr. 25, 2018, 8pp.
Office Action in EP Application No. 13862226.1, dated May 30, 2018, 6pp.

\* cited by examiner

DISPOSABLE DIAPER FOR PETS

RELATED APPLICATIONS

The present application is a National Phase of International Application Number PCT/JP2013/081454, filed Nov. 21, 2013, and claims priority of Japanese Patent Application No. 2012-272377 filed on Dec. 13, 2012.

TECHNICAL FIELD

The present invention relates to a disposable diaper for pets, and more particularly to a disposable diaper for pets that fits well around a waist of a pet.

BACKGROUND ART

It is common to keep pets, typically dogs and cats, indoors. Therefore, various kinds of disposable diapers for pets are available. For example, a disposable diaper for pets as disclosed in Japanese Unexamined Patent Application Publication JP 2004-159591A is provided.

PRIOR ART DOCUMENT

Patent Document

Patent Document 1:
JP 2004-159591A

SUMMARY OF THE INVENTION

Problem to be Solved by the Invention

The disposable diaper for pets (disposable pet diaper) disclosed in JP 2004-159591A is now described with reference to FIGS. 51 and 52. FIG. 51 is a plan view showing the disposable pet diaper in its unfolded state, and FIG. 52 is an explanatory drawing for illustrating a state of the disposable pet diaper worn by a pet.

A disposable pet diaper 1000 includes a liquid-permeable sheet 9910, a liquid-resistant sheet (not shown) and an absorbent core 2000 disposed between the liquid-permeable sheet 9910 and the liquid-resistant sheet.

The liquid-permeable sheet 9910 is formed of liquid-permeable nonwoven fabric. The liquid-resistant sheet is formed of liquid-impermeable plastic film. The absorbent core 2000 is formed of a mixture of liquid absorbent fibers such as pulp, and a super absorbent polymer.

The disposable pet diaper 1000 has an abdomen-side waist area 1110, a back-side waist area 1130 and a crotch area 1120 between the abdomen-side waist area 1110 and the back-side waist area 1130.

The disposable pet diaper 1000 has a diaper longitudinal direction in which the abdomen-side waist area 1110, the crotch area 1120 and the back-side waist area 1130 are contiguously formed, and a diaper transverse direction crossing the diaper longitudinal direction.

The abdomen-side waist area 1110 has an end 1110A and the back-side waist area 1130 has an end 1130A in the diaper longitudinal direction.

An abdomen-side flap 1150 is formed in the abdomen-side waist area 1110 and has a back-side end 1150B. The back-side end 1150B is contiguously formed to extend from an end of the abdomen-side flap 1150 in the diaper transverse direction to a region of an end 2220 of the absorbent core 2000 in the diaper transverse direction.

When the disposable pet diaper 1000 is put on a pet, the abdomen-side flap 1150 comes in contact with a leg α1 of the pet over a relatively long range.

A fastening part 3000 having a plurality of hooks is provided in the abdomen-side flap 1150.

The absorbent core 2000 is disposed in a prescribed region extending over the abdomen-side waist area 1110 and the crotch area 1120. A tail insertion opening 1190 is formed in a prescribed position in the crotch area 1120 and the back-side waist area 1130 where the absorbent core 2000 is not provided.

A fastening region 9000 comprising a target tape is formed in a prescribed position of the back-side waist area 1130. In order to put the disposable pet diaper 1000 on a pet, the hooks on the fastening part 3000 are engaged with the fastening region 9000.

A back-side flap 1160 is formed in the back-side waist area 1130.

A leg stretchable elastic member 4000 is provided in the vicinity of an end of the disposable pet diaper 1000 in the diaper transverse direction. Leg gathers 4410 shown in FIG. 52 are formed by contraction of the leg stretchable elastic member 4000. The leg stretchable elastic member 4000 is arranged to extend over part of the abdomen-side waist area 1110 and the crotch area 1120. Therefore, the contraction force of the leg stretchable elastic member 4000 has no influence on the end 1110A of the abdomen-side waist area 1110 and the end 1130A of the back-side waist area 1130.

A leakproof sheet 8000 is arranged to extend inward from the end of the disposable pet diaper 1000 in the diaper transverse direction. A leakproof sheet stretchable elastic member 6000 is provided in the leakproof sheet 8000. Leakproof gathers and a leakproof wall which are not shown are formed by contraction of the leakproof sheet stretchable elastic member 6000.

An end of the leakproof sheet stretchable elastic member 6000 on the abdomen-side waist area side does not extend up to the end 1110A of the disposable pet diaper 1000 in the diaper longitudinal direction. The back-side end of the leakproof sheet stretchable elastic member 6000 is arranged to extend beyond the tail insertion opening 1190.

In order to put the disposable pet diaper 1000 on a pet, the back-side waist area 1130 is set on a back of the pet and the crotch area 1120 and the abdomen-side waist area 1110 are set on a crotch and an abdomen of the pet, and then the fastening part 3000 is fastened to the fastening region 9000.

In this prior art, however, the back-side flap 1160 is covered with the abdomen-side flap 1150 when the disposable pet diaper 1000 is put on a pet α. Therefore, even if the back-side flap 1160 is creased, it is sometimes hard for the user to notice the fact.

If the back-side flap 1160 is creased, the disposable pet diaper 1000 does not fit well around the waist of the pet α, which may cause leakage of excrement.

Accordingly, it is an object of the present invention to provide a disposable diaper for pets that fits well around a waist of a pet.

Means for Solving the Problem

In order to solve the above-described problem, according to a preferred aspect of the present invention, a disposable diaper for pets is provided which includes a back-side waist area, an abdomen-side waist area, and a crotch area between the abdomen-side waist area and the back-side waist area; a diaper longitudinal direction in which the back-side waist area, the crotch area and the abdomen-side waist area contiguously extend when the disposable diaper is not worn by a pet, and a diaper transverse direction crossing the diaper longitudinal direction; a back-side waist area end in the diaper longitudinal direction, an abdomen-side waist area end in the diaper longitudinal direction, and both ends in the diaper transverse direction; a back-side flap formed in the back-side waist area, an abdomen-side flap formed in the abdomen-side waist area, a tail insertion opening formed in a prescribed region in the diaper longitudinal direction, an absorbent core formed on one side of the tail insertion opening in the diaper longitudinal direction and disposed in a prescribed region extending over the crotch area and the abdomen-side waist area, a fastening part having a prescribed length and provided in the abdomen-side flap, and a fastening region provided in the back-side waist area and configured to receive the fastening part.

Further, at least one of the back-side flap and the abdomen-side flap has an identification region.

When the disposable diaper is put on the pet, the crotch area and the abdomen-side waist area cover a crotch and an abdomen of the pet, while the back-side waist area is closely fitted to a back of the pet, and the fastening part is fastened to the fastening region.

Further, the weight of the absorbent core after excretion is received in the longitudinal direction of the fastening part while the disposable diaper is worn by the pet, and the identification region is configured such that an abnormality of the back-side flap can be identified based on visual information of the identification region from outside the disposable diaper.

In an aspect of the solution according to the present invention, the back-side flap is determined to be in a normal state if the identification region is visible from outside the disposable diaper, while the back-side flap is determined to be in an abnormal state if the identification region is not visible from outside the disposable diaper.

In a further aspect of the solution according to the present invention, the normal state of the back-side flap refers to a state that the back-side flap is not creased when the disposable diaper is worn by the pet, while the abnormal state of the back-side flap refers to a state that at least part of the back-side flap is creased when the disposable diaper is worn by the pet.

In a further aspect of the solution according to the present invention, the identification region is formed in the back-side flap.

In a further aspect of the solution according to the present invention, the identification region comprises a first extended identification region extended in a transverse direction from the back-side flap.

In a further aspect of the solution according to the present invention, the identification region comprises a second extended identification region extended in a longitudinal direction from the back-side flap.

In a further aspect of the solution according to the present invention, the identification region comprises a colored identification region that is differently colored from the other region of the back-side flap.

In a further aspect of the solution according to the present invention, the identification region in the back-side flap protrudes from an end of the abdomen-side flap in the longitudinal direction when the disposable diaper is worn by the pet.

In a further aspect of the solution according to the present invention, the disposable diaper includes a first virtual line extending in the diaper transverse direction from a back-side end of the identification region in the back-side flap, a second virtual line extending in the diaper transverse direction from a back-side end of the fastening region in the back-side flap, a third virtual line connecting the first virtual line and the second virtual line and extending in the diaper longitudinal direction, a fourth virtual line extending in the diaper transverse direction from a back-side end of the fastening part in the abdomen-side flap, a fifth virtual line extending from an abdomen-side end of the abdomen-side flap in the diaper transverse direction, and a sixth virtual line connecting the fourth virtual line and the fifth virtual line and extending in the diaper longitudinal direction. Further, the third virtual line is longer than the sixth virtual line.

In a further aspect of the solution according to the present invention, the identification region is formed in the abdomen-side flap.

In a further aspect of the solution according to the present invention, the identification region is a visible region that is formed in the abdomen-side flap for checking the state of the back-side flap.

In a further aspect of the solution according to the present invention, the visible region is a light transmissive identification region which is capable of transmitting light.

In a further aspect of the solution according to the present invention, the visible region is a cutout identification region formed by cutting out an abdomen-side end portion of the abdomen-side flap.

In a further aspect of the solution according to the present invention, the visible region is a first open identification region formed by an opening in the abdomen-side flap.

In a further aspect of the solution according to the present invention, the visible region includes a second open identification region formed by an opening in the abdomen-side flap, and a cover region configured to cover the second open identification region and to be freely opened and closed with respect to the second open identification region.

In a further aspect of the solution according to the present invention, the identification region includes a back-side flap identification region formed in the back-side flap and an abdomen-side flap identification region formed in the abdomen-side flap.

Effect of the Invention

In this invention, by provision of the identification region which is configured such that an abnormality of the back-side flap can be identified based on visual information of the identification region from outside the disposable diaper, the user can properly set the back-side flap when putting the disposable diaper on a pet. Therefore, the disposable diaper for pets fits well around the waist of the pet.

BEST MODES FOR CARRYING OUT THE INVENTION

First Embodiment

A first embodiment of the present invention is now described with reference to FIGS. 1 to 20.

Figure 1:
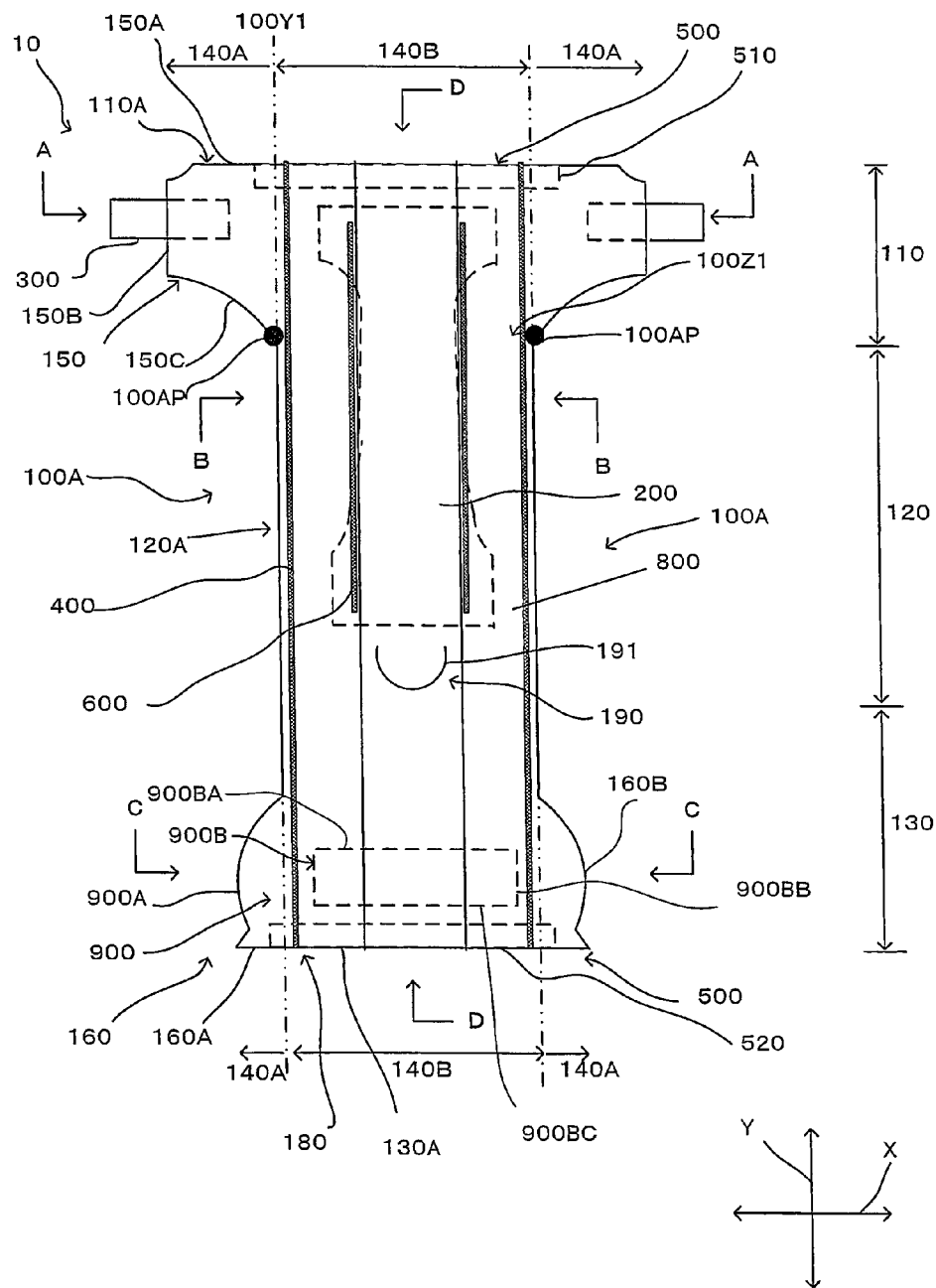
FIG. 1 is a plan view showing a disposable diaper for pets according to a first embodiment of the present invention, in its unfolded state.

FIG. 1 is a plan view showing a disposable diaper for pets in its unfolded state. The "pet" in this embodiment widely includes vertebrates (mammals, reptiles, birds and amphibians) and invertebrates, and typically represents pets such as cats, dogs, rabbits, hamsters, horses, cows, pigs and goats. The term "unfolded state" as used in this embodiment refers to the state in which an unused disposable diaper is unfolded or opened and a contraction force of a stretchable elastic member is not developed.

A disposable diaper for pets (disposable pet diaper) 10 has an abdomen-side waist area 110, a back-side waist area 130 and a crotch area 120 between the abdomen-side waist area 110 and the back-side waist area 130. When the disposable pet diaper 10 is worn by a pet, the abdomen-side waist area 110, the back-side waist area 130 and the crotch area 120 are in contact with an abdomen, a back and a crotch of the pet, respectively.

The abdomen-side waist area 110, the back-side waist area 130 and the crotch area 120 are example embodiments that correspond to the "abdomen-side waist area, the back-side waist area and the crotch area between the abdomen-side waist area and the back-side waist area", respectively, according to this invention.

In the unfolded state as shown in FIG. 1, the disposable pet diaper 10 has a diaper longitudinal direction Y in which the abdomen-side waist area 110, the crotch area 120 and the back-side waist area 130 contiguously extend, and a diaper transverse direction X crossing the diaper longitudinal direction Y. The term "crossing" as used in this specification means "perpendicularly crossing" unless otherwise specified.

The diaper longitudinal direction Y and the diaper transverse direction X are example embodiments that correspond to the "diaper longitudinal direction in which the abdomen-side waist area, the crotch area and the back-side waist area contiguously extend when the disposable diaper is not worn by a pet, and a diaper transverse direction crossing the diaper longitudinal direction", respectively, according to this invention.

The disposable pet diaper 10 has an inside surface 100Z1 which faces a pet and an outside surface 100Z2 opposite to the inside surface 100Z1.

In this embodiment, the inside surface 100Z1 may also be referred to as a pet-side surface or a pet wearing surface.

The disposable pet diaper 10 has an end 110A formed in the abdomen-side waist area 110 and an end 130A formed in the back-side waist area 130 in the diaper longitudinal direction Y.

The end 110A formed in the abdomen-side waist area 110 is an example embodiment that corresponds to the "abdomen-side waist area end in the diaper longitudinal direction" according to this invention.

The end 130A formed in the back-side waist area 130 is an example embodiment that corresponds to the "back-side waist area end in the diaper longitudinal direction" according to this invention.

The disposable pet diaper 10 has a pair of ends 100A in the diaper transverse direction X. Each of the ends 100A contiguously extends over an end 150B in the diaper transverse direction and a back-side end 150C in an abdomen-side flap 150, an end 160B in the diaper transverse direction in a back-side flaps 160, and a leg-side end 120A between the back-side end 150C of the abdomen-side flap 150 and the end 160B of the back-side flap 160 in the diaper transverse direction.

The ends 100A are an example embodiment that corresponds to the "both ends in the diaper transverse direction" according to this invention.

Further, the end 160B of the back-side flap 160 in the diaper transverse direction may also be referred to as a lateral end.

The disposable pet diaper 10 has a tail insertion opening 190 formed in a prescribed region in the diaper longitudinal direction Y. The tail insertion opening 190 is formed by an arcuate cut 191 extending through the inside surface 100Z1 and the outside surface 100Z2.

Although, in the first embodiment, the tail insertion opening 190 is formed by the arcuate cut 191, it may be a circular opening formed by an annular cut.

The tail insertion opening 190 is an example embodiment that corresponds to the "tail insertion opening formed in a prescribed region in the diaper longitudinal direction" according to this invention.

The disposable pet diaper 10 has an absorbent core 200 formed on one side of the tail insertion opening 190 in the diaper longitudinal direction Y and disposed in a prescribed region extending over the crotch area 120 and the abdomen-side waist area 110. The absorbent core 200 has an abdomen-side end 210, a back-side end 220 and a pair of ends 230 in the diaper transverse direction.

The absorbent core 200 is formed of a mixture of a particulate or fibrous super absorbent polymer and fluff pulp or a mixture of a particulate or fibrous super absorbent polymer, fluff pulp and thermoplastic synthetic resin fibers. Preferably, in order to prevent deformation of the absorbent core 200 and falling off of the super absorbent polymer, the absorbent core 200 may be entirely covered with a liquid-permeable sheet such as tissue paper and hydrophilic fiber nonwoven fabric. Further, preferably, the absorbent core 200 may be compressed into a prescribed thickness in the manufacturing process. As the super absorbent polymer, synthetic polymer-based, starch-based or cellulose-based polymer can be appropriately used.

The absorbent core 200 is an example embodiment that corresponds to the "absorbent core formed on one side of the tail insertion opening in the diaper longitudinal direction and disposed in a prescribed region extending over the crotch area and the abdomen-side waist area" according to this invention.

Figure 2:
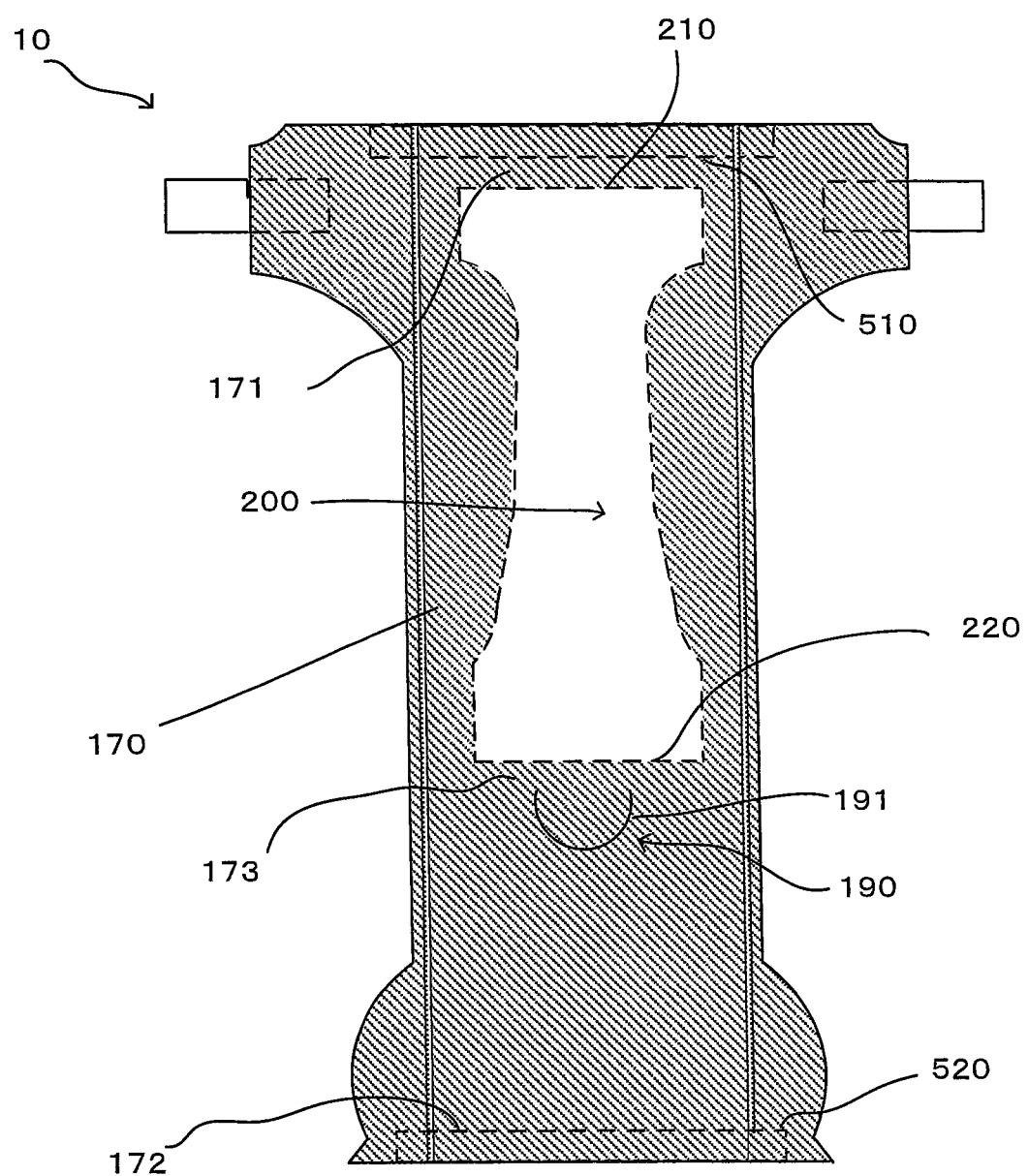
FIG. 2 is a plan view for showing an absorbent-core non-arrangement region in the unfolded state of the disposable diaper.

As shown in FIG. 2, a region of the disposable pet diaper 10 in which the absorbent core 200 is not disposed is referred to as an absorbent-core non-arrangement region 170.

In the absorbent-core non-arrangement region 170, regions adjacent to the abdomen-side end 210 and the back-side end 220 of the absorbent core 200 and to the back-side end 130A of the disposable pet diaper 10 each form an erected region for forming an erected section 700 which is described below. Specifically, the region adjacent to the abdomen-side end 210 of the absorbent core 200, the region adjacent to the back-side end 220 of the absorbent core 200, and the region adjacent to the back-side end 130A of the disposable pet diaper 10 are referred to as an abdomen-side erected region 171, a crotch-side erected region 173 and a back-side erected region 172, respectively.

Depending on design of the disposable pet diaper 10, part of the absorbent core 200 may be disposed within the absorbent-core non-arrangement region 170, especially in any of the erected regions. Specifically, part of tissue paper, pulp fibers or super absorbent polymer may be disposed in the erected region. Even in such a case, if the erected region maintains its flexibility and forms the erected section 700, the absorbent-core non-arrangement region 170 is considered as being substantially formed and the erected region is also considered as being formed at the same time.

The disposable pet diaper 10 has fastening parts 300 on the both ends 150B of the abdomen-side flap 150 in the diaper transverse direction.

Figure 3:
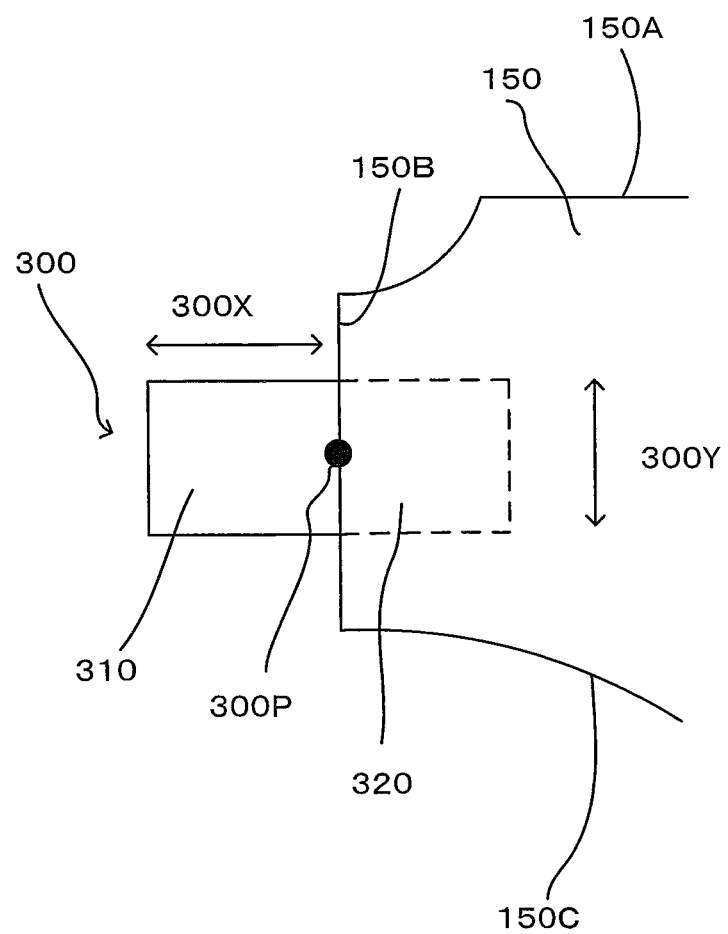
FIG. 3 is an explanatory drawing for illustrating the structure of a fastening part.

As shown in FIG. 3, each of the fastening parts 300 has a fastening part longitudinal direction 300X and a fastening part transverse direction 300Y. In the fastening part longitudinal direction 300X, the fastening part 300 has a fixed part 320 in which the fastening part 300 is fixed to the disposable pet diaper 10, and a free part 310 provided to be fastened to a fastening region 900.

The fastening part 300 is a fiber nonwoven fabric made of polyolefin thermoplastic synthetic fibers, or a plastic film made of polyolefin thermoplastic synthetic resin. A plurality of hooks (not shown) are provided on the diaper inside surface 100Z1 of the free part 310. The hooks are formed of polyolefin thermoplastic synthetic resin. Although the hooks here are provided and configured to be fastened to the fastening region 900, other structures such as an adhesive can be selected for use in place of the hooks, depending on the structure of the fastening region 900.

The fastening part 300 is an example embodiment that corresponds to the "fastening part having a prescribed length and provided in the abdomen-side waist area" according to this invention.

The disposable pet diaper 10 has flaps 140A. The flaps 140A include a pair of abdomen-side flaps 150 formed on the both ends 100A in the diaper transverse direction in the abdomen-side waist area 110, and a pair of back-side flaps 160 formed on the both ends 100A in the diaper transverse direction in the back-side waist area 130. The flaps 140A are defined by a pair of virtual lines 100Y1 extending in the diaper longitudinal direction and passing through a pair of minimum width points 100AP on the ends 100A of the disposable pet diaper 10 in the diaper transverse direction between which a line connecting the ends 100A in the diaper transverse direction is shortest. Specifically, the virtual lines 100Y1 are referred to as flap boundary lines, and regions outside a pair of the flap boundary lines 100Y1 are referred to as flaps (the abdomen-side flaps 150, the back-side flaps 160), while an inside region between the flap boundary lines 100Y1 is referred to as a body 140B. Further, each of the flap boundary lines 100Y1 itself can also be defined as a reference virtual straight line which is an arbitrary straight line extending in the diaper longitudinal direction.

The abdomen-side flap 150 is an example embodiment that corresponds to the "abdomen-side flap provided in the abdomen-side waist area" according to this invention.

The back-side flap 160 is an example embodiment that corresponds to the "back-side flap provided on the back-side waist area" according to this invention.

Figure 4:
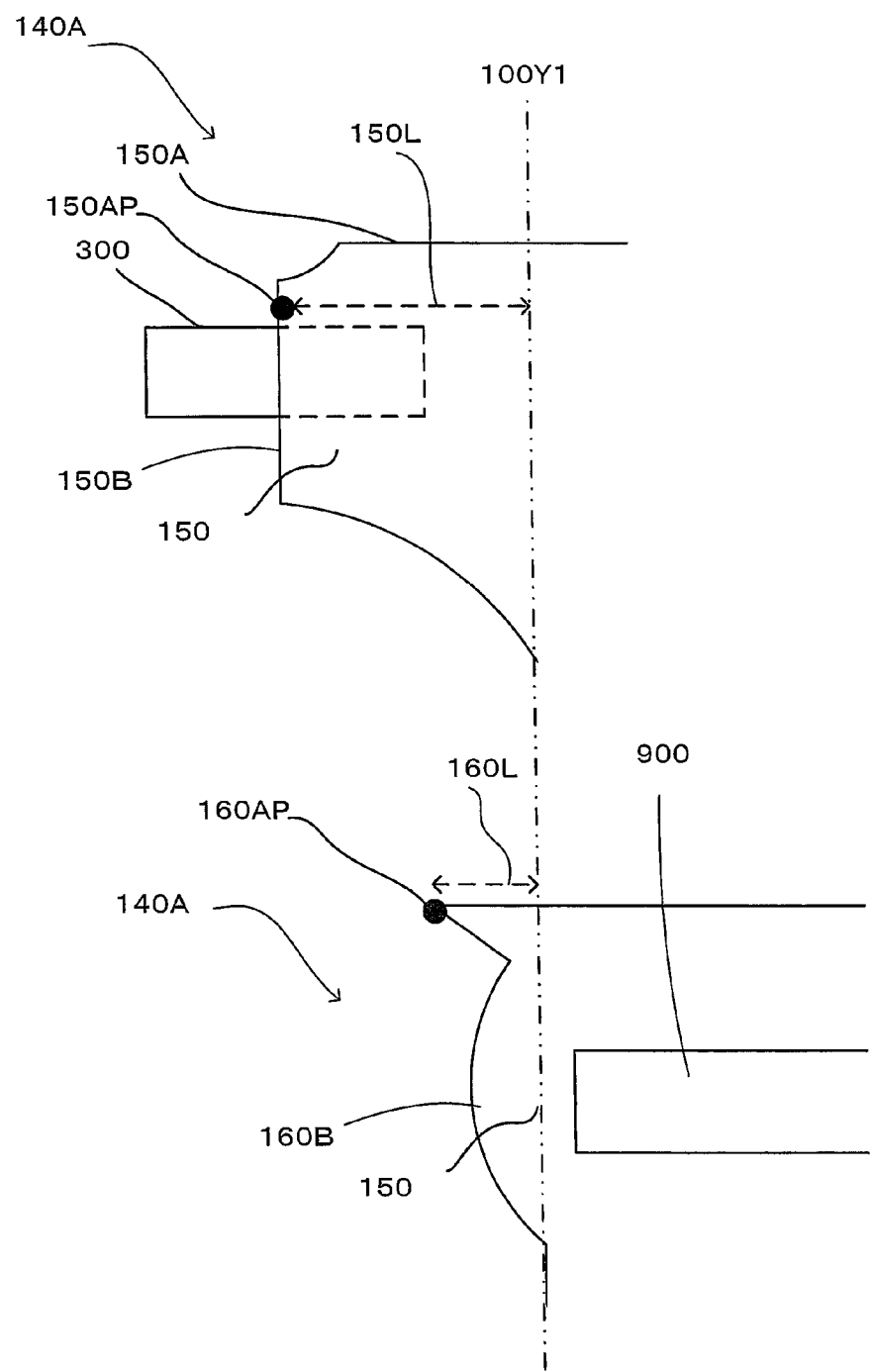
FIG. 4 is an explanatory drawing for illustrating the structure of a flap.

The structure of the flap 140A is now described with reference to FIG. 4. In FIG. 4, for comparison, the abdomen-side flap 150 and the back-side flap 160 are shown aligned vertically on the flap boundary line 100Y1.

First, the length of the flap 140A in the diaper transverse direction X is defined. Where a straight line in the diaper transverse direction X which connects points on the both ends in the diaper transverse direction in each pair of the flaps 140A is longest, the points are defined as maximum width points. The maximum width points are shown as a maximum width point 150AP and a maximum width point 160AP in the abdomen-side flap 150 and the back-side flap 160, respectively.

Next, the shortest distance between the flap boundary line 100Y1 and the maximum width points is measured and defined as a length of the flap 140A in the diaper transverse direction X. The length of the flap 140A in the diaper transverse direction X is shown as a length 150L of the abdomen-side flap 150 and a length 160L of the back-side flap 160.

In this invention, the length 150L of the abdomen-side flap 150 is different from the length 160L of the back-side flap 160.

With such a structure, one of the abdomen-side flap 150 and the back-side flap 160 can be made shorter in the diaper transverse direction X. Consequently, the possibility of occurrence of crease of the shorter flap 140A can be reduced.

The "crease" in this embodiment encompasses a state in which the inside surfaces 100Z1 of the flaps 140A contact each other, a state in which the outside surfaces 100Z1 of the flaps 140A contact each other, and a state in which the flaps 140A are creased or wrinkled to such an extent as to impair the fitness of the disposable pet diaper 10 to the pet α.

Further, in the first embodiment of this invention, the length 160L of the back-side flap 160 is configured to be shorter than the length 150L of the abdomen-side flap 150.

Figure 5:
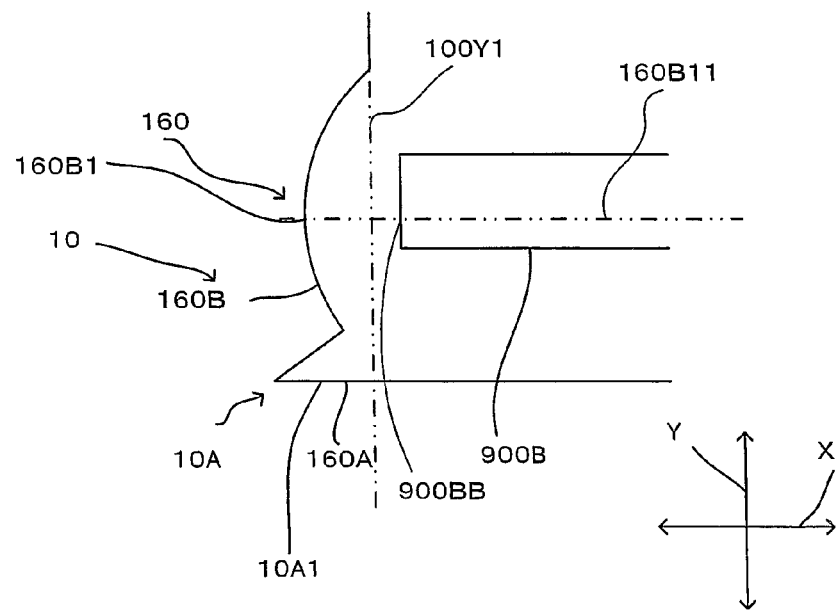
FIG. 5 is an explanatory drawing for illustrating the structure of a back-side flap.

Next, the structure of the back-side flap 160 is now described with reference to FIG. 5.

The lateral end 160B of the back-side flap 160 is shaped such that the distance in the diaper transverse direction X between the lateral end 160B and the flap boundary line 100Y1 is not uniform.

Thus, the lateral end 160B of the back-side flap 160 is formed such that its shape gradually changes in the diaper longitudinal direction Y.

Specifically, in this embodiment, the lateral end 160B of the back-side flap 160 has a circular arc shape. In this embodiment, the "circular arc shape" is not limited to the shape of a circular arc of a perfect circle, but it also includes other circular arc shapes such as that of an ellipse and a combination of circular arc shapes of a perfect circle and an ellipse. Accordingly, the "circular arc shape" in this embodiment may also be referred to as a shape other than a linear shape.

By thus shaping the lateral end 160B of the back-side flap 160, when the user grabs the back-side flap 160, the user can easily confirm by the feel which part of the lateral end 160B of the back-side flap 160 the user is grabbing.

A maximum width region 160B1 is formed in a central region of the lateral end 160B of the back-side flap 160 where the distance between the lateral end 160B and the flap boundary line 100Y1 becomes maximum. The "central region" as used in this embodiment refers to a region not having an identification region 10A especially in a structure in which the identification region 10A (which is described below) is formed by extending the back-side end 160A of the back-side flap 160.

The maximum width region 160B1 is formed by defining the lateral end 160B of the back-side flap 160 by a circular arc curve which defines the maximum width region 160B1 having a maximum width (such that the back-side flap 160 has a maximum width at the maximum width region 160B1).

By providing the maximum width region 160B1, when the user grabs the back-side flap 160, the user can more easily confirm by the feel which part of the lateral end 160B of the back-side flap 160 the user is grabbing.

The fastening region 900 which is described below is formed on a virtual line 160B11 extending in the diaper transverse direction X and passing through the maximum width region 160B1.

Specifically, a second fastening region 900B in the fastening region 900 is provided on the virtual line 160B11 extending in the diaper transverse direction X and passing through the maximum width region 160B1.

Due to such a relation between the maximum width region 160B1 and the fastening region 900, the user can more easily position the fastening part 300 of the abdomen-side flap 150 on the fastening region 900 of the back-side flap 160. Specifically, when the user grabs the back-side flap 160, the user can recognize the maximum width region 160B1 and thus can recognize the position of the fastening region 900 at the same time.

Further, an end 900BB of the fastening region 900 in the diaper transverse direction X has a different shape from the lateral end 160B of the back-side flap 160. The end 900BB of the fastening region 900 in the diaper transverse direction X is also referred to as the "lateral end".

Specifically, the lateral end 900BB of the second fastening region 900B has a linear shape parallel to the diaper longitudinal direction Y, while the lateral end 160B of the back-side flap 160 has a curved shape.

Due to such a relation between the lateral end 160B of the back-side flap 160 and the lateral end 900BB of the fastening region 900, the user can more easily position the fastening part 300 of the abdomen-side flap 150 on the fastening region 900 of the back-side flap 160. Specifically, when the user grabs the back-side flap 160, the user can recognize the maximum width region 160B1 and thus can recognize the position of the fastening region 900 at the same time. Further, from the difference in shape between the lateral end 160B of the back-side flap 160 and the lateral end 900BB of the fastening region 900, the user can easily recognize the position of the lateral end 900BB of the fastening region 900 itself or the position in the fastening region 900 in the diaper transverse direction X.

The identification region 10A is formed in the flap 140A and provided to allow the user to identify an abnormality of the back-side flap 160 by visually and externally checking the disposable pet diaper 10 worn by the pet α.

The identification region 10A is an example embodiment that corresponds to the feature that "at least one of the abdomen-side flap and the back-side flap has an identification region, and the identification region is configured such that an abnormality of the back-side flap can be identified based on visual information of the identification region from outside the disposable diaper" according to this invention.

In this respect, in this embodiment, if the identification region 10A is visible from outside the disposable pet diaper 10, "the back-side flap 160 is determined to be in a normal state". On the other hand, if the identification region 10A is not visible from outside the disposable pet diaper 10, "the back-side flap 160 is determined to be in an abnormal state". In this embodiment, the "identification region 10A is visible" means not only that "the whole identification region 10A is visible", but also that "part of the identification region 10A is visible". Specifically, it is sufficient that a user is allowed to recognize whether the back-side flap 160 is in a normal state or in an abnormal state by "visually checking part of the identification region 10A".

This is an example embodiment that corresponds to the feature that "the back-side flap is determined to be in a normal state if the identification region is visible from outside the disposable diaper, while the back-side flap 160 is determined to be in an abnormal state if the identification region is not visible from outside the disposable diaper" according to this invention.

The "normal state" of the back-side flap 160 refers to a state that the back-side flap 160 is not creased when the disposable pet diaper 10 is worn by the pet α, while the "abnormal state" of the back-side flap 160 refers to a state that the back-side flap 160 is creased when the disposable pet diaper 10 is worn by the pet α.

This is an example embodiment that corresponds to the feature that "the normal state of the back-side flap refers to a state that the back-side flap is not creased when the disposable diaper is worn by the pet, while the abnormal state of the back-side flap refers to a state that at least part of the back-side flap is creased when the disposable diaper is worn by the pet" according to this invention.

Next, the structure of the identification region 10A is more specifically explained.

In this embodiment, the identification region 10A is formed in the back-side flap 160. This is an example embodiment that corresponds to the feature that "the identification region is formed in the back-side flap" according to this invention.

The identification region 10A is formed by extending the back-side end 160A in the diaper longitudinal direction Y and a region of the lateral end 160B contiguous to the back-side end 160A in the back-side flap 160, in the diaper transverse direction X. This identification region 10A formed by extending a prescribed region of the lateral end 160B of the back-side flap 160 is referred to as a first extended identification region 10A1.

This is an example embodiment that corresponds to the feature that "the identification region comprises a first extended identification region extended in a transverse direction from the back-side flap" according to this invention.

The identification region 10A is configured to protrude from an end 150A of the abdomen-side flap 150 in the diaper longitudinal direction Y when the disposable pet diaper 10 is worn by the pet α.

This is an example embodiment that corresponds to the feature that "the identification region in the back-side flap protrudes from an end of the abdomen-side flap in the longitudinal direction when the disposable diaper is worn by the pet" according to this invention.

The structure in which the identification region 10A protrudes from the end 150A of the abdomen-side flap 150 is now specifically described with reference to FIG. 6.

Figure 6:
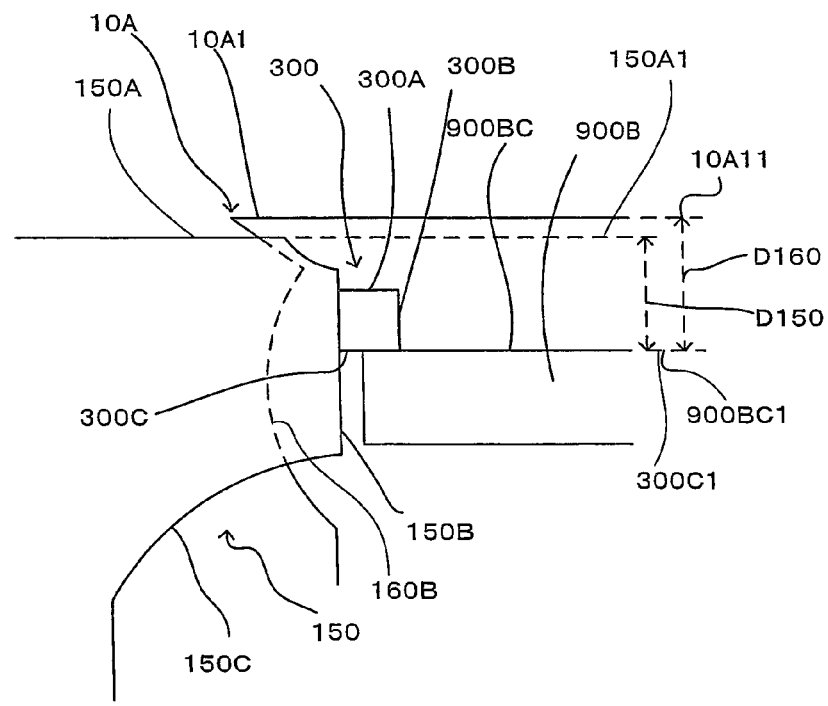
FIG. 6 is an explanatory drawing for illustrating the structure of an identification region.

In FIG. 6, the abdomen-side flap 150 and the back-side flap 160 are shown side by side so as to make it easy to understand the relation between the identification region 10A in the back-side flap 160 and the abdomen-side flap 150.

First, a virtual line extending in the diaper transverse direction X from an end of the identification region 10A in the diaper longitudinal direction Y in the back-side flap 160 is referred to as a first virtual line 10A11.

The first virtual line 10A11 is an example embodiment that corresponds to the "first virtual line extending in the diaper transverse direction from a back-side end of the identification region in the back-side flap" according to this invention.

Next, a virtual line extending in the diaper transverse direction X from a back-side end 900BC of the second fastening region 900B of the fastening region 900 in the back-side flap 160 is referred to as a second virtual line 900BC1.

The second virtual line 900BC1 is an example embodiment that corresponds to the "second virtual line extending in the diaper transverse direction from a back-side end of the fastening region in the back-side flap" according to this invention.

Next, a virtual line connecting the first virtual line 10A11 and the second virtual line 900BC1 and extending in the diaper longitudinal direction Y is referred to as a third virtual line D160.

The third virtual line D160 is an example embodiment that corresponds to the "third virtual line connecting the first virtual line and the second virtual line and extending in the diaper longitudinal direction" according to this invention.

Further, a virtual line extending in the diaper transverse direction X from a back-side end 300C of the fastening part 300 in the abdomen-side flap 150 is referred to as a fourth virtual line 300C1.

The fourth virtual line 300C1 is an example embodiment that corresponds to the "fourth virtual line extending in the diaper transverse direction from a back-side end of the fastening part in the abdomen-side flap" according to this invention.

Further, a virtual line extending from an abdomen-side end 150A of the abdomen-side flap 150 in the diaper transverse direction X is referred to as a fifth virtual line 150A1.

The fifth virtual line 150A1 is an example embodiment that corresponds to the "fifth virtual line extending from an abdomen-side end of the abdomen-side flap in the diaper transverse direction" according to this invention.

Further, a virtual line connecting the fourth virtual line 300C1 and the fifth virtual line 150A1 and extending in the diaper longitudinal direction Y is referred to as a sixth virtual line D150.

The sixth virtual line D150 is an example embodiment that corresponds to the "sixth virtual line connecting the fourth virtual line and the fifth virtual line and extending in the diaper longitudinal direction" according to this invention.

The third virtual line D160 is longer than the sixth virtual line D150.

This relation between the third virtual line D160 and the sixth virtual line D150 is an example embodiment that corresponds to the feature that "the third virtual line is longer than the sixth virtual line" according to this invention.

By provision of such configuration, the identification region 10A can be easily identified.

Specifically, when the disposable pet diaper 10 is put on the pet α, the identification region 10A always protrudes from the abdomen-side end 150A of the abdomen-side flap 150 wherever the free part 310 of the fastening part 300 in the abdomen-side flap 150 is fastened to the second fastening region 900B of the fastening region 900 in the back-side flap 160.

The fastening region 900 is now explained, starting with its basic structure with reference to FIG. 1.

The fastening region 900 is formed at least in the back-side waist area 130 in the disposable pet diaper 10 and can be removably engaged with a hook part (hooks) provided in the free part 310 of the fastening part 300.

The fastening region 900 is an example embodiment that corresponds to the "fastening region provided in the back-side waist area and configured to receive the fastening part" according to this invention.

In the fastening region 900, nonwoven fabric which can be removably engaged with the hook part of the fastening part 300 is used as an outer sheet 930 which forms the outside surface 100Z2 of the disposable pet diaper 10. A first fastening region 900A is formed by this nonwoven fabric which can be removably engaged with the hook part of the fastening part 300.

The first fastening region 900A is provided in the absorbent-core non-arrangement region 170, or specifically, configured to be placed on the back of the pet α. Allowing for some pets α having large inclination on the back, the fastening region 900 for fixing the fastening part 300 needs to have a flexible structure in order to fit on the back of the pets α.

Further, a back-side waist stretchable elastic member 520 which is described below is arranged to extend in the diaper transverse direction in the absorbent-core non-arrangement region 170 within the back-side waist area 130 of the disposable pet diaper 10. More specifically, the back-side waist stretchable elastic member 520 is provided in a stretched state in the vicinity of the back-side end 130A of the disposable pet diaper 10.

The back-side waist stretchable elastic member 520 contracts when the disposable pet diaper 10 is put on the pet. As a result, a first back-side curved part 542 is formed, so that the back-side waist area 130 of the disposable pet diaper 10 can be more easily put on the pet α.

A force of engagement between the first fastening region 900A and the fastening part 300 is preferably in a range of 1.1 to 4.2 N.

The second fastening region 900B is provided on the outside surface 100Z2 in the first fastening region 900A and has a stronger force of engagement with the hook part of the fastening part 300 than the first fastening region 900A.

Specifically, the second fastening region 900B is formed by a target tape which is a fiber nonwoven fabric made of polyolefin thermoplastic synthetic fibers, or a plastic film made of polyolefin thermoplastic synthetic resin, and having a large number of loops (not shown) made of polyolefin thermoplastic synthetic resin.

Due to such a structure, the disposable pet diaper 10 can be more firmly put on the pet α.

Specifically, when the user puts the disposable pet diaper 10 on the pet α, only part of the hook part of the fastening part 300 may be fastened to the second fastening region 900B (target tape). Even in such a case, the other part of the hook part which is not fastened to the second fastening region 900B is fastened to the first fastening region 900A. Therefore, in any situation, the hook part of the fastening part 300 is fastened to either the first fastening region 900A or the second fastening region 900B, so that the disposable pet diaper 10 can be securely put on the pet α.

The structure of the first fastening region 900A is now described with reference to FIGS. 7 and 8.

Figure 7:
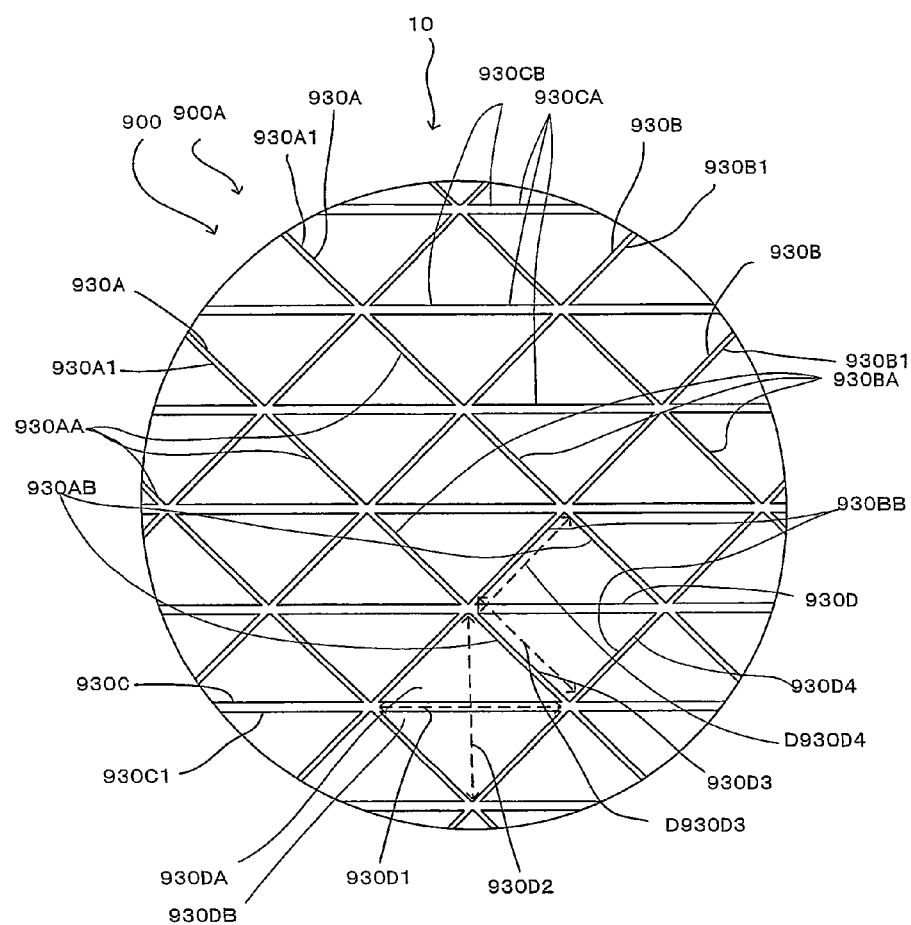
FIG. 7 is an enlarged view for illustrating the structure of a fastening region.
Figure 8:
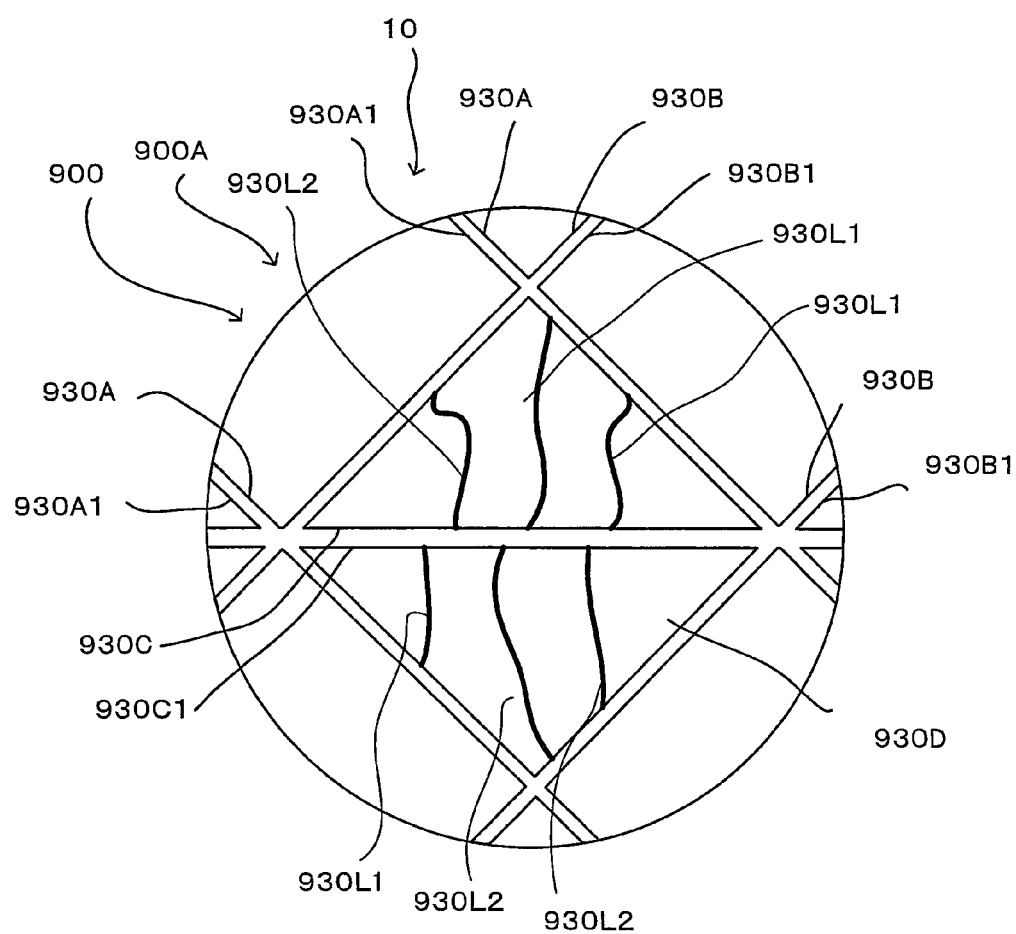
FIG. 8 is an explanatory drawing for illustrating the operation of the fastening region.

FIG. 7 is an enlarged, explanatory view showing the first fastening region 900A, and FIG. 8 is an enlarged, explanatory view showing surrounding parts 930D formed in the first fastening region 900A.

The outer sheet 930 forms the first fastening region 900A and is formed of thermoplastic fibers.

The outer sheet 930 has a first welded part 930A extending in a first direction and formed by melting of the thermoplastic fibers.

A plurality of such first welded parts 930A form a first welded part group 930AA.

Further, each pair of adjacent ones of the first welded parts 930A form a first adjacent welded part group 930AB.

The outer sheet 930 further has a second welded part 930B extending in a second direction crossing the first direction and formed by melting of the thermoplastic fibers. The term "crossing" here does not necessarily mean "perpendicularly crossing".

A plurality of such second welded parts 930B form a second welded part group 930BA.

Further, each pair of adjacent ones of the second welded parts 930B form a second adjacent welded part group 930BB.

The surrounding parts 930D each having a parallelogram shape are formed in regions surrounded by the first adjacent welded part group 930AB and the second adjacent welded part group 930BB which intersect with each other. The "parallelogram" as used herein includes a square and a rectangle.

The outer sheet 930 further has a third welded part 930C extending in a third direction crossing the first and second directions and formed within the surrounding part 930D by melting of the thermoplastic fibers. The term "crossing" here does not necessarily mean "perpendicularly crossing".

A plurality of such third welded parts 930C form a third welded part group 930CA.

Further, each pair of adjacent ones of the third welded parts 930C form a third adjacent welded part group 930CB.

A first loop part 930L1 is formed between the first welded part 930A and the third welded part 930C by thermoplastic fibers which are not welded. Specifically, the first loop part 930L1 is fixed at both ends to the first and third welded parts 930A, 930C and is formed in a loop by fibers extending between the both ends. The first loop part 930L1 can be removably engaged with the hook part of the fastening part 300.

A second loop part 930L2 is formed between the second welded part 930B and the third welded part 930C by thermoplastic fibers which are not welded. Specifically, the second loop part 930L2 is fixed at both ends to the second and third welded parts 930B, 930C and formed in a loop by fibers extending between the both ends. The second loop part 930L2 can be removably engaged with the hook part of the fastening part 300.

The surrounding part 930D has a parallelogram shape having a first diagonal line 930D1 and a second diagonal line 930D2. Further, the surrounding part 930D is partitioned into a first surrounding part 930DA and a second surrounding part 930DB by the third welded part 930C.

The third direction in which the third welded part 930C extends is preferably parallel to one of the diagonal lines of the parallelogram which defines the surrounding part 930D.

Further, in this case, the third welded part 930C is preferably formed to coincide with one of the diagonal lines of the parallelogram which defines the surrounding part 930D. In this embodiment, the third welded part 930C is arranged to coincide with the first diagonal line 930D1 of the diagonal line 930D. By such arrangement of the third welded part 930C on the diagonal line of the surrounding part 930D, the first surrounding part 930DA and the second surrounding part 930DB have the same size. Therefore, the first and second loops 930L1, 930L2 formed in the first and second surrounding parts 930DA, 930DB can be made uniform in size between the first surrounding part 930DA and the second surrounding part 930DB.

The surrounding part 930D has a first side 930D3 and a second side 930D4. In order to obtain satisfactorily engaged state with respect to the hook part of the fastening part 300 which is generally used, it is preferable that a length D930D3 of the first side 930D3 and a length D930D4 of the second side 930D4 of the surrounding part 930D are each in a range of 2 to 10 mm.

In this embodiment, the first welded part 930A has a continuous linear shape and forms a first welded continuous line 930A1.

In this embodiment, the second welded part 930B has a continuous linear shape and forms a second welded continuous line 930B 1.

In this embodiment, the third welded part 930C has a continuous linear shape and forms a third welded continuous line 930C1.

The width of each of the first welded part 930A and the second welded part 930B is preferably in a range of 0.2 to 2 mm. The width of the third welded part 930C is preferably in a range of 0.2 to 5 mm. The distance between each pair of the third welded parts 930C which form the third adjacent welded part group is preferably in a range of 2 to 10 mm. By provision of such settings of the widths of the first and second welded parts 930A, 930B and the distance between each pair of the third welded parts 930C which form the third adjacent welded part group, the first fastening region 900A can be prevented from impairing flexibility and touch feeling as the outer sheet 930 which forms the outside surface 100Z2 of the disposable pet diaper 10.

Operation of the first fastening region 900A is now described.

The user attaches the hook part of the fastening part 300 to the first fastening region 900A in order to put the disposable pet diaper 10 on the pet α. At this time, the hook part of the fastening part 300 is engaged with at least one of the first loop parts 930L1 and the second loop parts 930L2.

When a shearing force is generated in the fastening part 300, the first loop parts 930L1 and the second loop parts 930L2 engaged with the hook part of the fastening part 300 move as the hook part moves. At this time, however, the both ends of the first loop parts 930L1 are fixed to the first welded parts 930A and the third welded parts 930C, and the both ends of the second loop parts 930L2 are fixed to the second welded parts 930B and the third welded parts 930C. Therefore, movement of the first loop parts 930L1 and the second loop parts 930L2 is restricted, so that the loop parts are not easily disengaged from the hook part.

The outer sheet 930 forming the first fastening region 900A is an assembly of filaments or staples, more preferably an assembly of filaments, of thermoplastic fibers having fineness of 1 to 3 dtex. It is preferable that the staples, if used, have at least twice the length of the longest side of the surrounding part 930D (which is described below), specifically a length of 50 mm or longer.

The outer sheet 930 has a mass per unit area of 15 to 40 g/m².

The outer sheet 930 can take the form of nonwoven fabric by forming the first, second and third welded parts 930A, 930B, 930C in the assembly of such filaments or staples. In place of such nonwoven fabric, the first, second and third welded parts 930A, 930B, 930C may be formed in other forms of nonwoven fabric, such as thermal bond nonwoven fabric.

In order to form the outer sheet 930 forming the first fastening region 900A, first, a web formed of the assembly of thermoplastic fibers for forming the outer sheet 930 is obtained.

Pressure is locally applied to the web by a heated emboss roller, while the web is continuously fed in one direction. The thermoplastic fibers are welded by the heated emboss roller, and the first, second and third welded parts 930A, 930B, 930C are formed. The web is fixed by the first, second and third welded parts 930A, 930B, 930C. In this manner, the outer sheet 930 is obtained.

The emboss roller is used in a state of being heated up to a temperature at which the thermoplastic fibers melt. The first, second and third welded parts 930A, 930B, 930C thus obtained are welded to such an extent that the thermoplastic fibers cannot be separated from each other.

In this manner, the first, second and third welded parts 930A, 930B, 930C are formed by the emboss roller. Therefore, the first, second and third welded parts 930A, 930B, 930C are recessed compared with other parts of the outer sheet 930 not having these welded parts.

Therefore, in the disposable pet diaper 10 using the outer sheet 930, the first, second and third welded parts 930A, 930B, 930C are recessed from the outside surface 100Z2 of the fastening region 900.

Specifically, the surrounding part 930D in which the first, second and third welded parts 930A, 930B, 930C are not formed forms a raised part in the outside surface 100Z2 of the first fastening region 900A of the fastening region 900.

Such configuration facilitates user's operation of fixing the hook part of the fastening part 300 to the first fastening region 900A.

Now, the structure of the abdomen-side flap 150 is explained.

As shown in FIG. 3, in the abdomen-side flap 150, the free end 310 of the fastening part 300 protrudes from the end 150B in the diaper transverse direction. A point which bisects the fastening part 300 in the fastening part transverse direction 300Y on a boundary between the end 150B and the fastening part 300 (on a part of the end 150B overlapped with the fastening part 300) is referred to as a fastening part midpoint 300P1.

Further, the back-side end 150C of the abdomen-side flap 150 is arcuately formed and extends contiguously from the end 150B of the abdomen-side flap 150 in the diaper transverse direction to the leg-side end 120A.

A preferable structure of the abdomen-side flap 150 is now described with reference to FIGS. 9 and 10.

Figure 9:
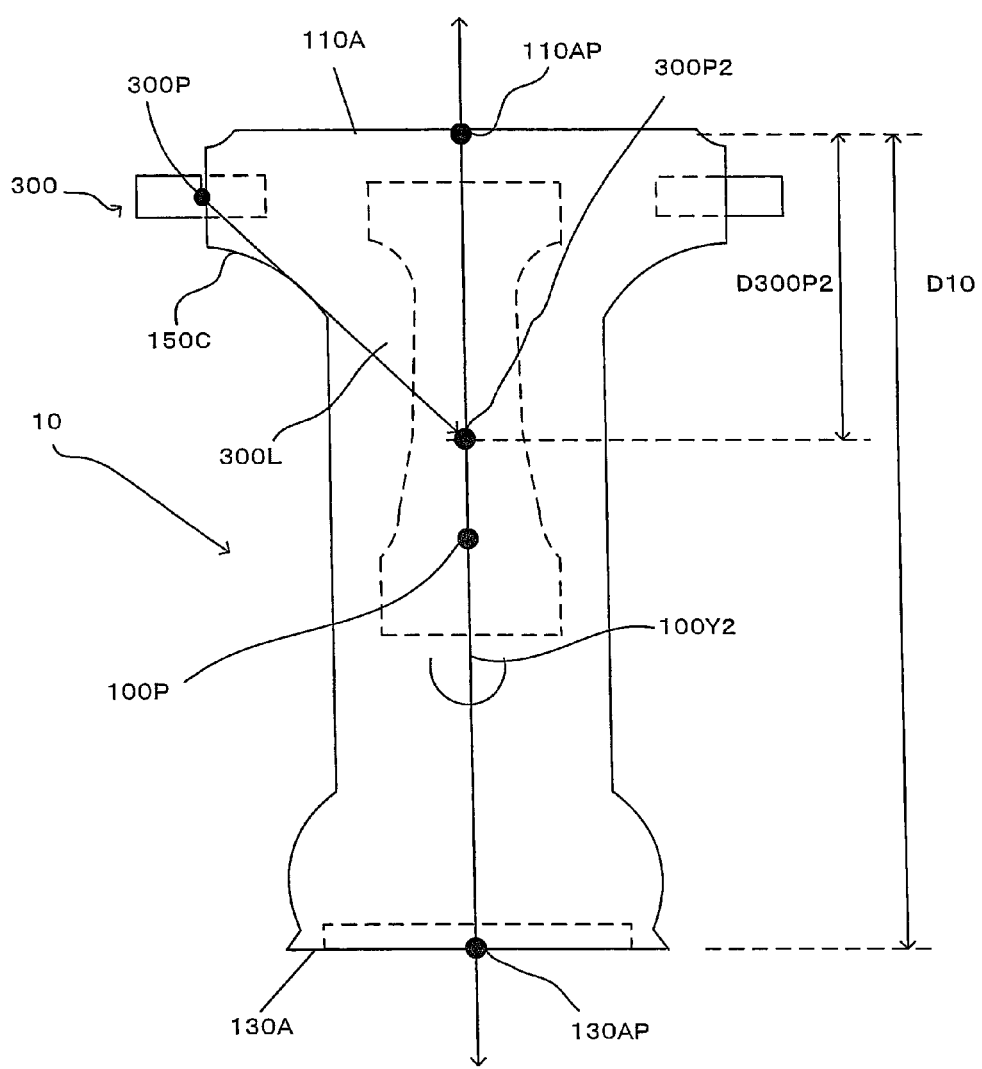
FIG. 9 is an explanatory drawing regarding to measurement for specifying a preferable structure of an abdomen-side flap.

In FIG. 9, a diaper longitudinal center line 100Y2 passes through the center of the disposable pet diaper 10 in the diaper transverse direction X. Specifically, the diaper longitudinal center line 100Y2 coincides with a line connecting an abdomen-side end center point 110AP on the center of the abdomen-side end 110A and a back-side end center point 130AP on the center of the back-side end 130A in the disposable pet diaper 10.

The length between the abdomen-side end 110A and the back-side end 130A on the diaper longitudinal center line 100Y2 is referred to as a diaper longitudinal length D1.

Further, a point which bisects the diaper longitudinal length D1 is referred to as a diaper center point 100P.

In providing the structure of the abdomen-side flap 150, the inventor focused on the relation between straight lines connecting the fastening part midpoint 300P1 of the fastening part 300 and the diaper longitudinal center line 100Y2 and the shape of the back-side end 150C of the abdomen-side flap 150.

Especially, the relation between a shortest straight-line distance 300L of a straight line passing the back-side end 150C of the abdomen-side flap 150, among the straight lines connecting the fastening part midpoint 300P1 of the fastening part 300 and the diaper longitudinal center line 100Y2, and a point of intersection of this straight line with the diaper longitudinal center line 100Y2 or a shortest line point 300P2 was focused on.

As a result of keen studies, it was found that the abdomen-side flap 150 has a suitable and advantageous structure when the shortest line point 300P2 is located on the side of the abdomen-side end 110A of the disposable pet diaper 10 beyond the diaper center point 100P.

Specifically, the position of the shortest line point 300P2 has a great influence on the shape of the back-side end 150C of the abdomen-side flap 150. As described above, the back-side end 150C is arcuate and extends from the end 150B of the abdomen-side flap 150 in the diaper transverse direction to the leg-side end 120A of the disposable pet diaper 10.

In this respect, assuming that the shortest line point 300P2 is located on the back-side end 130A side beyond the diaper center point, the position at which the back-side end 150C of the abdomen-side flap 150 meets the leg-side end 120A is located closer to the back-side end 130A than that in the present invention. As a result, the area of the abdomen-side flap 150 is increased. Therefore, when the disposable pet diaper 10 is put on the pet α, the abdomen-side flap 150 comes in contact with a leg α1 of the pet over a longer range.

Figure 10:
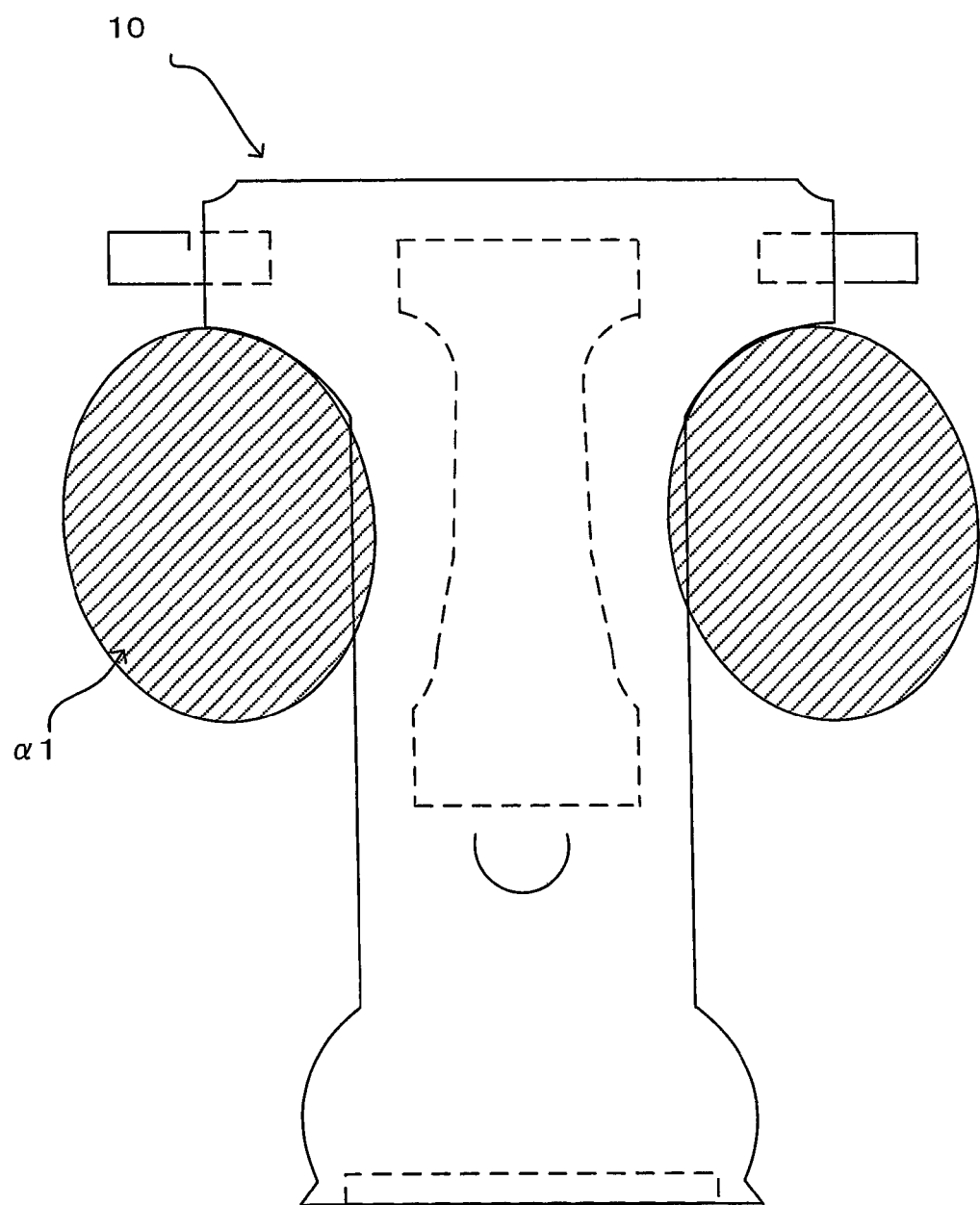
FIG. 10 is an explanatory drawing for illustrating the relation between the disposable diaper and legs of the pet

In the position of the shortest line point 300P2 according to this invention, however, as shown in FIG. 10, the area of the abdomen-side flap 150 can be reduced, and the length with which the back-side end 150C of the abdomen-side flap 150 comes in contact with the leg α1 of the pet can be reduced.

The disposable pet diaper 10 is available in various sizes corresponding to pets of various sizes. The pets here are limited to cats and dogs. In this case, when a measured length D2 or a distance between the shortest line point 300P2 and the abdomen-side end center point 110AP of the disposable pet diaper 10, is set to 170 to 250 mm, the suitable and advantageous abdomen-side flap 150 can be provided in the disposable pet diaper 10 of any size.

Further, the relation between the measured length D2 and the diaper longitudinal length D1 of the disposable pet diaper 10 was also considered. As a result, it was found that the suitable and advantageous abdomen-side flap 150 can be provided in the disposable pet diaper 10 of any size when the ratio of the measured length D2 to the diaper longitudinal length D1 is 45.5 to 50.0%.

In the disposable pet diaper 10, a leg stretchable elastic member 400 is provided in the absorbent-core non-arrangement region 170 between the end 100A in the diaper transverse direction and the absorbent core 200.

The leg stretchable elastic member 400 is arranged in a stretched state, and when using the disposable pet diaper 10, the leg stretchable elastic member 400 contracts and forms leg gathers 410 which are described below.

The leg stretchable elastic member 400 is arranged to extend from the abdomen-side end 110A to the back-side end 130A of the disposable pet diaper 10 in the diaper longitudinal direction Y.

Here, "to extend from the abdomen-side end 110A to the back-side end 130A" of the disposable pet diaper 10 does not only mean that the leg stretchable elastic member 400 continuously extends from the abdomen-side end 110A to the back-side end 130A. Specifically, the leg stretchable elastic member 400 may be arranged to extend with a distance from the abdomen-side end 110A or the back-side end 130A only if the abdomen-side end 110A or the back-side end 130A is acted upon by the contraction force of the leg stretchable elastic member 400 and the erected section 700 is formed.

The leg stretchable elastic member 400 is formed of synthetic or natural rubber thread.

The disposable pet diaper 10 has a waist stretchable elastic member 500. The waist stretchable elastic member 500 includes an abdomen-side waist stretchable elastic member 510 disposed in the absorbent-core non-arrangement region 170 between the diaper longitudinal end 110A in the diaper longitudinal direction and the abdomen-side end 210 of the absorbent core 200, and a back-side waist stretchable elastic member 520 disposed in the absorbent-core non-arrangement region 170 between the end 130A in the diaper longitudinal direction and the back-side end 220 of the absorbent core 200.

The waist stretchable elastic member 500 is arranged in a stretched state, and when using the disposable pet diaper 10, the waist stretchable elastic member 500 contracts and forms waist gathers 530.

The waist stretchable elastic member 500 and the leg stretchable elastic member 400 are arranged to overlap each other. Here, the term "overlap" as used in this embodiment does not only mean that the waist stretchable elastic member 500 and the leg stretchable elastic member 400 are in direct contact with each other. Specifically, the waist stretchable elastic member 500 and the leg stretchable elastic member 400 do not need to be in direct contact with each other only if their contraction forces act upon each other such that a contraction force intersecting region 180 is formed.

The waist stretchable elastic member 500 is formed of a urethane foamed sheet material.

The disposable pet diaper 10 has a leakproof sheet 800.

A leakproof sheet stretchable elastic member 600 is provided in a stretched state in the leakproof sheet 800.

The leakproof sheet 800 is disposed in a prescribed region extending from each of the ends 100A in the transverse direction of the disposable pet diaper 10 to the body 140B of the disposable pet diaper 10.

The leakproof sheet stretchable elastic member 600 is disposed within a space which is created by a folded part 810 of an inner end of the leakproof sheet 800 and extends in the diaper longitudinal direction Y.

Figure 11:
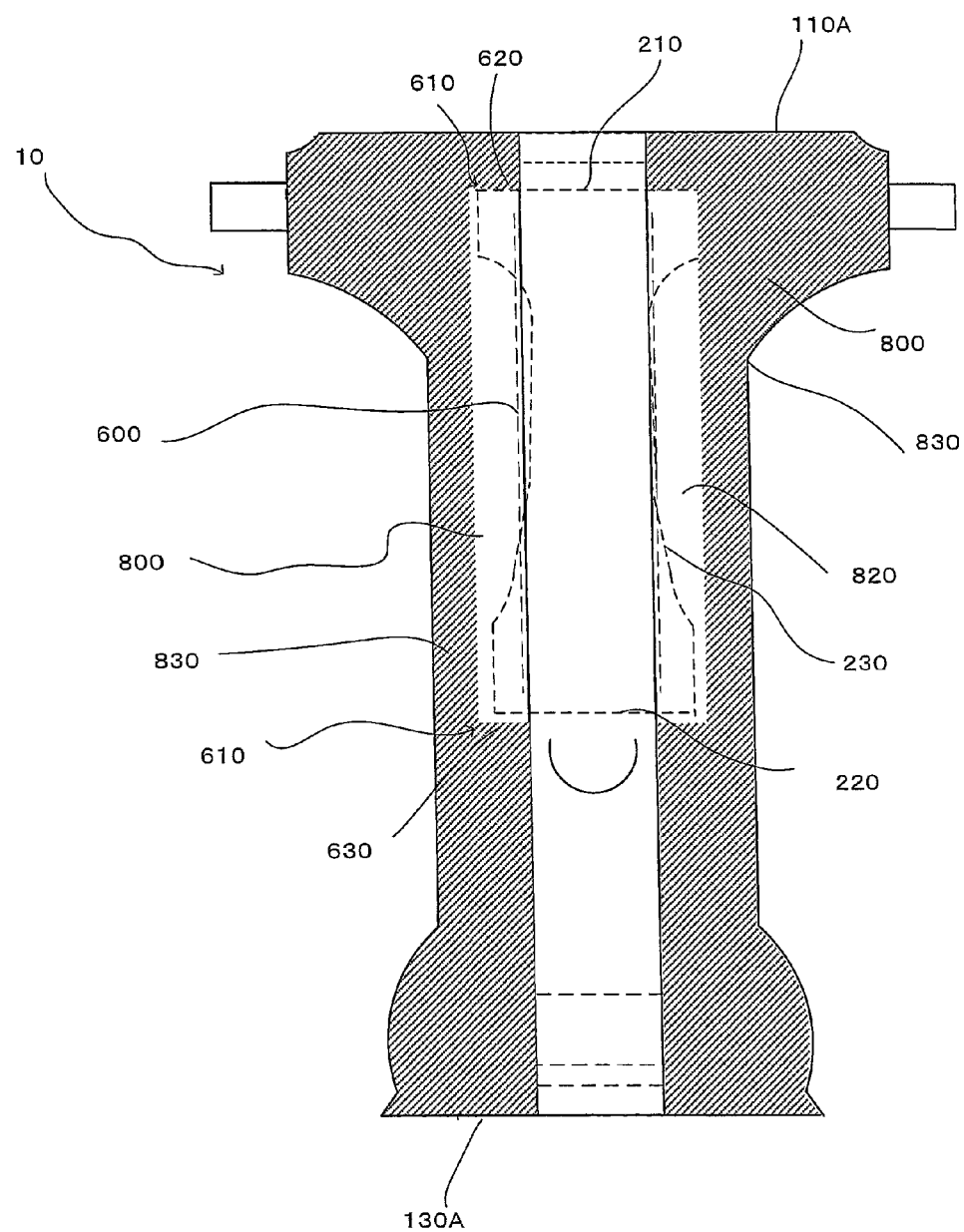
FIG. 11 is a plan view for showing a leakproof sheet fixed part in the unfolded state of the disposable diaper.

As shown in FIG. 11, the leakproof sheet 800 has a fixed part 830 which is fixed to other components (a liquid-permeable sheet 910, a liquid-resistant sheet 920, an outer sheet 930) of the disposable pet diaper 10 by an adhesive (not shown). In FIG. 11, the fixed part 830 is shown by hatching.

The fixed part 830 is not formed in a region of the leakproof sheet 800 which extends in the diaper longitudinal direction Y and overlaps with the end 230 of the absorbent core 200 in the diaper transverse direction X. This region not having the fixed part 830 is erected by contraction of the leakproof sheet stretchable elastic member 600 and forms a leakproof wall 820 which is described below. Further, leakproof gathers 840 are formed in the leakproof sheet 800 by contraction of the leakproof sheet stretchable elastic member 600.

The leakproof sheet stretchable elastic member 600 does not need to be provided along the whole length of the region (which forms the leakproof wall 820) not having the fixed part 830 in the diaper longitudinal direction Y. For example, it is sufficient to provide the leakproof sheet stretchable elastic member 600 only in part of the region of the leakproof wall 820 in the diaper longitudinal direction Y. Specifically, it is sufficient for the contraction force of the leakproof sheet stretchable elastic member 600 to act upon a part of the fixed part 830 on the both ends of the region of the leakproof wall 820 in the diaper longitudinal direction Y. Here, the part of the fixed part 830 on the both ends of the region of the leakproof wall 820 in the diaper longitudinal direction Y is referred to as a contraction force fixing part 610.

The contraction force fixing part 610 includes an abdomen-side contraction force fixing part 620 and a back-side contraction force fixing part 630.

The back-side contraction force fixing part 630 is provided between the back-side end 220 of the absorbent core 200 and the tail insertion opening 190. Specifically, by provision of this structure, the absorbent-core non-arrangement region 170 between the back-side end 220 of the absorbent core 200 and the tail insertion opening 190 is erected by contraction of the leakproof sheet stretchable elastic member 600 and forms the erected section 700.

Further, the abdomen-side contraction force fixing part 620 is provided between the abdomen-side end 210 of the absorbent core 200 and the abdomen-side end 110A of the disposable pet diaper 10. Specifically, by provision of this structure, as described below, the absorbent-core non-arrangement region 170 between the abdomen-side end 210 of the absorbent core 200 and the abdomen-side end 110A of the disposable pet diaper 10 is erected by contraction of the leakproof sheet stretchable elastic member 600 and forms the erected section 700.

The disposable pet diaper 10 includes the liquid-permeable sheet 910, the absorbent core 200, the liquid-resistant sheet 920, the outer sheet 930 and the leakproof sheet 800.

Figure 12:
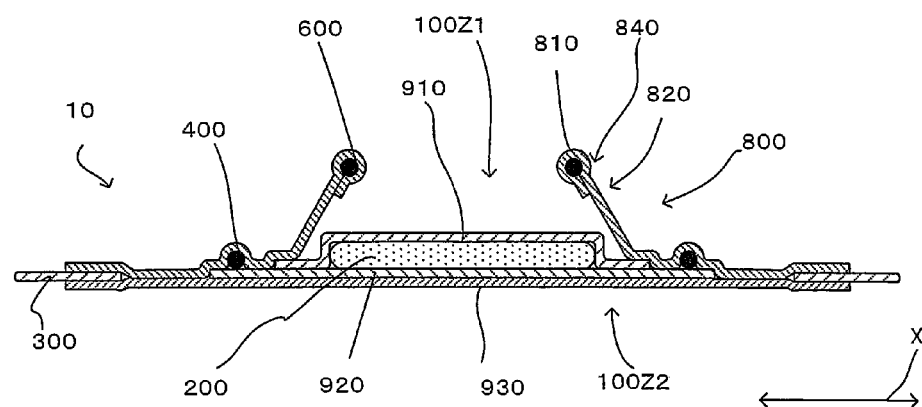
FIG. 12 is a sectional view taken along line A-A in FIG. 1.
Figure 13:
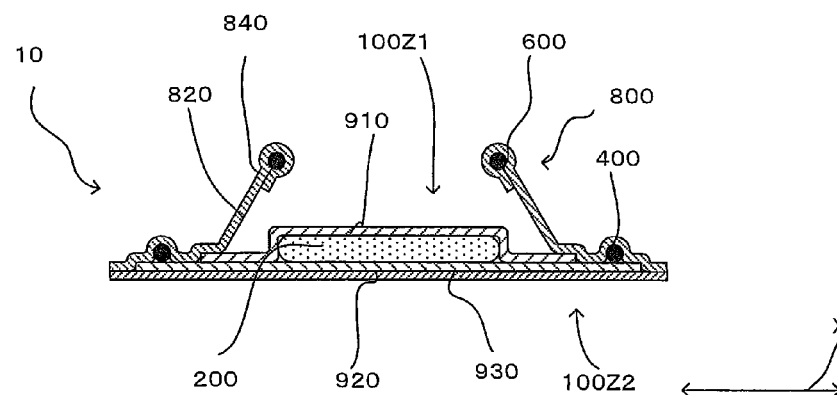
FIG. 13 is a sectional view taken along line B-B in FIG. 1.
Figure 14:
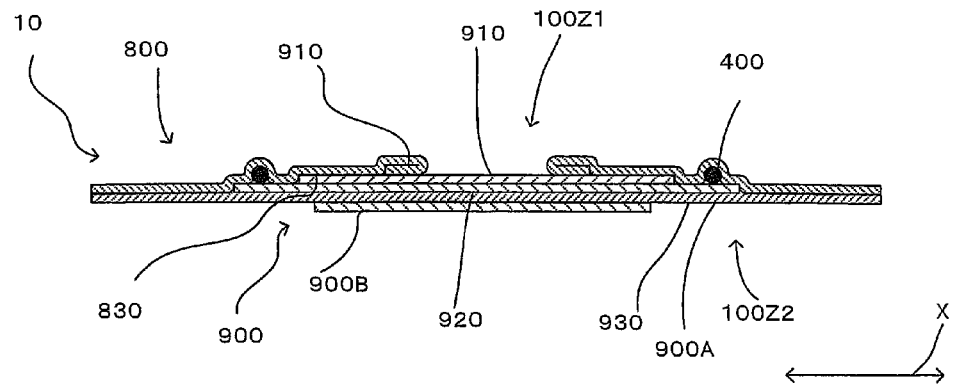
FIG. 14 is a sectional view taken along line C-C in FIG. 1.

As shown in FIGS. 12 to 14, the liquid-permeable sheet 910 is disposed on the inside surface 100Z1 side of the disposable pet diaper 10. The absorbent core 200 is disposed between the liquid-permeable sheet 910 and the liquid-resistant sheet 920. The outer sheet 930 is disposed on the outside surface 100Z2 side of the liquid-resistant sheet 920. The leakproof sheet 800 is disposed over the liquid-permeable sheet 910, the liquid-resistant sheet 920 and the outer sheet 930 in the diaper transverse direction X. As a result, the abdomen-side flap 150 and the back-side flap 160 are formed by the leakproof sheet 800 and the outer sheet 930.

The leg stretchable elastic member 400 is disposed between the leakproof sheet 800 and the liquid-resistant sheet 920.

The leakproof sheet stretchable elastic member 600 is disposed in the space inside the folded part 810 formed on the end of the leakproof sheet 800.

As shown in FIG. 12, the fastening part 300 is disposed between the leakproof sheet 800 and the outer sheet 930.

As shown in FIGS. 12 and 13, the leakproof sheet 800 not having the fixed part 830 is erected by contraction of the leakproof sheet stretchable elastic member 600 and forms the leakproof wall 820. At this time, a large number of creases or the leakproof gathers 840 are formed in the leakproof sheet 800.

As shown in FIG. 14, the second fastening region 900B of the fastening region 900 is provided on the outside surface 100Z2 of the outer sheet 930.

The waist stretchable elastic member 500, not shown, is disposed between the liquid-permeable sheet 910 and the liquid-resistant sheet 920.

The liquid-permeable sheet 910, the liquid-resistant sheet 920, the outer sheet 930 and the leakproof sheet 800 are formed of nonwoven fabric. The nonwoven fabric can be selected from those manufactured by spun lacing, needle punching, melt blowing, thermal bonding, spun bonding or chemical bonding.

An adhesive, not shown, is used to fix the liquid-permeable sheet 910, the liquid-resistant sheet 920, the outer sheet 930 and the leakproof sheet 800 with each other and to fix the leg stretchable elastic member 400, the leakproof sheet stretchable elastic member 600 and the waist stretchable elastic member 500. A hot-melt adhesive is preferably used as the adhesive, but other adhesives such as acrylic adhesive and rubber adhesive can also be used.

The adhesive is preferably applied in any one of spiral, wave, dot and stripe patterns.

Figure 15:
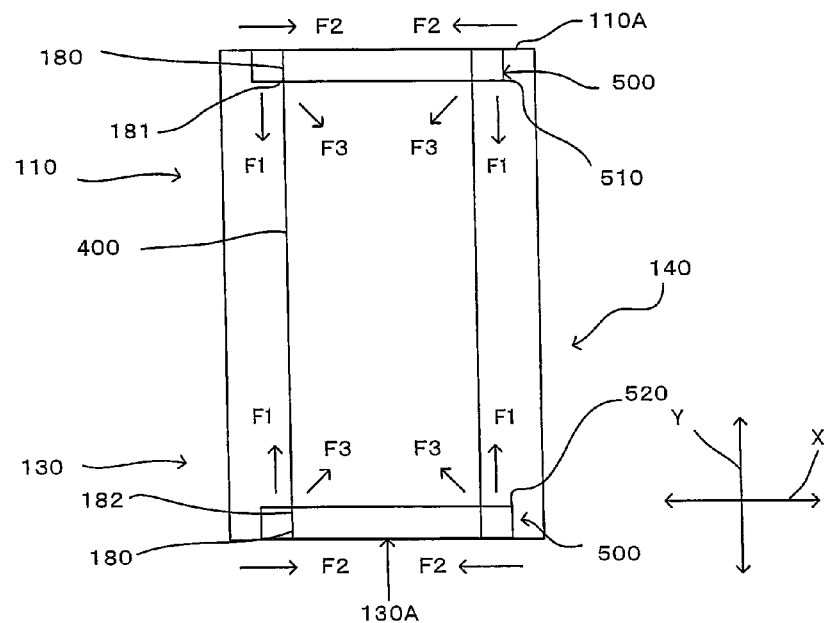
FIG. 15 is an explanatory drawing for illustrating the structures of a leg stretchable elastic member and a waist stretchable elastic member.
Figure 16:
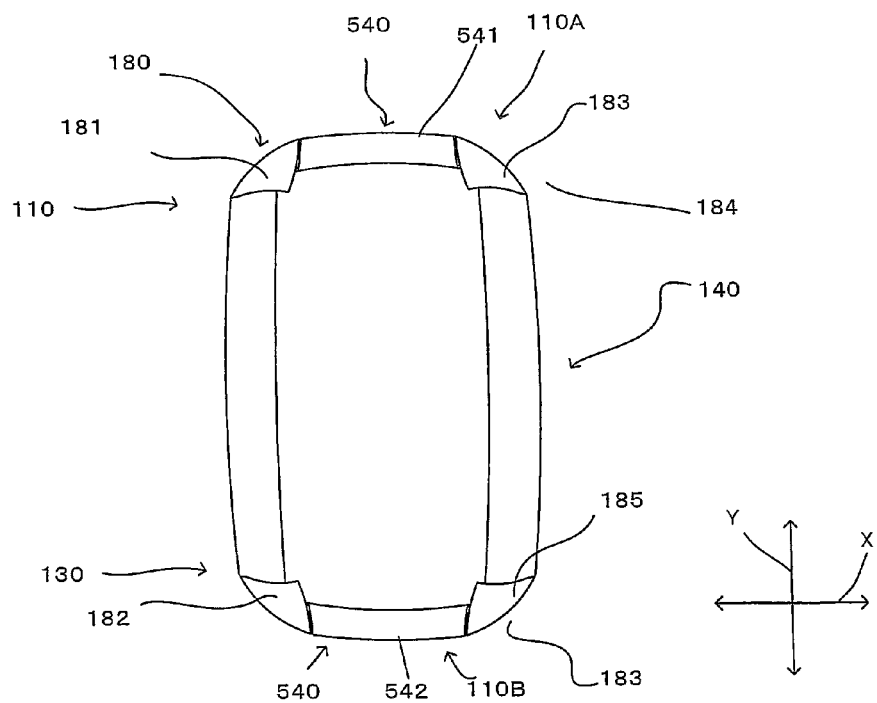
FIG. 16 is an explanatory drawing for illustrating the operations of the leg stretchable elastic member and the waist stretchable elastic member.

Next, the relation between the contraction forces of the leg stretchable elastic member 400 and the waist stretchable elastic member 500 is described with reference to FIGS. 15 and 16. In FIGS. 15 and 16, for convenience of explanation, the abdomen-side flaps 150 and the back-side flaps 160 are not shown and only the body 140B is shown.

As shown in FIG. 15, the leg stretchable elastic member 400 contracts inward from the ends in the diaper longitudinal direction Y. Specifically, contraction force F1 of the leg stretchable elastic member 400 acts inward in the diaper longitudinal direction Y.

The waist stretchable elastic member 500 contracts inward from the ends in the diaper transverse direction X. Specifically, contraction force F2 of the waist stretchable elastic member 500 acts inward in the diaper transverse direction X.

The contraction force intersecting region 180 is a region in which the contraction force F1 of the leg stretchable elastic member 400 and the contraction force F2 of the waist stretchable elastic member 500 intersect with each other. Therefore, contraction force F3 of the contraction force intersecting region 180 acts inward in a direction crossing the diaper longitudinal direction Y and the diaper transverse direction X.

The contraction force intersecting region 180 includes a first contraction force intersecting region 181 formed toward the abdomen-side end 110A of the disposable pet diaper 10 and a second contraction force intersecting region 182 formed toward the back-side end 130A.

As a result, as shown in FIG. 16, a first curved part 540 is formed in the abdomen-side end 110A and the back-side end 130A of the disposable pet diaper 10 and bulges outward in a direction from the inside surface 100Z1 to the outside surface 100Z2 of the disposable pet diaper 10 by the contraction force F2 of the waist stretchable elastic member 500.

The first curved part 540 includes a first abdomen-side curved part 541 formed in the abdomen-side end 110A of the disposable pet diaper 10 and a first back-side curved part 542 formed in the back-side end 130A of the disposable pet diaper 10.

Further, a second curved part 183 is formed in the contraction force intersecting region 180 and curved in the direction of the inside surface 100Z1 of the disposable pet diaper 10 by the contraction force F3 acting on the contraction force intersecting region 180.

The second curved part 183 includes a second abdomen-side curved part 184 formed in the first contraction force intersecting region 181 and a second back-side curved part 185 formed in the second contraction force intersecting region 182.

Figure 17:
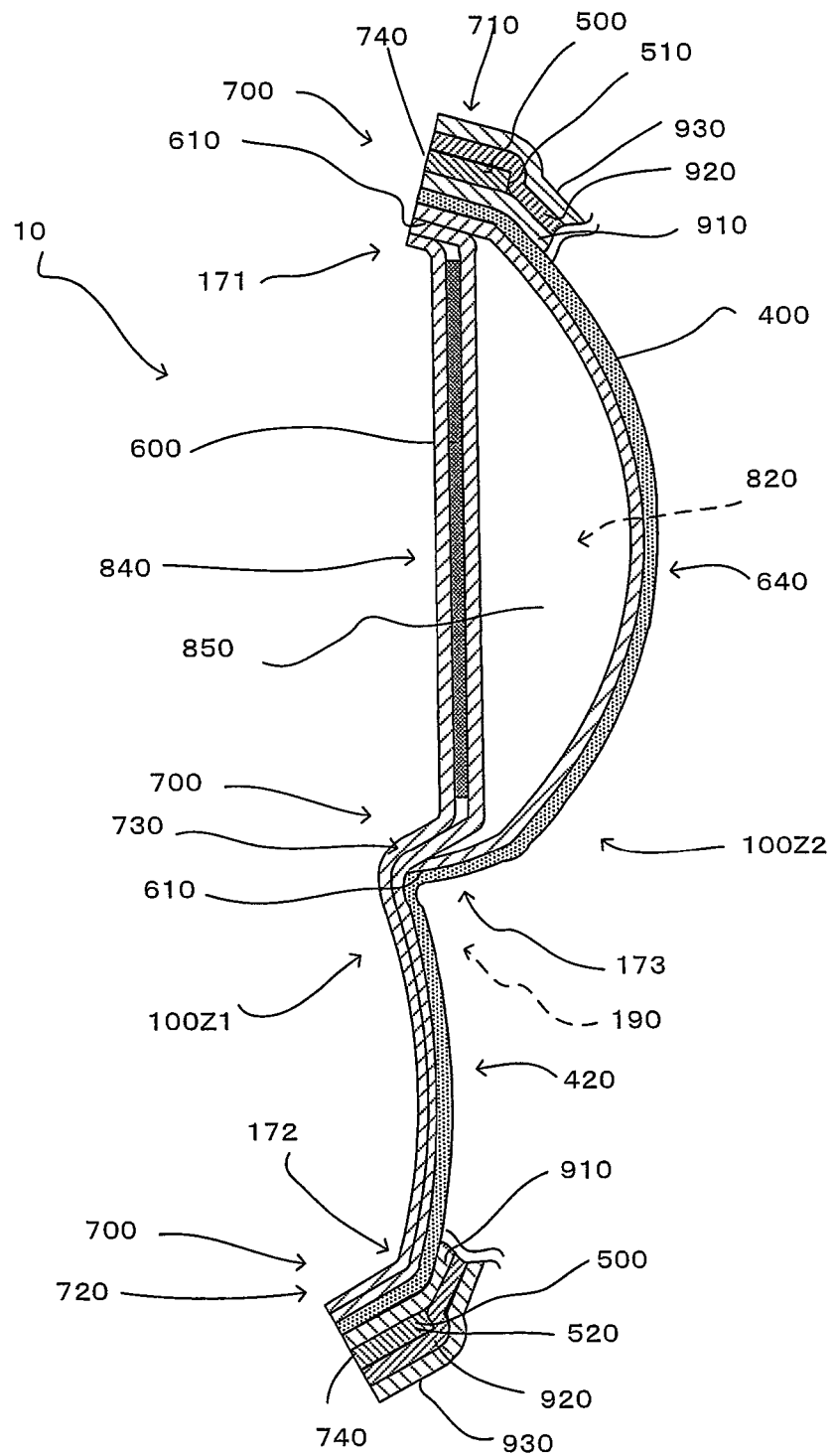
FIG. 17 is an explanatory drawing in a sectional view taken along line D-D in FIG. 1.

Now, the state in which the leg stretchable elastic member 400 and the leakproof sheet stretchable elastic member 600 are contracted is described with reference to FIG. 17. FIG. 17 is a sectional view taken along line D-D in FIG. 1, but, for convenience of explanation, part of the liquid-permeable sheet 910, the liquid-resistant sheet 920 and the outer sheet 930 and the whole of the absorbent core 200 and the fastening region 900 are not shown.

In FIG. 17, the leg stretchable elastic member 400 and the leakproof sheet stretchable elastic member 600 are contracted. As a result, the erected section 700 is formed by the contraction forces of the leg stretchable elastic member 400 and the leakproof sheet stretchable elastic member 600. Specifically, each of the abdomen-side erected region 171, the back-side erected region 172 and the crotch-side erected region 173 in the absorbent-core non-arrangement region 170 is erected and forms the erected section 700.

The erected section 700 includes an abdomen-side erected section 710, a back-side erected section 720 and a crotch-side erected section 730.

The abdomen-side erected region 171 is erected by contraction of the leg stretchable elastic member 400 and forms the abdomen-side erected section 710.

The end of the leg stretchable elastic member 400 is arranged closer to the abdomen-side end 110A of the disposable pet diaper 10 than the end of the leakproof sheet stretchable elastic member 600. Therefore, the abdomen-side erected section 710 more strongly receives the influence of the contraction force of the leg stretchable elastic member 400 than the influence of the contraction force of the leakproof sheet stretchable elastic member 600. Specifically, the abdomen-side fixing part 620 of the contraction force fixing part 610 is moved by the contraction force of the leakproof sheet stretchable elastic member 600, which causes erection of the abdomen-side erected region 171. Therefore, the leakproof sheet stretchable elastic member 600 also forms the abdomen-side erected section 710.

Further, in this invention, as used herein, the term "erect" to form the erected section 700 means that the absorbent-core non-arrangement region 170 deforms by the contraction force of one of the stretchable elastic members or by a combination of the contraction forces of two or more of the stretchable elastic members.

The back-side erected region 172 is erected by contraction of the leg stretchable elastic member 400 and forms the back-side erected section 720.

The leg stretchable elastic member 400 is overlapped with the waist stretchable elastic member 500. Specifically, the both ends of the leg stretchable elastic member 400 are overlapped with the abdomen-side waist stretchable elastic member 510 and the back-side waist stretchable elastic member 520.

The waist stretchable elastic member 500 is arranged having a prescribed length in the diaper transverse direction. Therefore, the abdomen-side erected section 710 and the back-side erected section 720 erect the abdomen-side waist stretchable elastic member 510 and the back-side waist stretchable elastic member 520, respectively. Thus, the abdomen-side erected region 171 and the back-side erected region 172 are held in the stable erected state. Specifically, the abdomen-side waist stretchable elastic member 510 and the back-side waist stretchable elastic member 520 are provided as an erection sheet 740 to ensure the erected state of the erected section 700.

When the back-side fixing part 630 of the contraction force fixing part 610 is moved by contraction of the leakproof sheet stretchable elastic member 600, the crotch-side erected region 173 is erected and forms the crotch-side erected section 730.

Further, as described above, the leakproof wall 820 is formed by contraction of the leakproof sheet stretchable elastic member 600. A space surrounded by the leakproof wall 820, the abdomen-side erected section 710, the crotch-side erected section 730 and the absorbent core (not shown in FIG. 17) forms an excrement storage space 850.

A third curved part 640 is formed in a region extending from the abdomen-side end 110A to the tail insertion opening 190 in the disposable pet diaper 10 and bulges in a direction from the inside surface 100Z1 to the outside surface 100Z2 of the disposable pet diaper 10 by the contraction force F1 of the leg stretchable elastic member 400 and the leakproof sheet stretchable elastic member 600.

A fourth curved part 420 is formed in a region extending from the tail insertion opening 190 to the back-side end 130A in the disposable pet diaper 10 and bulges in a direction from the inside surface 100Z1 to the outside surface 100Z2 of the disposable pet diaper 10 mainly by the contraction force F1 of the leg stretchable elastic member 400.

Figure 18:
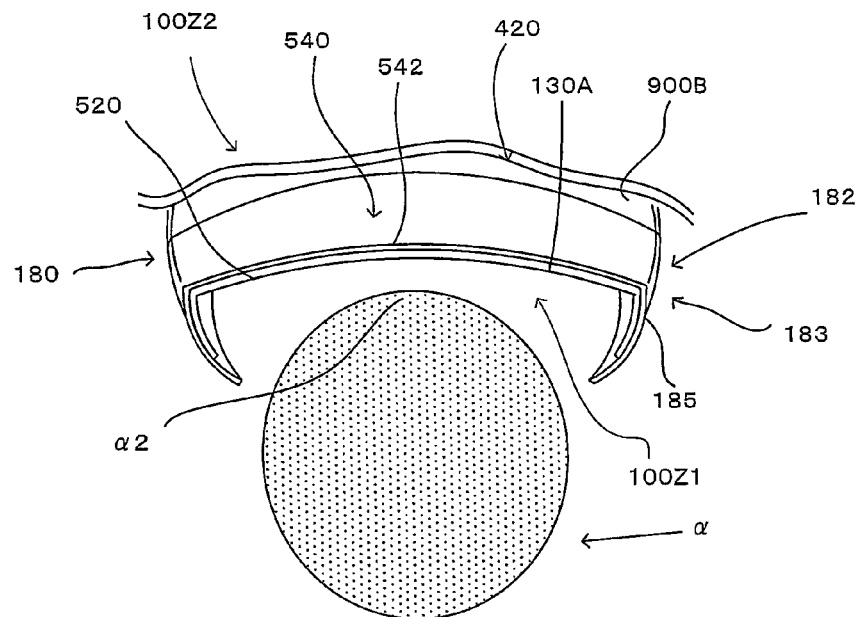
FIG. 18 is an explanatory drawing regarding to a backside waist area in putting the disposable diaper on a pet.
Figure 19:
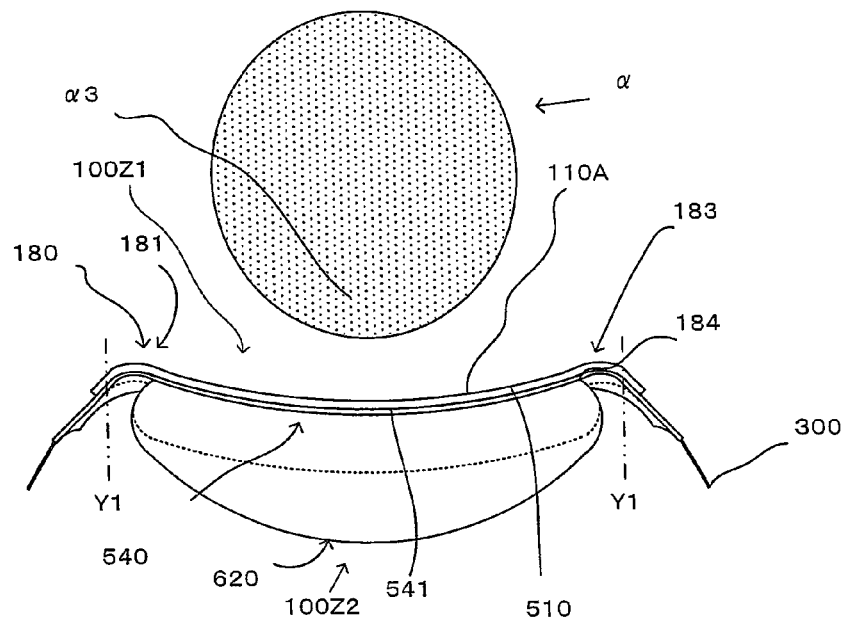
FIG. 19 is an explanatory drawing regarding to an abdomen-side waist area in putting the disposable diaper on a pet.

Next, the operation of putting the disposable pet diaper 10 on a pet is explained with reference to FIGS. 18 to 20. First, a user takes the disposable pet diaper 10 out of a package. In most cases, in the package, the abdomen-side flaps 150 and the back-side flaps 160 of the disposable pet diaper 10 are folded inward, and the disposable pet diaper 10 itself is folded, for example, into two or three.

When using the disposable pet diaper 10, the user unfolds the folded structure. At this time, the leg stretchable elastic member 400, the waist stretchable elastic member 500 and the leakproof sheet stretchable elastic member 600 contract. As a result, the erected section 700 including the abdomen-side erected section 710, the back-side erected section 720 and the crotch-side erected section 730 is formed, and the leakproof wall 820 is formed. Further, the first curved part 540, the second curved part 183, the third curved part 640 and the fourth curved part 420 are formed, and the leg gathers 410, the waist gathers 530 and the leakproof gathers 840 are formed. The shape of the disposable pet diaper 10 is stabilized by contraction of the leg stretchable elastic member 400, the waist stretchable elastic member 500 and the leakproof sheet stretchable elastic member 600.

Next, the user inserts the tail of the pet α through the tail insertion opening 190 of the disposable pet diaper 10.

Then the user covers the crotch and the abdomen of the pet α with the crotch area 120 and the abdomen-side waist area 110, while the back-side waist area 130 is fitted closely to the back of the pet α. Then the free end 310 of the fastening part 300 is fastened to the fastening region 900. Thus, the disposable pet diaper 10 is put on the pet α.

These matters related to putting the disposable pet diaper 10 on the pet α is an example embodiment that corresponds to the feature that "when the disposable diaper is put on the pet, the crotch area and the abdomen-side waist area cover a crotch and an abdomen of the pet, while the back-side waist area is closely fitted to a back of the pet, and the fastening part is fastened to the fastening region" according to this invention.

The state of the disposable pet diaper 10 in fitting the back-side waist area 130 to the back of the pet α is explained with reference to FIG. 18.

The first curved part 540 bulging outward in the direction of the diaper outside surface 100Z2 is already formed in the back-side end 130A. Further, a region extending from the back-side end 130A to the tail insertion opening 190 is maintained in a stable shape by the fourth curved part 420. The back-side flap 160 is curved in the direction of the inside surface 100Z1 of the disposable pet diaper 10 together with the second contraction force intersecting region 182 by the second curved part 183.

Thus, the user can easily place the back-side end 130A along a curve of the back of the pet α.

Further, the back-side end 130A has a low possibility of turning up.

The state of the disposable pet diaper 10 in covering the crotch and the abdomen of the pet α with the crotch area 120 and the abdomen-side waist area 110 and fastening the free end 310 of the fastening part 300 to the fastening region 900, is explained with reference to FIG. 19.

The first curved part 540 bulging outward in the direction of the diaper outside surface 100Z2 is already formed in the abdomen-side end 110A. Further, a region extending from the abdomen-side end 110A to the tail insertion opening 190 is maintained in a stable shape by the third curved part 640.

The abdomen-side flap 150 is curved together with the first contraction force intersecting region 181 in the direction of the inside surface 100Z1 of the disposable pet diaper 10 by the second curved part 183. In the abdomen-side flap 150 having the fastening part 300, the end 150B in the transverse direction is heavier than a boundary part of the abdomen-side flap 150 with the body 140B. Therefore, the boundary part of the abdomen-side flap 150 with the body 140B is curved in the direction of the inside surface 100Z1 together with the second curved part 183, while the end 150B of the abdomen-side flap 150 in the transverse direction is curved in the direction of the outside surface 100Z2 by its own weight. As a result, the fastening part 300 is supported by the abdomen-side flap 150 without hanging straight down.

Thus, the user can easily set the abdomen-side end 110A onto a curve of the abdomen of the pet α.

Further, the abdomen-side end 110A has a low possibility of turning up.

Further, the user can easily grab the fastening part 300.

Furthermore, when the user moves the fastening part 300 toward the fastening region 900, the fastening part 300 receives the influence of the first contraction force intersecting region 181. Therefore, wherever the user moves the fastening part 300, the contraction force acts upon the fastening part 300. As a result, the user can easily move the fastening part 300 onto a desired position of the fastening region 900.

Figure 20:
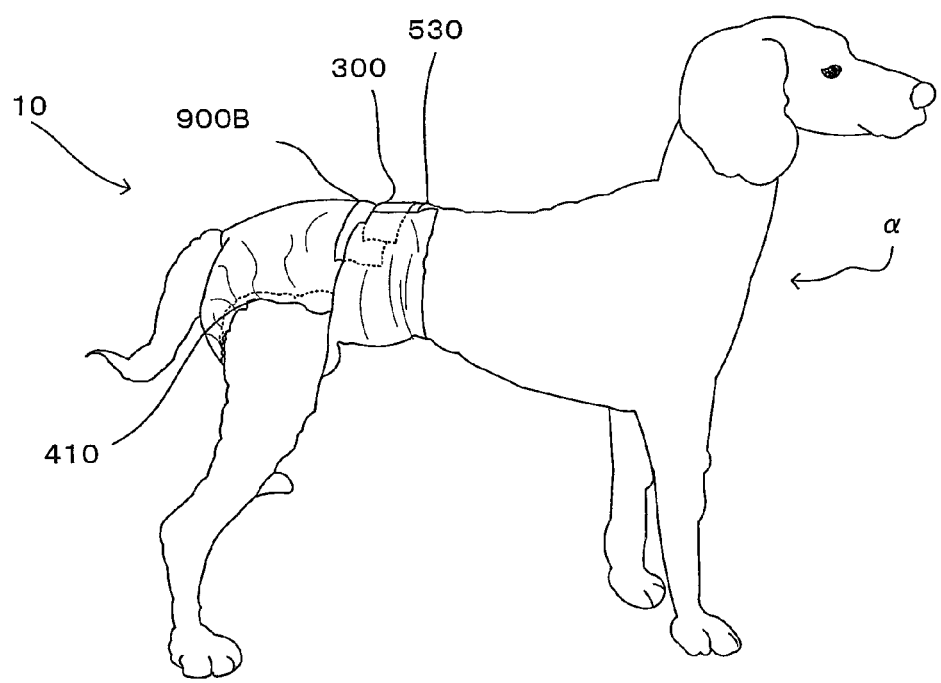
FIG. 20 is an explanatory drawing for illustrating the state of the disposable diaper worn by a pet.

FIG. 20 is a drawing for illustrating the state of the disposable pet diaper 10 worn by the pet α.

Even after the disposable pet diaper 10 has been put on the pet, the leg stretchable elastic member 400, the waist stretchable elastic member 500 and the leakproof sheet stretchable elastic member 600 are maintained in the contracted state. Therefore, the erected section 700 including the abdomen-side erected section 710, the back-side erected section 720 and the crotch-side erected section 730 is maintained in the erected state. The leakproof wall 820 is also maintained. Further, the first curved part 540, the second curved part 183, the third curved part 640 and the fourth curved part 420 are maintained in the curved state. The leg gathers 410, the waist gathers 530 and the leakproof gathers 840 are maintained.

When the pet α excretes, excrement is held within the excrement storage space 850. When the excrement is urine, it is absorbed by the absorbent core 200. When the excrement is feces, part of feces is absorbed by the absorbent core 200 and the rest is held within the excrement storage space 850.

Whether the excrement is urine or feces, the weight of the absorbent core 200 is received in the fastening part longitudinal direction 300X in the free part 310 of the fastening part 300.

This is an example embodiment that corresponds to the feature that "the weight of the absorbent core after excretion is received in the longitudinal direction of the fastening part while the disposable diaper is worn by the pet" according to this invention.

In order to remove the disposable pet diaper 10 from the pet α, the fastening part 300 is detached from the fastening region 900, and then the disposable pet diaper 10 is pulled off through the tail insertion opening 190 and disposed of.

In the process of detaching the fastening part 300 from the fastening region 900 and pulling off the disposable pet diaper 10 through the tail insertion opening 190, the abdomen-side end 110A is turned obliquely downward from the pet α. Even at this time, the risk of falling of feces can be reduced by the abdomen-side erected section 710.

Second to twenty-ninth embodiments of the present invention are now described with reference to FIGS. 21 to 50. In the description of the second to twenty-ninth embodiments, components which are identical to those in the first embodiment are not described in detail and their reference numerals are omitted.

Second Embodiment

Figure 21:
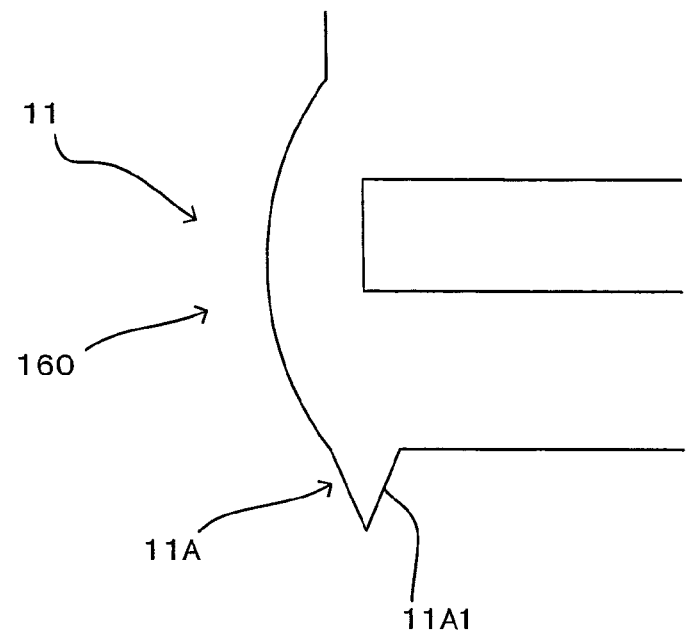
FIG. 21 is an explanatory drawing for illustrating a disposable diaper for pets according to a second embodiment of the present invention.

The second embodiment of the present invention is explained with reference to FIG. 21. A disposable pet diaper 11 according to the second embodiment is different from the disposable pet diaper 10 of the first embodiment in that an identification region 11A is formed as a second extended identification region 11A1.

Specifically, the identification region 11A extends from the longitudinal end of the back-side flap 160 of the disposable pet diaper 11 in the diaper longitudinal direction.

This relation between the identification region 11A and the second extended identification region 11A1 is an example embodiment that corresponds to the feature that "the identification region comprises a second extended identification region extending from the back-side flap in the longitudinal direction" according to this invention.

By providing the identification region 11A as the second extended identification region 11A1, whether the back-side flap 160 is creased or not can be confirmed when the disposable pet diaper 11 is put on a pet. Specifically, if the second extended identification region 11A1 is visible when the disposable pet diaper 11 is put on a pet, it is identified that the back-side flap 160 is not creased. On the other hand, if the second extended identification region 11A1 is not visible or is creased, it is identified that the back-side flap 160 is creased.

Third Embodiment

Figure 22:
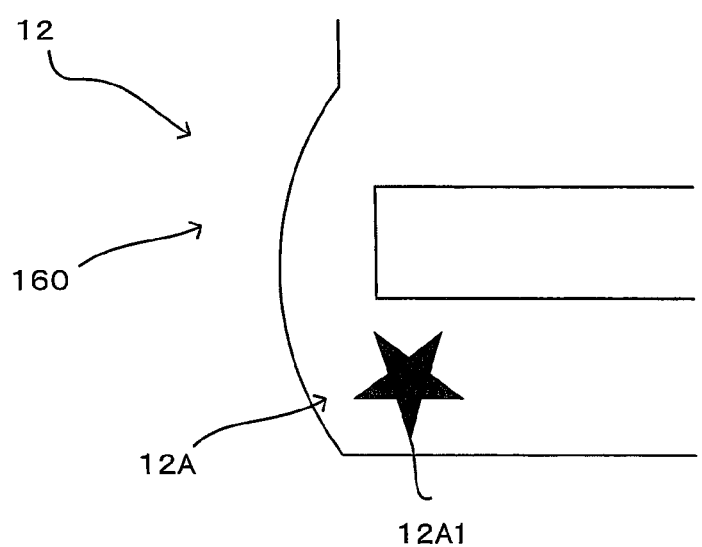
FIG. 22 is an explanatory drawing for illustrating a disposable diaper for pets according to a third embodiment of the present invention.

The third embodiment of the present invention is explained with reference to FIG. 22. A disposable pet diaper 12 according to the third embodiment is different from the disposable pet diaper 10 of the first embodiment in that an identification region 12A is formed as a colored identification region 12A1 which is differently colored from the other region of the back-side flap 160.

This relation between the identification region 12A and the colored identification region 12A1 is an example embodiment that corresponds to the feature that "the identification region comprises a colored identification region that is differently colored from the other region of the back-side flap" according to this invention.

By providing the identification region 12A as the colored identification region 12A1, whether the back-side flap 160 is creased or not can be confirmed when the disposable pet diaper 12 is put on a pet. Specifically, if the colored identification region 12A1 is visible when the disposable pet diaper 12 is put on a pet, it is identified that the back-side flap 160 is not creased. On the other hand, if the colored identification region 12A1 is not visible or is creased, it is identified that the back-side flap 160 is creased.

Fourth Embodiment

Figure 23:
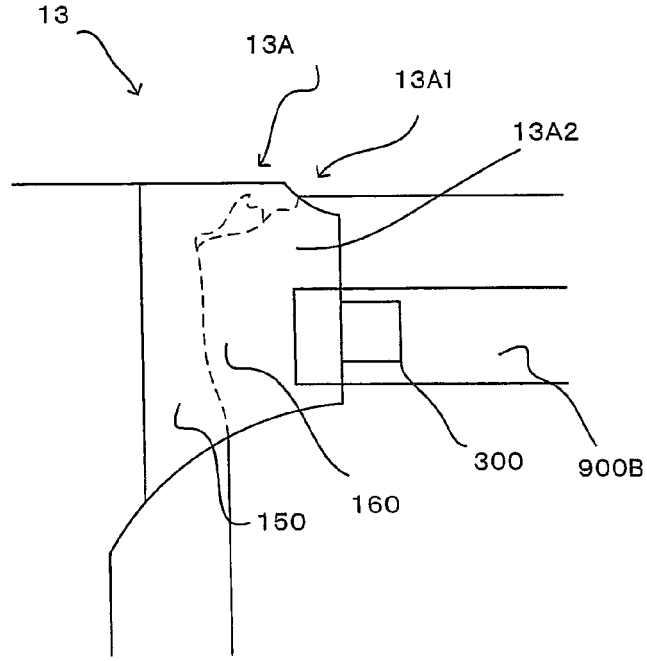
FIG. 23 is an explanatory drawing for illustrating a disposable diaper for pets according to a fourth embodiment of the present invention.

The fourth embodiment of the present invention is explained with reference to FIG. 23. A disposable pet diaper 13 according to the fourth embodiment is different from the disposable pet diaper 10 of the first embodiment in that an identification region 13A is formed in the abdomen-side flap 150.

This is an example embodiment that corresponds to the feature that "the identification region is formed in the abdomen-side flap" according to this invention.

The identification region 13A formed in the abdomen-side flap 150 forms a visible region 13A1 for checking the state of the back-side flap 160.

The visible region 13A1 is an example embodiment that corresponds to the feature that "the identification region comprises a visible region that is formed in the abdomen-side flap for checking the state of the back-side flap" according to this invention.

In the fourth embodiment, the visible region 13A1 is formed by a light transmissive identification region 13A2 which is capable of transmitting light.

The light transmissive identification region 13A2 is an example embodiment that corresponds to the feature that "the visible region comprises a light transmissive identification region which is capable of transmitting light" according to this invention.

Specifically, the light transmissive identification region 13A2 is obtained by forming the abdomen-side flap 150 of a known nonwoven fabric or film which is capable of transmitting light. It needs to have a light transmitting capability enough to make the back-side flap 160 visible through the abdomen-side flap 150 when the abdomen-side flap 150 is put on the back-side flap 160.

By providing the identification region 13A as the visible region 13A1 in the form of the light transmissive identification region 13A2, whether the back-side flap 160 is creased or not can be confirmed when the disposable pet diaper 13 is put on a pet. Specifically, the state of the back-side flap 160 can be visually checked through the light transmissive identification region 13A2 when the disposable pet diaper 13 is put on a pet.

Fifth Embodiment

Figure 24:
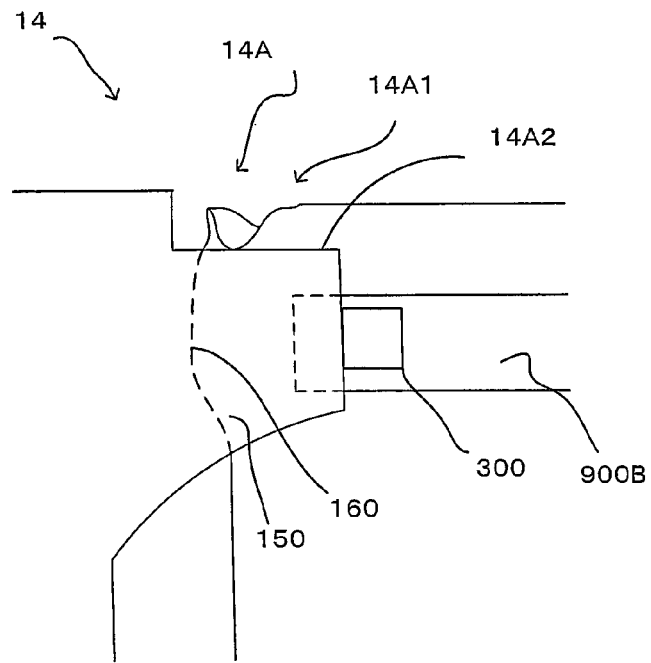
FIG. 24 is an explanatory drawing for illustrating a disposable diaper for pets according to a fifth embodiment of the present invention.

The fifth embodiment of the present invention is explained with reference to FIG. 24. A disposable pet diaper 14 according to the fifth embodiment is different from the disposable pet diaper 10 of the first embodiment in that an identification region 14A in the form of a visible region 14A1 is formed by a cutout identification region 14A2 that is formed by cutting out an abdomen-side end portion of the abdomen-side flap 150.

The cutout identification region 14A2 is an example embodiment that corresponds to the feature that "the visible region comprises a cutout identification region formed by cutting out an abdomen-side end portion of the abdomen-side flap" according to this invention.

By providing the identification region 14A as the visible region 14A1 in the form of the cutout identification region 14A2, whether the back-side flap 160 is creased or not can be confirmed when the disposable pet diaper 14 is put on a pet. Specifically, the state of the back-side flap 160 can be visually checked through the cutout identification region 14A2 when the disposable pet diaper 14 is put on a pet.

Sixth Embodiment

Figure 25:
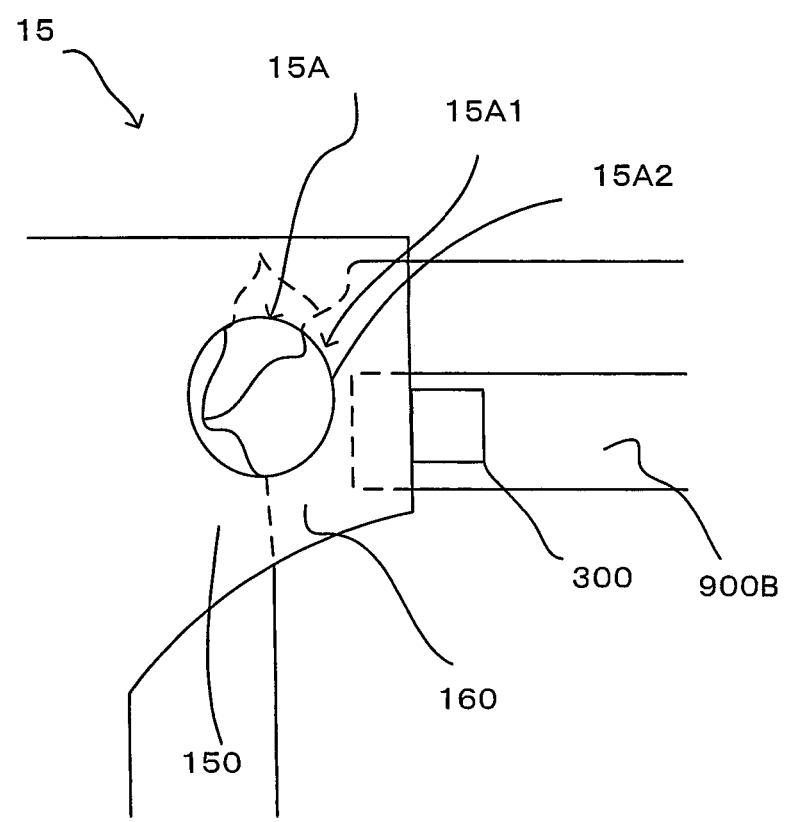
FIG. 25 is an explanatory drawing for illustrating a disposable diaper for pets according to a sixth embodiment of the present invention.

The sixth embodiment of the present invention is explained with reference to FIG. 25. A disposable pet diaper 15 according to the sixth embodiment is different from the disposable pet diaper 10 of the first embodiment in that an identification region 15A in the form of a visible region 15A1 is formed by a first open identification region 15A2 that is formed by providing an opening in the abdomen-side flap 160.

The first open identification region 15A2 is an example embodiment that corresponds to the feature that "the visible region comprises a first open identification region formed by an opening in the abdomen-side flap" according to this invention.

By providing the identification region 15A as the visible region 15A1 in the form of the first open identification region 15A2, whether the back-side flap 160 is creased or not can be confirmed when the disposable pet diaper 15 is put on a pet. Specifically, the state of the back-side flap 160 can be visually checked through the first open identification region 15A2 when the disposable pet diaper 15 is put on a pet.

Seventh Embodiment

Figure 26:
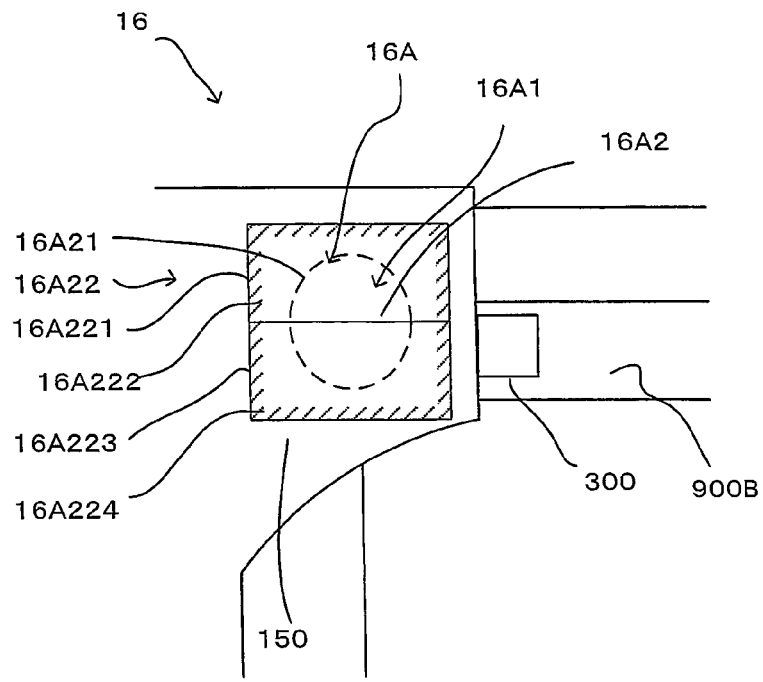
FIG. 26 is an explanatory drawing for illustrating a disposable diaper for pets according to a seventh embodiment of the present invention.

The seventh embodiment of the present invention is explained with reference to FIG. 26. A disposable pet diaper 16 according to the seventh embodiment is different from the disposable pet diaper 10 of the first embodiment in that an identification region 16A in the form of a visible region 16A1 has a second open identification region 16A2 formed by an opening in the abdomen-side flap 150, and a cover region 16A22 that is configured to cover the second open identification region 16A2 and to be freely opened and closed with respect to the second open identification region 16A2.

The second open identification region 16A2 and the cover region 16A22 are example embodiments that correspond to the feature that "the visible region comprises a second open identification region formed by an opening in the abdomen-side flap, and a cover region configured to cover the second open identification region and to be freely opened and closed with respect to the second open identification region" according to this invention.

The second open identification region 16A2 is formed by an opening 16A21 in the abdomen-side flap 150.

The cover region 16A22 has a first cover part 16A221 and a second cover part 16A223. The first cover part 16A221 and the second cover part 16A223 are arranged side by side so as to cover the opening 16A21. The first cover part 16A221 and the second cover part 16A223 are opposed to each other at the center of the opening 16A21. Ends of the first cover part 16A221 other than the end opposed to the second cover part 16A223 form a first bonded part 16A222 connected to the outer sheet by an adhesive. Ends of the second cover part 16A223 other than the end opposed to the first cover part 16A221 form a second bonded part 16A224 connected to the outer sheet by an adhesive.

Figure 27:
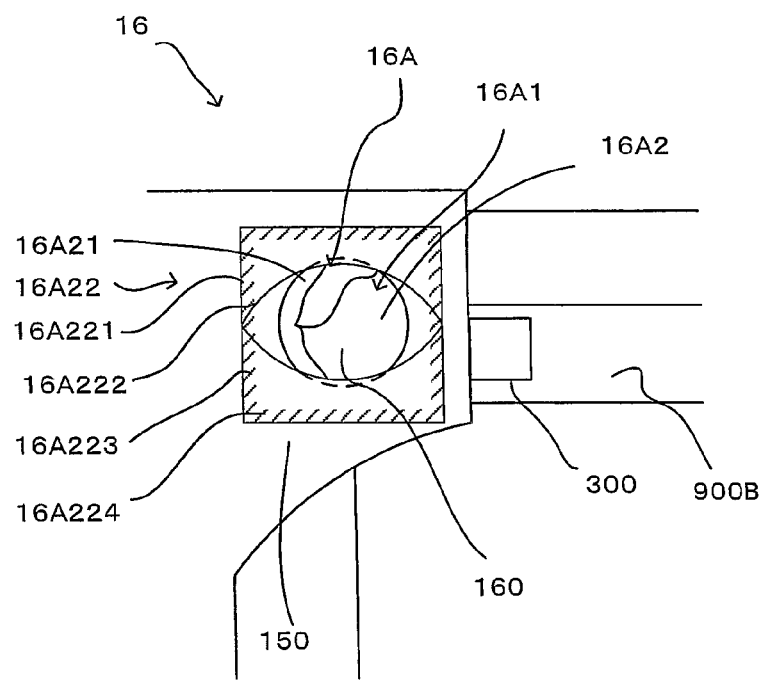
FIG. 27 is an explanatory drawing for illustrating the operation of the disposable diaper for pets according to the seventh embodiment of the present invention.

By providing the identification region 16A as the visible region 16A1 in the form of the second open identification region 16A2 and the cover region 16A22, whether the back-side flap 160 is creased or not can be confirmed when the disposable pet diaper 16 is put on a pet. Specifically, when the disposable pet diaper 16 is put on a pet, as shown in FIG. 27, the second open identification region 16A2 can be exposed by press-opening the first cover part 16A221 and the second cover part 16A223. Therefore, the state of the back-side flap 160 can be visually checked through the second open identification region 16A2.

Various structures of the identification regions are described above by means of the first to seventh embodiments of the present invention, but the structures of the identification regions of the present invention are not limited to those as described above.

The identification region may be formed by a back-side flap identification region formed in the back-side flap and an abdomen-side flap identification region formed in the abdomen-side flap.

This is an example embodiment that corresponds to the feature that "the identification region comprises a back-side flap identification region formed in the back-side flap and an abdomen-side flap identification region formed in the abdomen-side flap" according to this invention.

Eighth Embodiment

Figure 28:
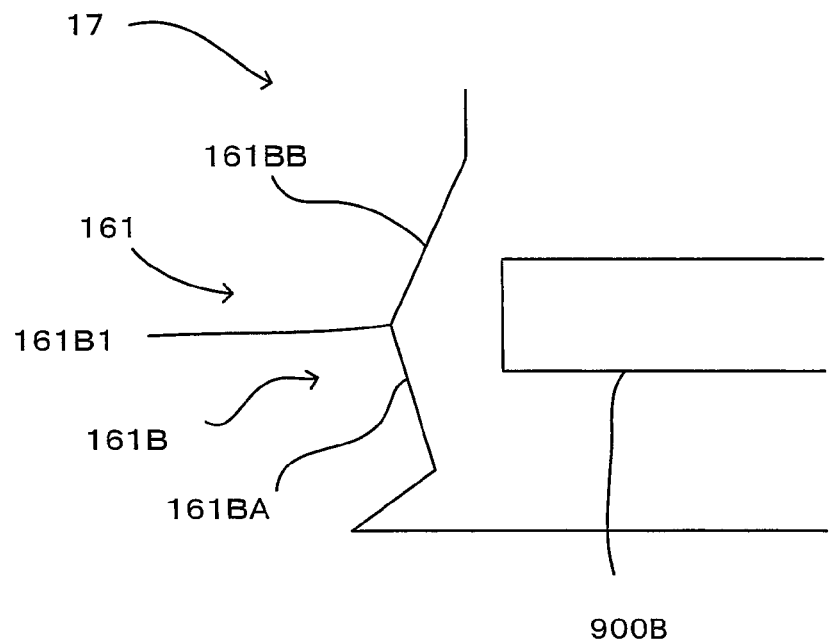
FIG. 28 is an explanatory drawing for illustrating a disposable diaper for pets according to an eighth embodiment of the present invention.

The eighth embodiment of the present invention is explained with reference to FIG. 28. In a disposable pet diaper 17 according to the eighth embodiment, a lateral end 161B of a back-side flap 161 is formed to have a shape that gradually changes in the diaper longitudinal direction. This shape of the lateral end 161B is defined by a straight line.

A maximum width region 161B1 of the lateral end 161B is formed by an intersecting part between a first straight part 161BA and a second straight part 161BB. Therefore, the maximum width region 161B1 intersects at a point with a virtual line extending in the diaper longitudinal direction.

The disposable pet diaper 17 constructed as described above according to the eighth embodiment has the same effect as the disposable pet diaper 10 of the first embodiment.

Ninth Embodiment

Figure 29:
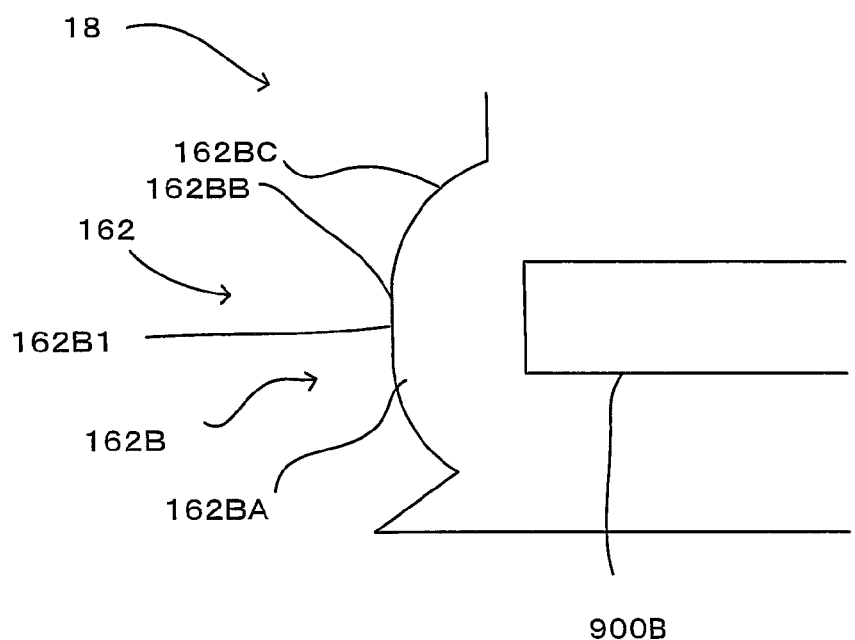
FIG. 29 is an explanatory drawing for illustrating a disposable diaper for pets according to a ninth embodiment of the present invention.

The ninth embodiment of the present invention is explained with reference to FIG. 29. In a disposable pet diaper 18 according to the ninth embodiment, a lateral end 162B of a back-side flap 162 has a region having a shape that gradually changes in the diaper longitudinal direction and a region extending parallel to the diaper longitudinal direction.

The region of the lateral end 162B of the back-side flap 162 having a shape that gradually changes in the diaper longitudinal direction, is defined by a generally circular arc curve. The generally circular arc curve has a first circular arc part 162BA and a second circular arc part 162BC.

The lateral end 162B of the back-side flap 162 further has a straight part 162BB which defines a maximum width region 162B1 having a maximum width.

The disposable pet diaper 18 constructed as described above according to the ninth embodiment has the same effect as the disposable pet diaper 10 of the first embodiment.

Tenth Embodiment

Figure 30:
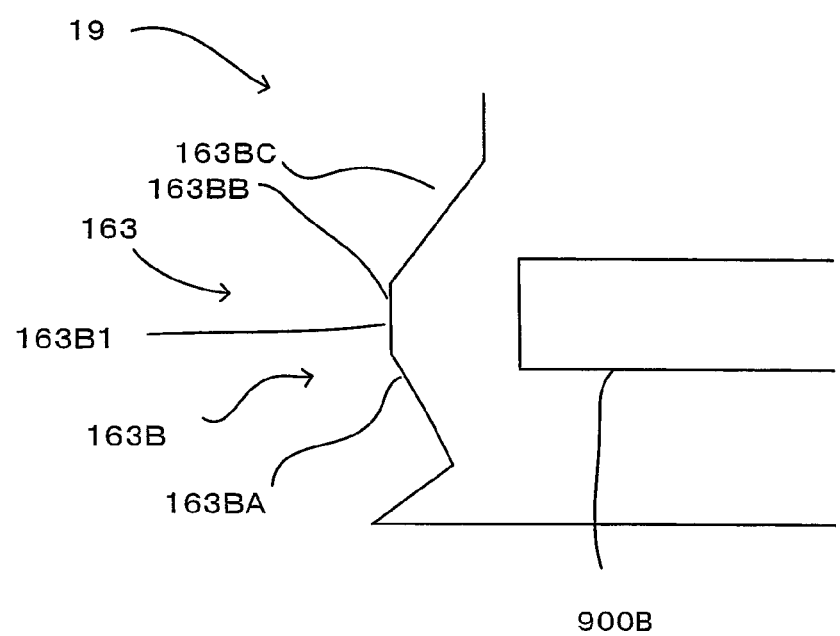
FIG. 30 is an explanatory drawing for illustrating a disposable diaper for pets according to a tenth embodiment of the present invention.

The tenth embodiment of the present invention is explained with reference to FIG. 30. In a disposable pet diaper 19 according to the tenth embodiment, a lateral end 163B of a back-side flap 163 has a region having a shape that gradually changes in the diaper longitudinal direction and a region extending parallel to the diaper longitudinal direction.

The region of the lateral end 163B of the back-side flap 163 having a shape that gradually changes in the diaper longitudinal direction, is defined by a straight line. This straight line has a first straight part 163BA and a second straight part 163BC.

The lateral end 163B of the back-side flap 163 further has a third straight part 163BB which defines a maximum width region 163B1 having a maximum width.

The disposable pet diaper 19 constructed as described above according to the tenth embodiment has the same effect as the disposable pet diaper 10 of the first embodiment.

Eleventh Embodiment

Figure 31:
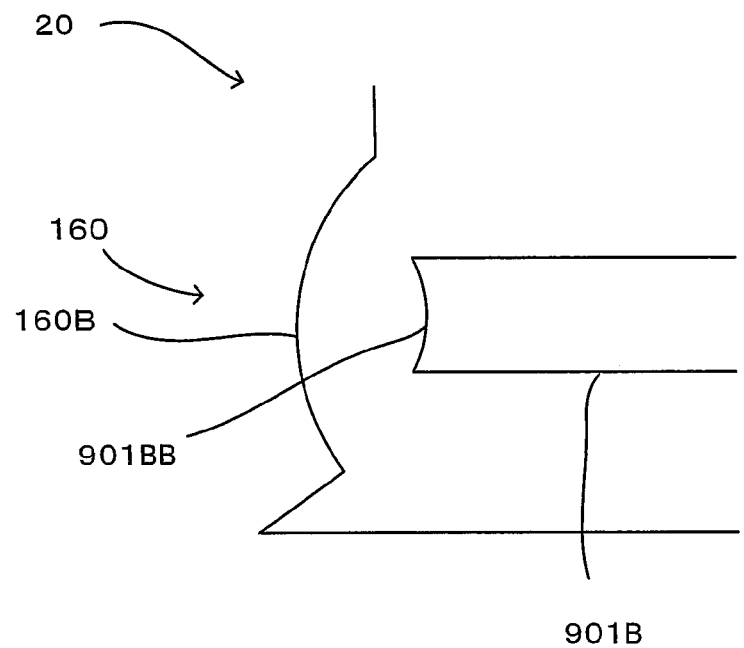
FIG. 31 is an explanatory drawing for illustrating a disposable diaper for pets according to an eleventh embodiment of the present invention.

The eleventh embodiment of the present invention is explained with reference to FIG. 31. In a disposable pet diaper 20 according to the eleventh embodiment, a lateral end 901BB of a second fastening region 901B has a shape that gradually changes in the diaper longitudinal direction.

The lateral end 901BB of the second fastening region 901B has a generally circular arc shape.

The disposable pet diaper 20 constructed as described above according to the eleventh embodiment has the same effect as the disposable pet diaper 10 of the first embodiment.

Twelfth Embodiment

Figure 32:
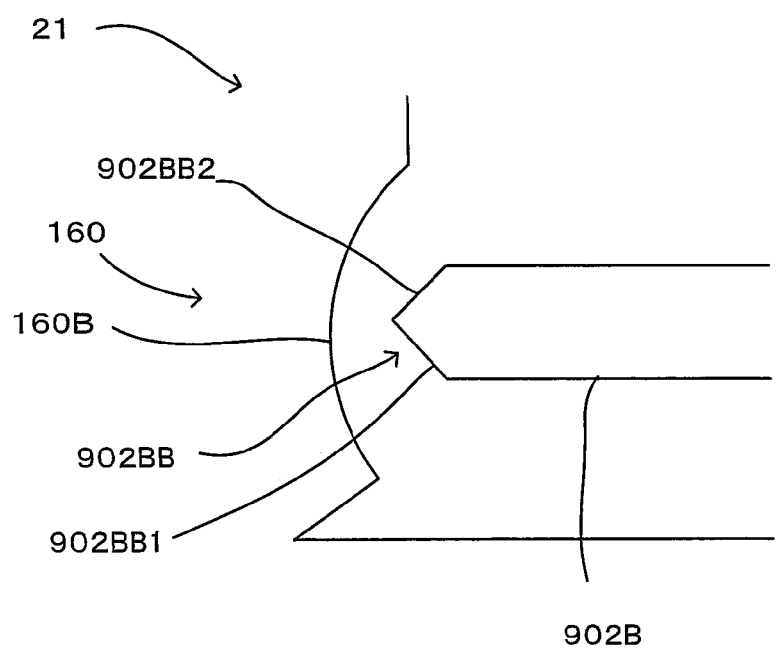
FIG. 32 is an explanatory drawing for illustrating a disposable diaper for pets according to a twelfth embodiment of the present invention.

The twelfth embodiment of the present invention is explained with reference to FIG. 32. In a disposable pet diaper 21 according to the twelfth embodiment, a lateral end 902BB of a second fastening region 902B has a shape that gradually changes in the diaper longitudinal direction.

The lateral end 902BB of the second fastening region 902B has a linear shape. Specifically, the lateral end 902BB has a first straight part 902BB1 and a second straight part 902BB2.

The disposable pet diaper 21 constructed as described above according to the twelfth embodiment has the same effect as the disposable pet diaper 10 of the first embodiment.

13th Embodiment

Figure 33:
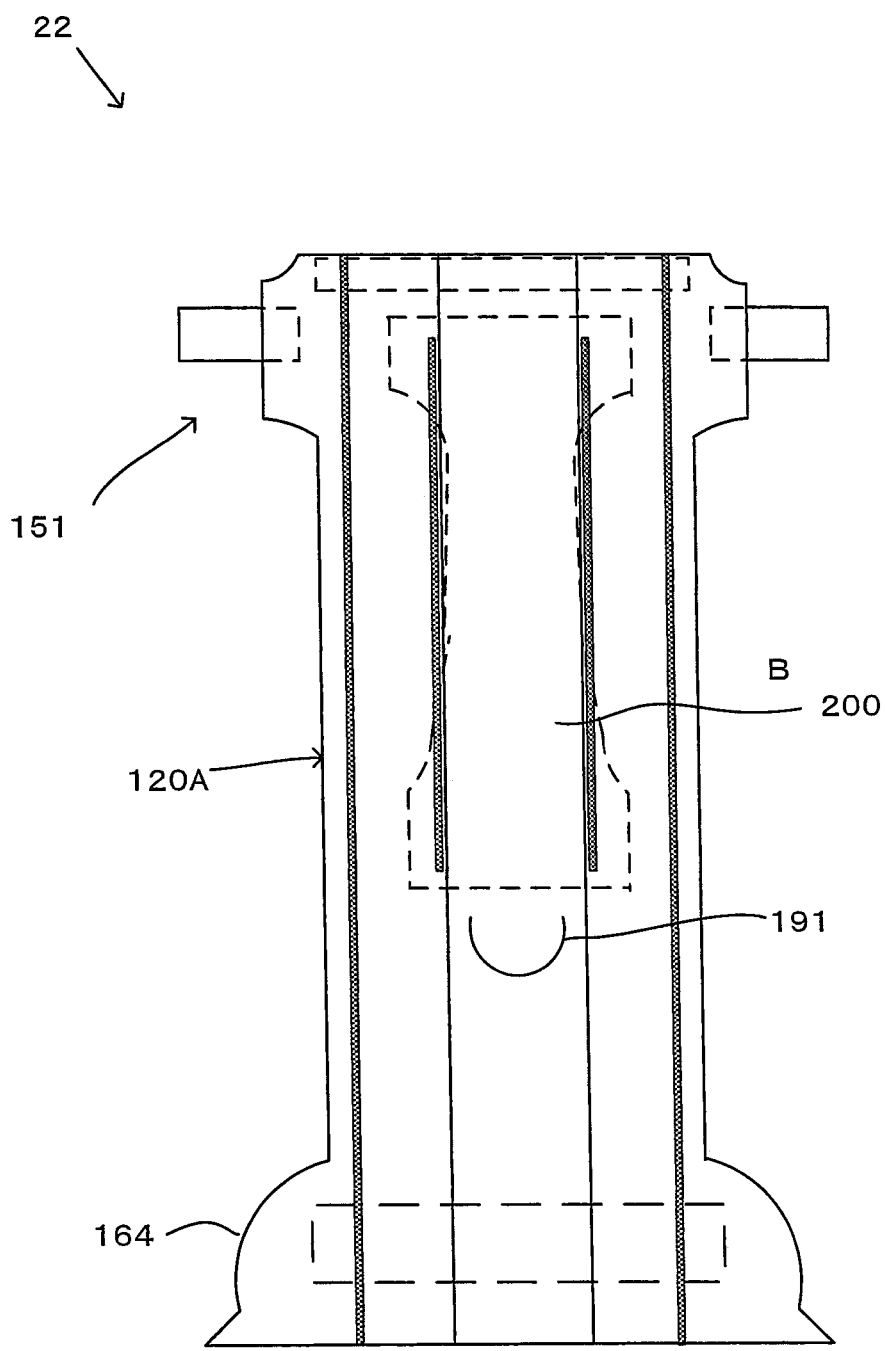
FIG. 33 is a plan view showing a disposable diaper for pets according to a 13th embodiment of the present invention, in its unfolded state.

The 13th embodiment of the present invention is explained with reference to FIG. 33. In a disposable pet diaper 22 according to the 13th embodiment, a back-side flap 164 has a longer length in the diaper transverse direction than an abdomen-side flap 151.

The disposable pet diaper 22 constructed as described above according to the 13th embodiment has the same effect as the disposable pet diaper 10 of the first embodiment.

14th Embodiment

Figure 34:
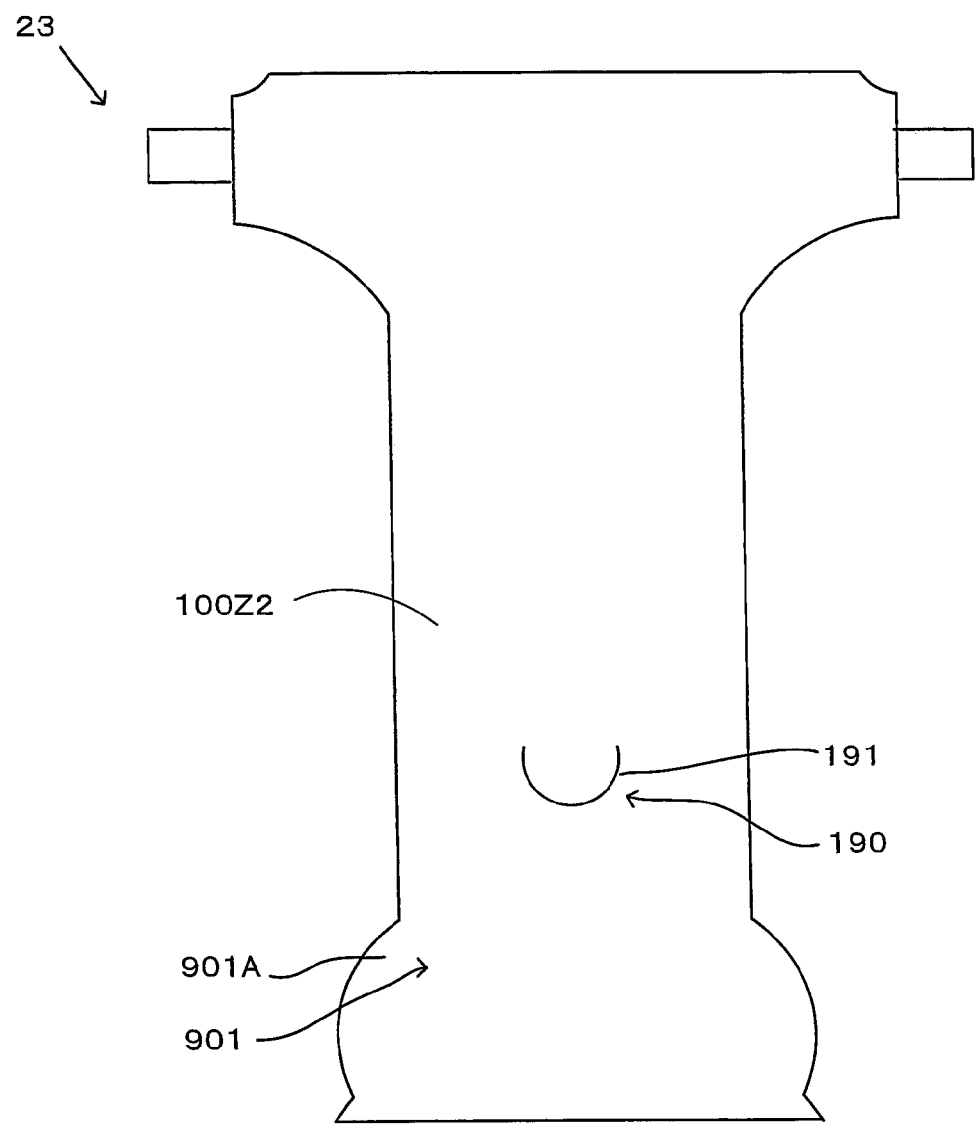
FIG. 34 is a plan view showing a disposable diaper for pets according to a 14th embodiment of the present invention, in its unfolded state.

The 14th embodiment of the present invention is explained with reference to FIG. 34. In a disposable pet diaper 23 according to the 14th embodiment, only a first fastening region 901A is provided as a fastening region 901 over the outside surface 100Z2 of the disposable pet diaper 23.

The disposable pet diaper 23 constructed as described above according to the 14th embodiment has the same effect as the disposable pet diaper 10 of the first embodiment.

15th Embodiment

Figure 35:
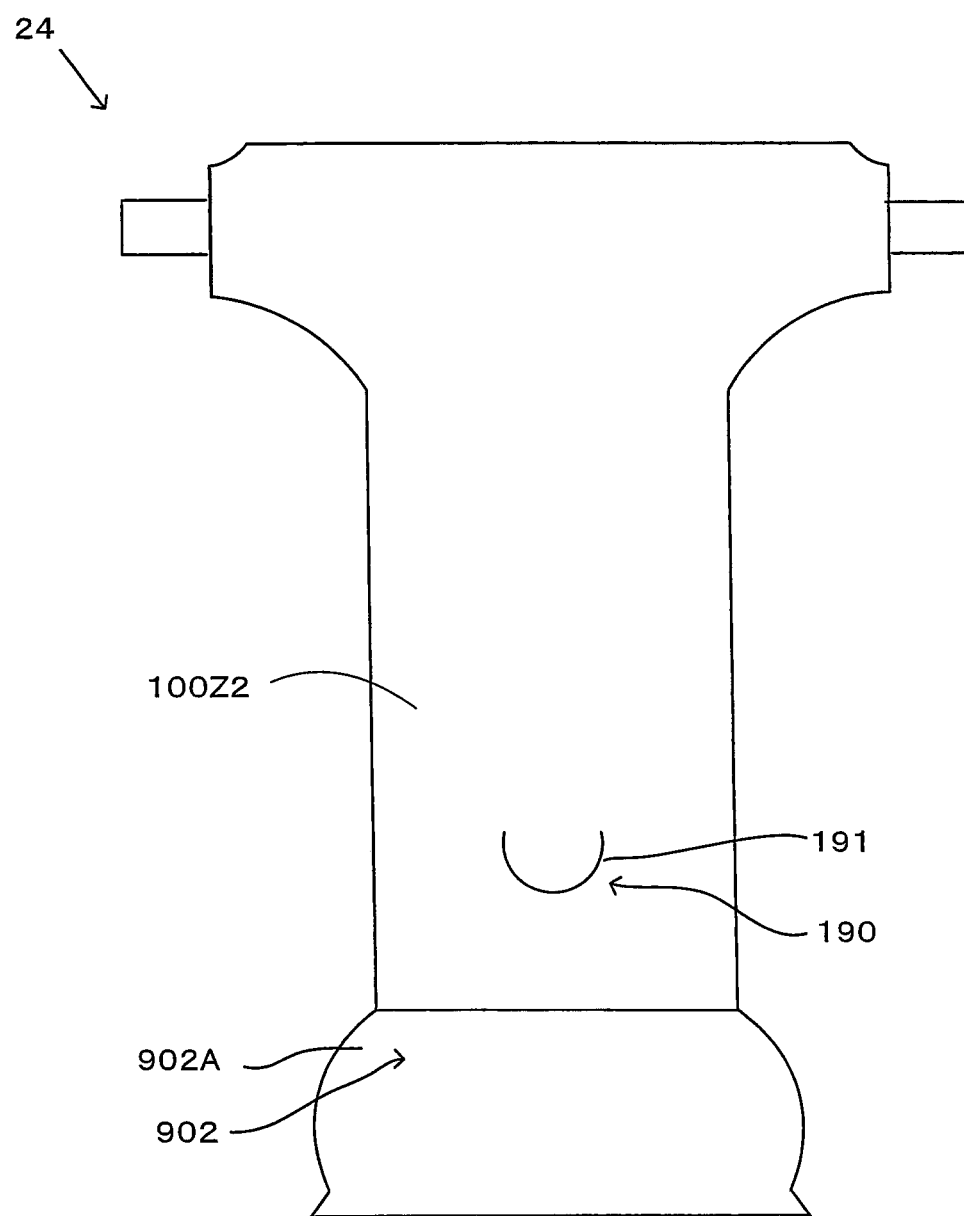
FIG. 35 is a plan view showing a disposable diaper for pets according to a 15th embodiment of the present invention, in its unfolded state.

The 15th embodiment of the present invention is explained with reference to FIG. 35. In a disposable pet diaper 24 according to the 15th embodiment, a first fastening region 902A is provided as a fastening region 902 on the outside surface 100Z2 extending over the diaper body within the back-side waist area and the back-side flaps.

In the other part of the outside surface 100Z2 which does not have the first fastening region 902A, nonwoven fabric which does not have a force of engagement with the hook part of the fastening part can be used.

The disposable pet diaper 24 constructed as described above according to the 15th embodiment has the same effect as the disposable pet diaper 10 of the first embodiment.

16th Embodiment

Figure 36:
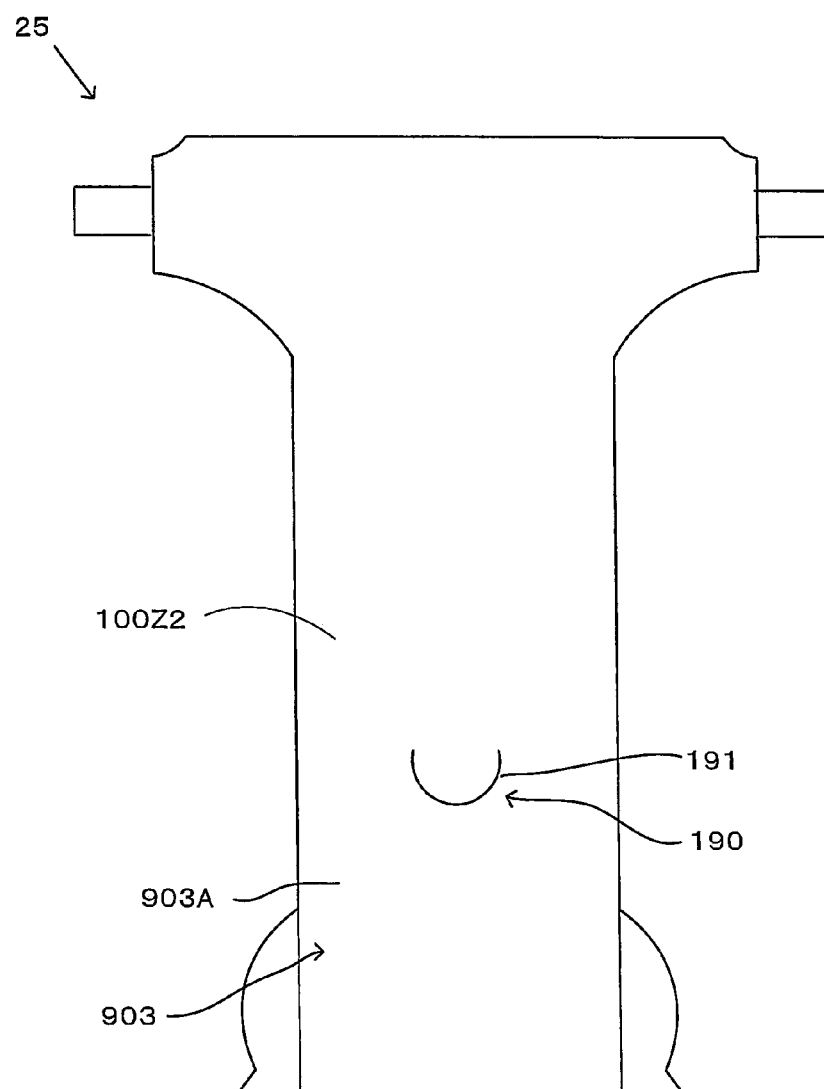
FIG. 36 is a plan view showing a disposable diaper for pets according to a 16th embodiment of the present invention, in its unfolded state.

The 16th embodiment of the present invention is explained with reference to FIG. 36. In a disposable pet diaper 25 according to the 16th embodiment, a first fastening region 903A is provided as a fastening region 903 on the outside surface 100Z2 of the diaper body within the back-side waist area.

In the outside surface of the back-side flap which does not have the first fastening region 903A, nonwoven fabric which does not have a force of engagement with the hook part of the fastening part can be used.

The disposable pet diaper 25 constructed as described above according to the 16th embodiment has the same effect as the disposable pet diaper 10 of the first embodiment.

17th Embodiment

Figure 37:
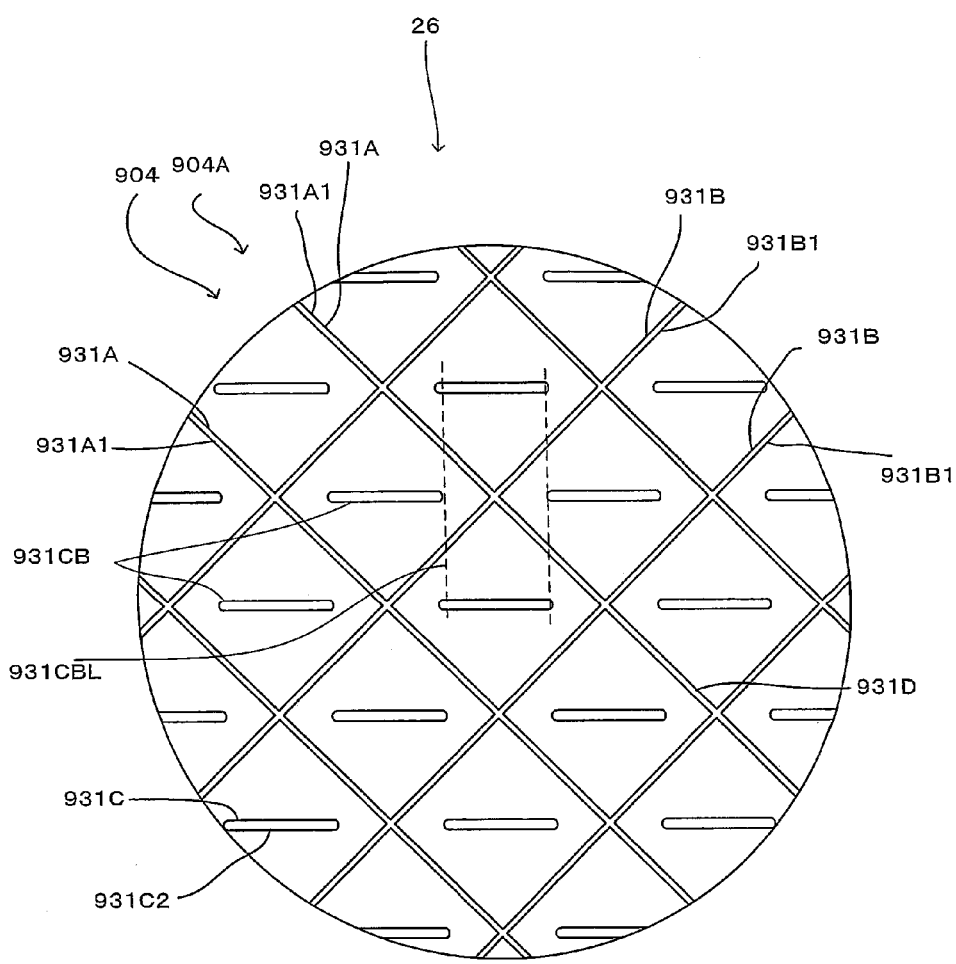
FIG. 37 is an enlarged view for illustrating a disposable diaper for pets according to a 17th embodiment of the present invention.
Figure 38:
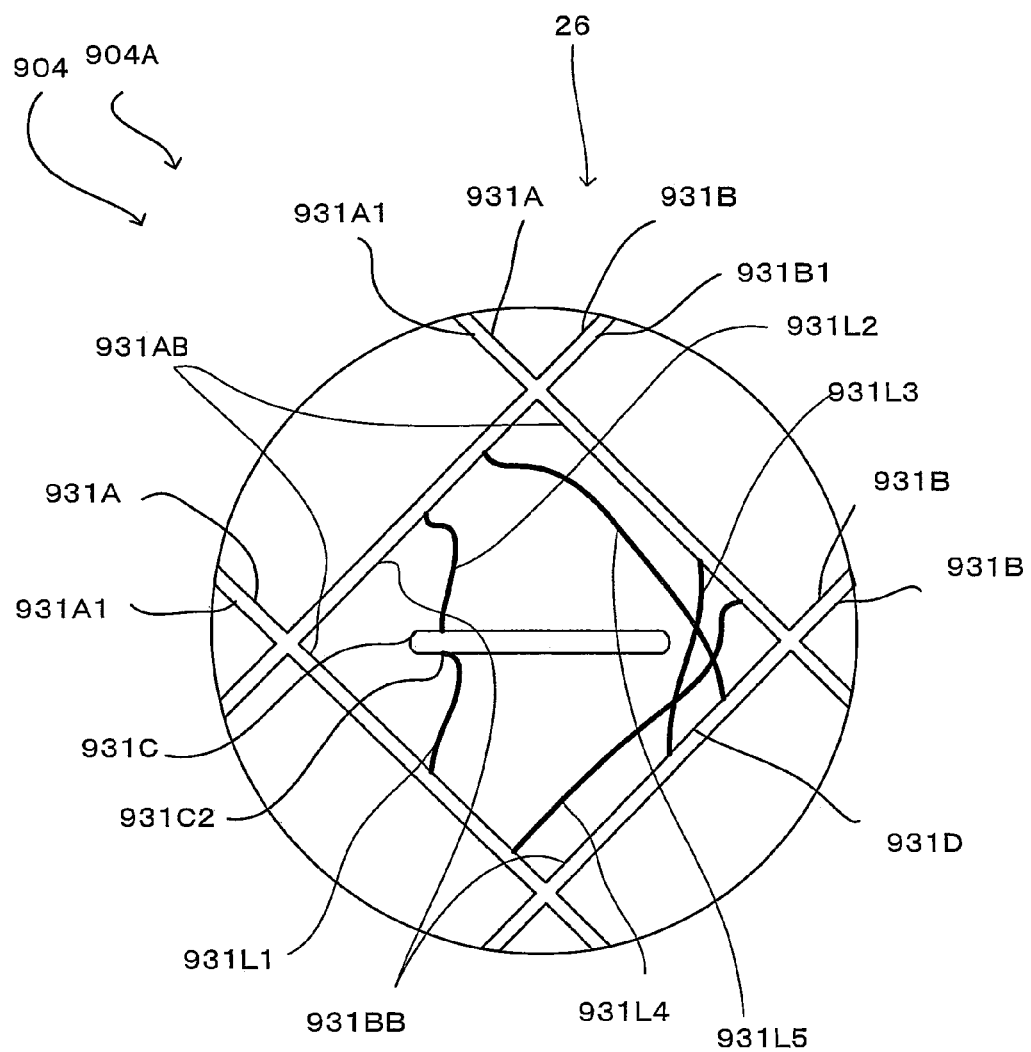
FIG. 38 is an explanatory drawing for illustrating the operation of the disposable diaper according to the 17th embodiment of the present invention.

The 17th embodiment of the present invention is explained with reference to FIGS. 37 and 38. In a disposable pet diaper 26 according to the 17th embodiment, a third welded part 931C is formed by third welded short lines 931 C2 which are continuously arranged with intervals in a first fastening region 904A of a fastening region 904.

The relation between a pair of the third welded short lines 931C2 in a third adjacent welded part group 931CB in such a case in which the third welded part 931C is formed by the third welded short lines 931 C2 is now explained.

First, lines passing each end of the third welded short lines 931C2 and running perpendicularly to the third direction are referred to as virtual lines 931CBL.

In one of a pair of the adjacent third welded parts 931C of the third adjacent welded part group 931CB, the third welded short line 931C2 is located between the virtual lines 931CBL, while, in the other third welded part 931C, a space between the third welded short lines 931C2 exists between the virtual lines 931CBL. This relation is defined as the relation that "the welded short lines in the adjacent welded part group do not overlap with each other".

In such a case in which the third welded part 931C is formed by the third welded short lines 931C2, other arrangement of a pair of the third welded parts 931C forming the third adjacent welded part group 931CB is now considered.

In the third adjacent welded part group 931CB, a pair of the third welded short lines 931C2 may exist in a direction perpendicular to the third direction. This relation is defined as the relation that "the welded short lines in the adjacent welded part group overlap with each other".

The relation that "the welded short lines in the adjacent welded part group overlap with each other" and the relation that "the welded short lines in the adjacent welded part group do not overlap with each other" may also be provided in the first and second welded parts. Specifically, these relations of "the welded short lines in the adjacent welded part group" can be appropriately selected depending on the structure of the loop parts to be obtained.

A surrounding part 931D of the disposable pet diaper 26 according to the 17th embodiment is now described with reference to FIG. 38.

The surrounding part 931D is defined by a first welded part 931A in the form of a first continuous line 931A1 and a second welded part 931B in the form of a second continuous line 931B1.

In the surrounding part 931D, a first loop part 931L1 and a second loop part 931L2 are formed.

Further, by providing the third welded part 931C as the third welded short lines 931 C2, a third loop part 931L3 is formed of thermoplastic fibers extending from the first welded part 931A to the second welded part 931B through a space between the third welded short lines 931C2 of the third welded part 931C and can be removably engaged with the hook part of the fastening part.

Further, a fourth loop part 931L4 is formed of thermoplastic fibers extending from one of the first welded parts 931A of a first adjacent welded part group 931AB to the other first welded part 931A through a space between the third welded short lines 931C2 of the third welded part 931C and can be removably engaged with the hook part of the fastening part.

Further, a fifth loop part 931L5 is formed of thermoplastic fibers extending from one of the second welded parts 931B of a second adjacent welded part group 931BB to the other second welded part 931B through a space between the third welded short lines 931C2 of the third welded part 931C and can be removably engaged with the hook part of the fastening part.

The disposable pet diaper 26 constructed as described above according to the 17th embodiment is suitable for use with a hook part having a different structure from that of the disposable pet diaper 10 of the first embodiment.

18th Embodiment

Figure 39:
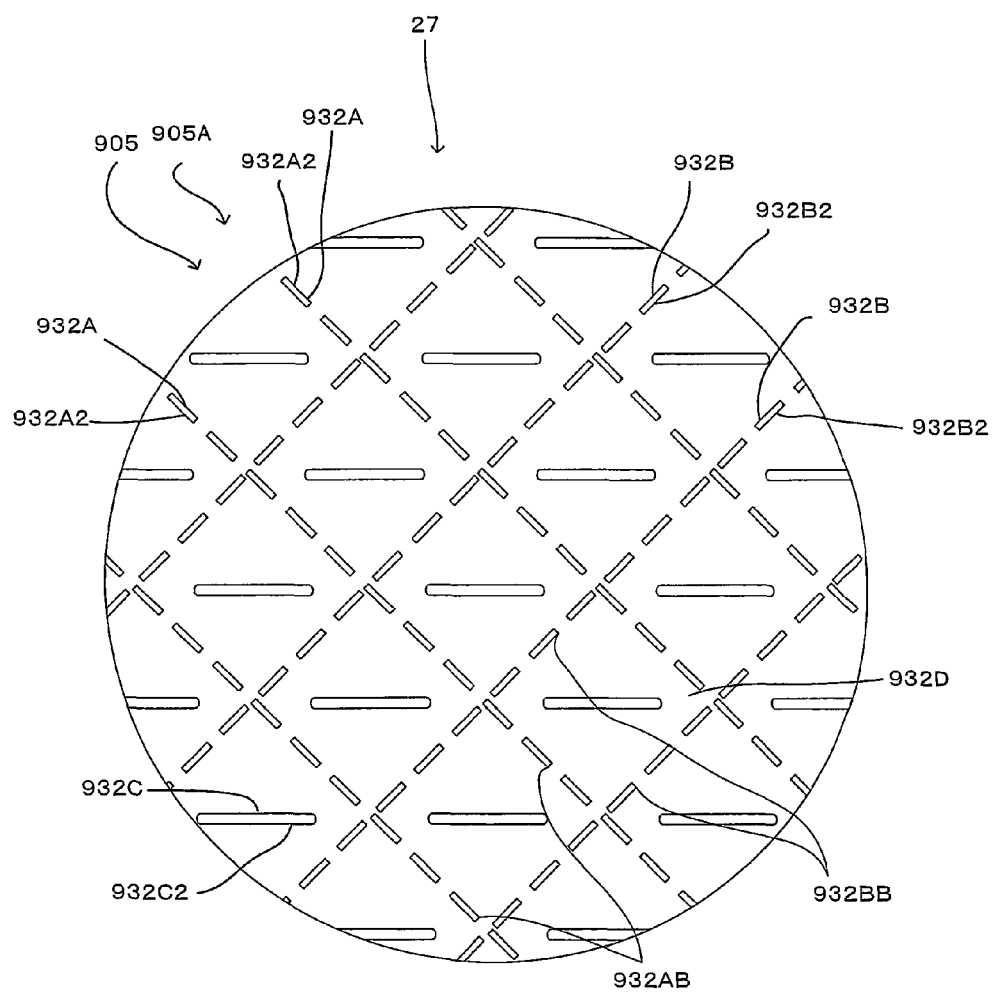
FIG. 39 is an enlarged view for illustrating a disposable diaper for pets according to an 18th embodiment of the present invention.

The 18th embodiment of the present invention is explained with reference to FIG. 39. In a disposable pet diaper 27 according to the 18th embodiment, a first welded part 932A, a second welded part 932B and a third welded part 932C are formed as first welded short lines 932A2, second welded short lines 932B2 and third welded short lines 932C2, respectively, in a first fastening region 905A of a fastening region 905.

By provision of this structure, in addition to the first to fifth loop parts, a sixth loop part can be formed by thermoplastic fibers extending over the adjacent surrounding parts 932D and can be removably engaged with the hook part of the fastening part.

Further, the first welded short lines 932A2 of a first adjacent welded part group 932AB overlap with each other, and the second welded short lines 932B2 of a second adjacent welded part group 932BB overlap with each other.

The disposable pet diaper 27 constructed as described above according to the 18th embodiment is suitable for use with a hook part having a different structure from that of the disposable pet diaper 10 of the first embodiment.

19th Embodiment

Figure 40:
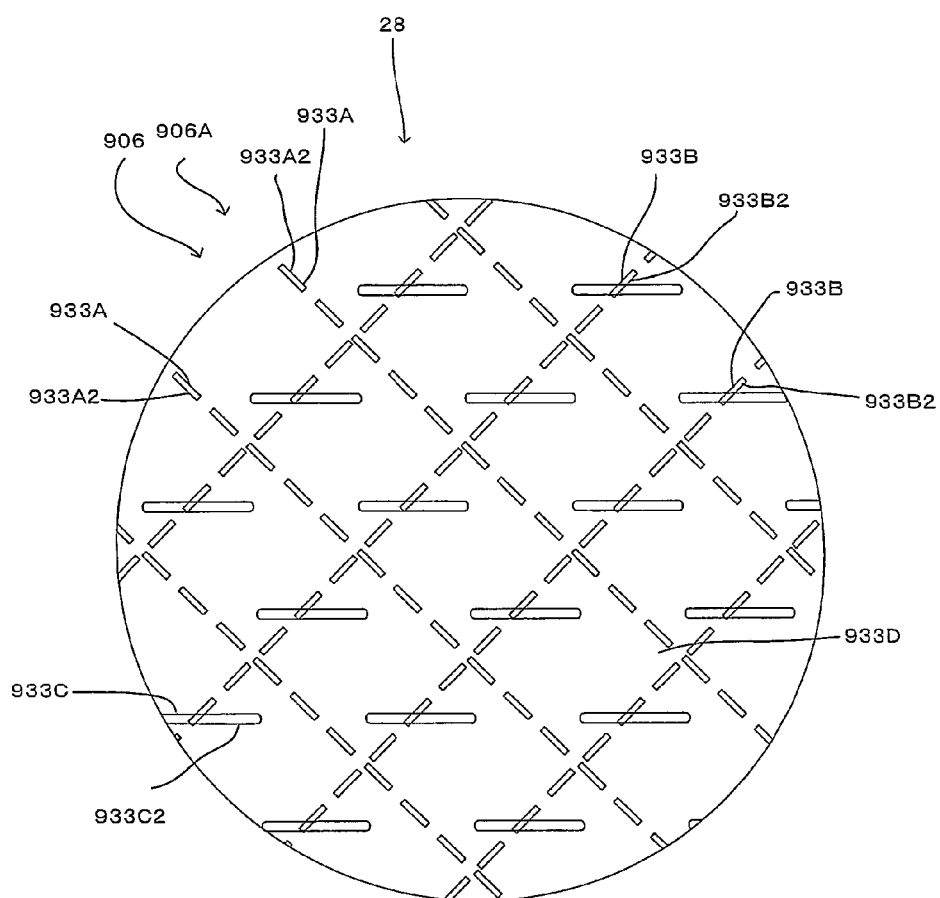
FIG. 40 is an enlarged view for illustrating a disposable diaper for pets according to a 19th embodiment of the present invention.

The 19th embodiment of the present invention is explained with reference to FIG. 40. In a disposable pet diaper 28 according to the 19th embodiment, a first welded part 933A, a second welded part 933B and a third welded part 933C are formed as first welded short lines 933A2, second welded short lines 933B2 and third welded short lines 933C2, respectively, in a first fastening region 906A of a fastening region 906.

The third welded short lines 933C2 are provided to extend over the adjacent surrounding parts 932D.

By provision of this structure, the first to sixth loop parts having different lengths from those of the above-described first, 17th and 18th embodiments can be formed.

The disposable pet diaper 28 constructed as described above according to the 19th embodiment is suitable for use with a hook part having a different structure from that of the disposable pet diaper 10 of the first embodiment.

20th Embodiment

Figure 41:
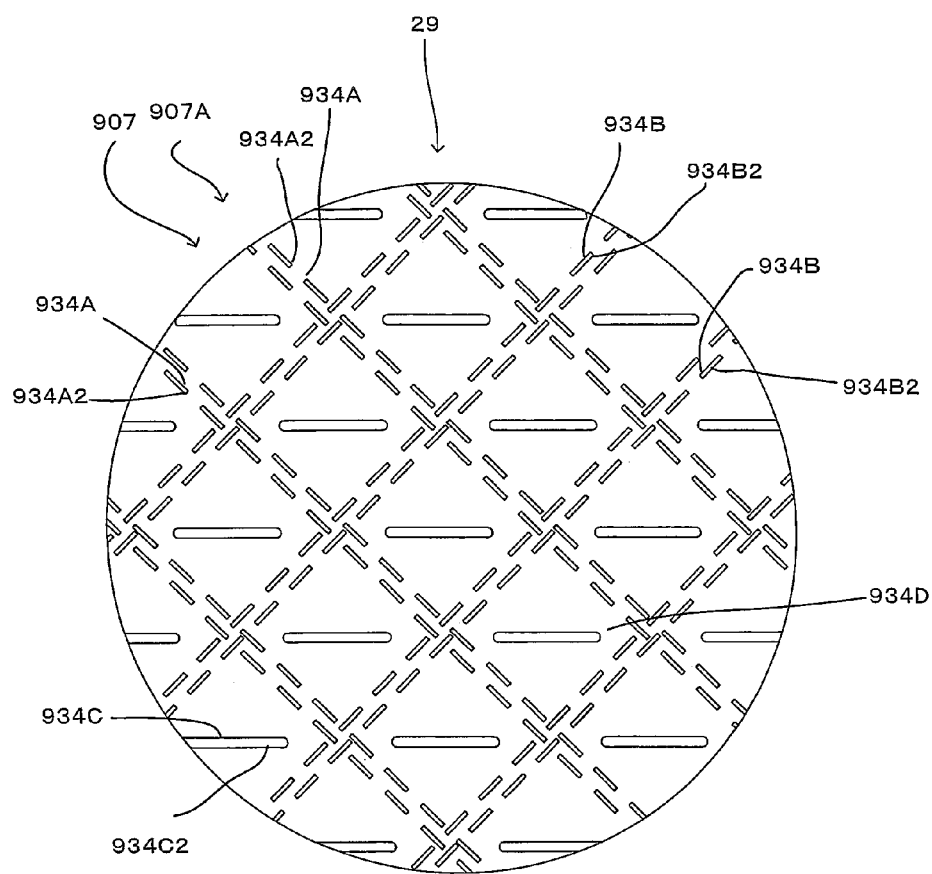
FIG. 41 is an enlarged view for illustrating a disposable diaper for pets according to a 20th embodiment of the present invention.

The 20th embodiment of the present invention is explained with reference to FIG. 41. In a disposable pet diaper 29 according to the 20th embodiment, a first welded part 934A, a second welded part 934B and a third welded part 934C are formed as first welded short lines 934A2, second welded short lines 934B2 and third welded short lines 934C2, respectively, in a first fastening region 907A of a fastening region 907.

Further, the first welded part 934A is formed by two parallel first welded parts 934A, and the second welded part 934B is formed by two parallel second welded parts 934B.

By provision of this structure, the first to sixth loop parts having different lengths from those of the above-described first and 17th to 19th embodiments can be formed.

The disposable pet diaper 29 constructed as described above according to the 20th embodiment is suitable for use with a hook part having a different structure from those of the disposable pet diaper 10 of the first embodiment.

21st Embodiment

Figure 42:
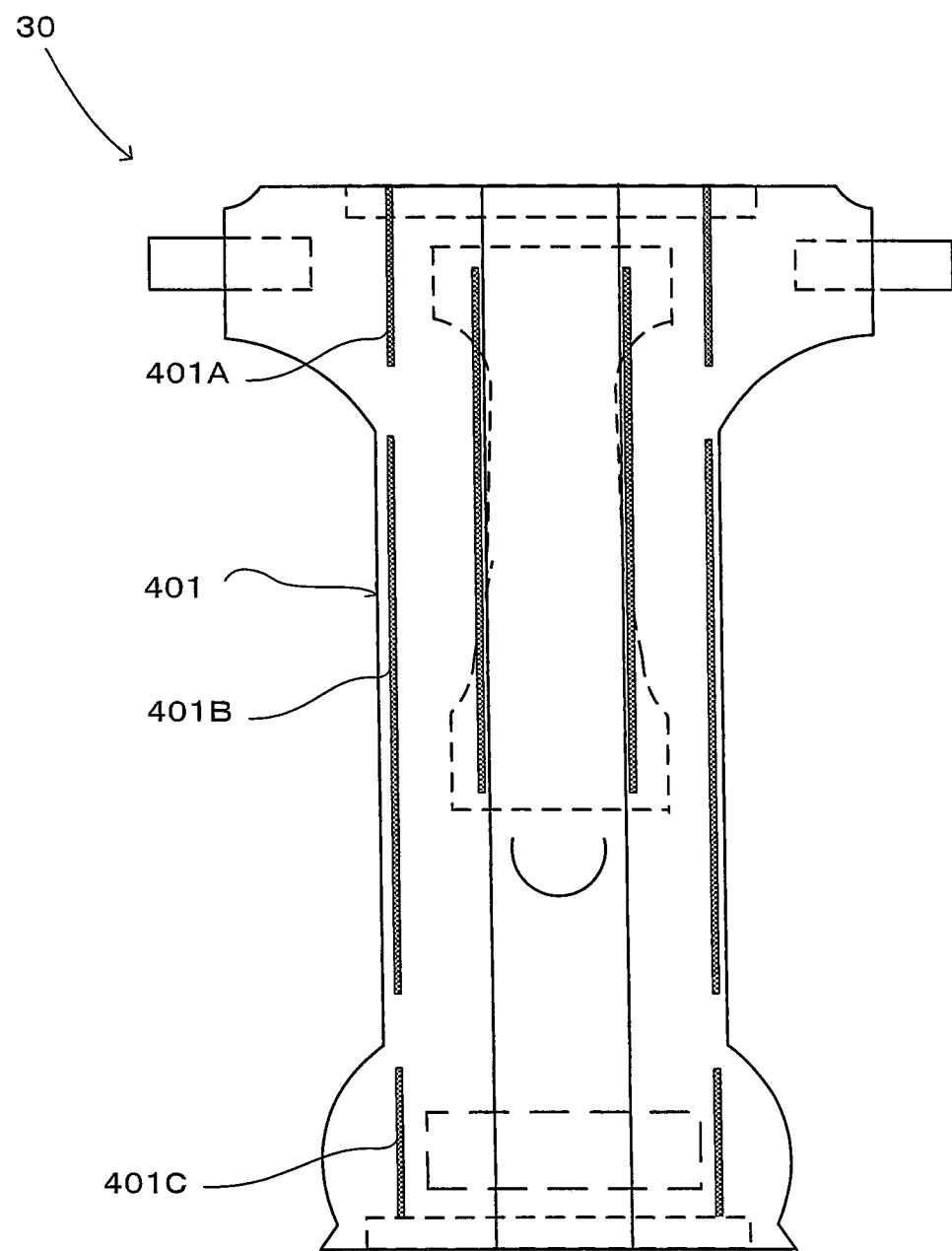
FIG. 42 is a plan view showing a disposable diaper for pets according to a 21st embodiment of the present invention, in its unfolded state.

The 21st embodiment of the present invention is explained with reference to FIG. 42. A disposable pet diaper 30 according to the 21st embodiment is different from the disposable pet diaper 10 of the first embodiment in that a leg stretchable elastic member 401 includes a plurality of leg stretchable elastic members. Specifically, the leg stretchable elastic member 401 of the 21st embodiment is configured by continuously arranging a plurality of leg stretchable elastic members with intervals in the diaper longitudinal direction. The number of the continuously arranged leg stretchable elastic members can be appropriately selected according to the disposable pet diaper to be realized.

In the 21st embodiment of this invention, the leg stretchable elastic member 401 extending continuously in the diaper longitudinal direction includes three leg stretchable elastic members, or a leg stretchable elastic member 401A in the abdomen-side waist area, a leg stretchable elastic member 401B in the crotch area, and a leg stretchable elastic member 401C in the back-side waist area.

Like in the first embodiment, in the 21st embodiment, the erected section 700 including the abdomen-side erected section 710, the back-side erected section 720 and the crotch-side erected section 730 is formed, and the leakproof wall 820 is formed. Further, the first curved part 540 including the first abdomen-side curved part 541 and the first back-side curved part 542, the second curved part 183 including the second abdomen-side curved part 184 and the second back-side curved part 185, the third curved part 640 and the fourth curved part 420 are formed. Further, the leg gathers 410, the waist gathers 530 and the leakproof gathers 840 are formed.

Therefore, the disposable pet diaper 30 according to the 21st embodiment has the same effect as the disposable pet diaper 10 of the first embodiment.

Furthermore, by provision of the leg stretchable elastic member 401 including the three leg stretchable elastic members, the stretching forces of the leg stretchable elastic members can be prevented from affecting each other. Therefore, for example, the back-side waist area is little affected by displacement (or slippage) of the abdomen-side waist area, if any, so that displacement can be prevented as a whole.

22nd Embodiment

Figure 43:
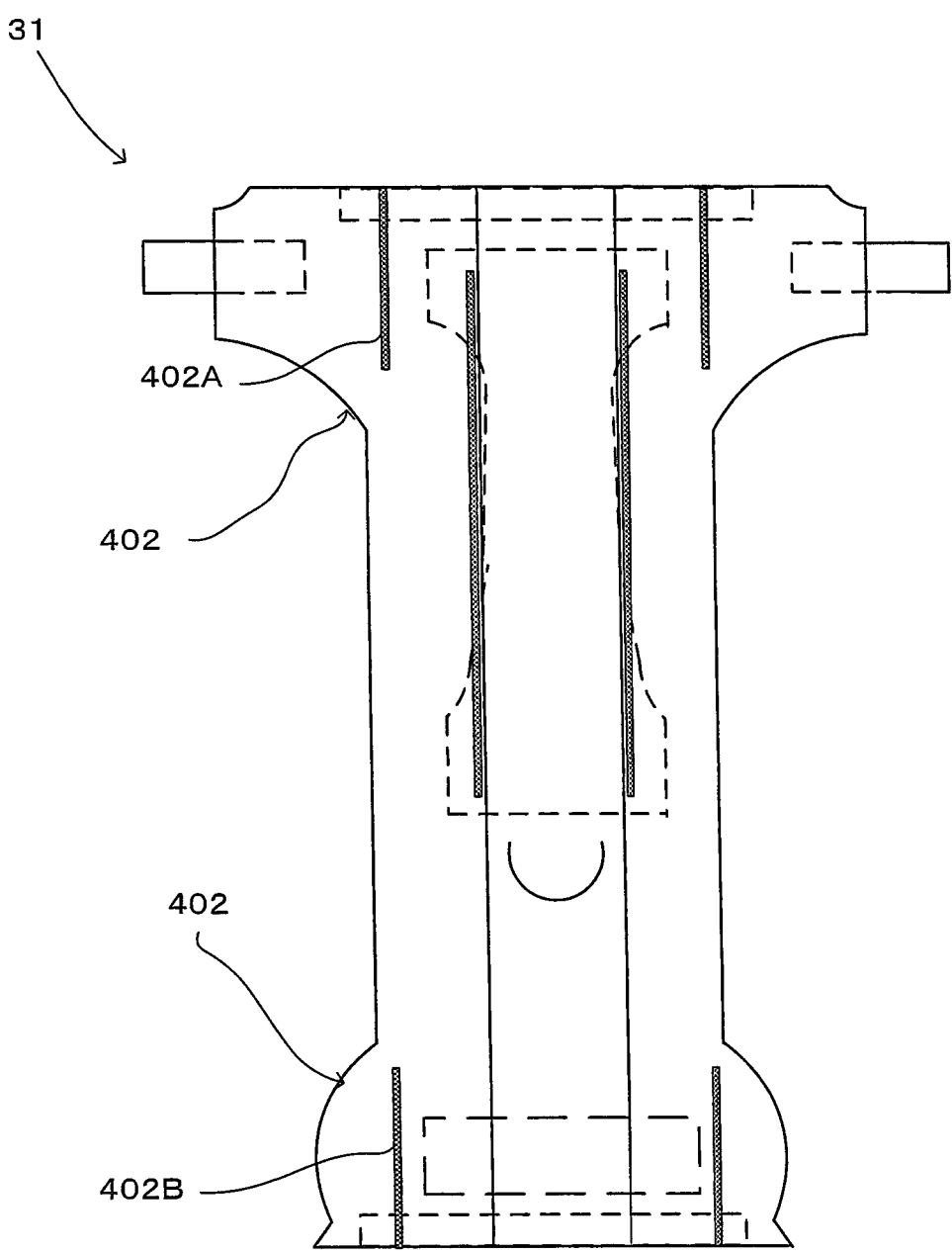
FIG. 43 is a plan view showing a disposable diaper for pets according to a 22nd embodiment of the present invention, in its unfolded state.

The 22nd embodiment of the present invention is explained with reference to FIG. 43. A disposable pet diaper 31 according to the 22nd embodiment is different from the disposable pet diaper 10 of the first embodiment in that a leg stretchable elastic member 402 is not continuously arranged in the diaper longitudinal direction.

Specifically, in the 22nd embodiment of this invention, the leg stretchable elastic member 402 includes a leg stretchable elastic member 402A disposed in the abdomen-side waist area of the disposable pet diaper 31 and a leg stretchable elastic member 402B disposed in the back-side waist area.

The 22nd embodiment is different from the first embodiment in that the leg gathers 410 and the fourth curved part 420 are formed only in the regions of the leg stretchable elastic members 402A and 402B in the disposable pet diaper 31.

In this structure, the erected section 700 including the abdomen-side erected section 710, the back-side erected section 720 and the crotch-side erected section 730 is formed, and the leakproof wall 820 is formed. Further, the first curved part 540 including the first abdomen-side curved part 541 and the first back-side curved part 542, the second curved part 183 including the second abdomen-side curved part 184 and the second back-side curved part 185, the third curved part 640 and part of the fourth curved part 420 are formed. Further, part of the leg gathers 410, the waist gathers 530 and the leakproof gathers 840 are formed.

Therefore, the disposable pet diaper 31 according to the 22nd embodiment has all of the effects of the disposable pet diaper 10 of the first embodiment other than those exhibited by the whole leg gathers 410 and the whole fourth curved part 420.

Furthermore, in this structure, the stretchable elastic member is not provided in the crotch area in which the absorbent core is disposed, and nor in the free end of the leakproof gathers. Therefore, the absorbent core does not shrink, so that the area of the absorbent core can be effectively used.

Further, a pocket space can be readily formed in both end regions of the absorbent core in the diaper longitudinal direction.

Moreover, the stretchable elastic member is not provided in the fastening region. Therefore, the fastening region does not shrink, so that the fastening part can be easily engaged with the fastening region.

23rd Embodiment

Figure 44:
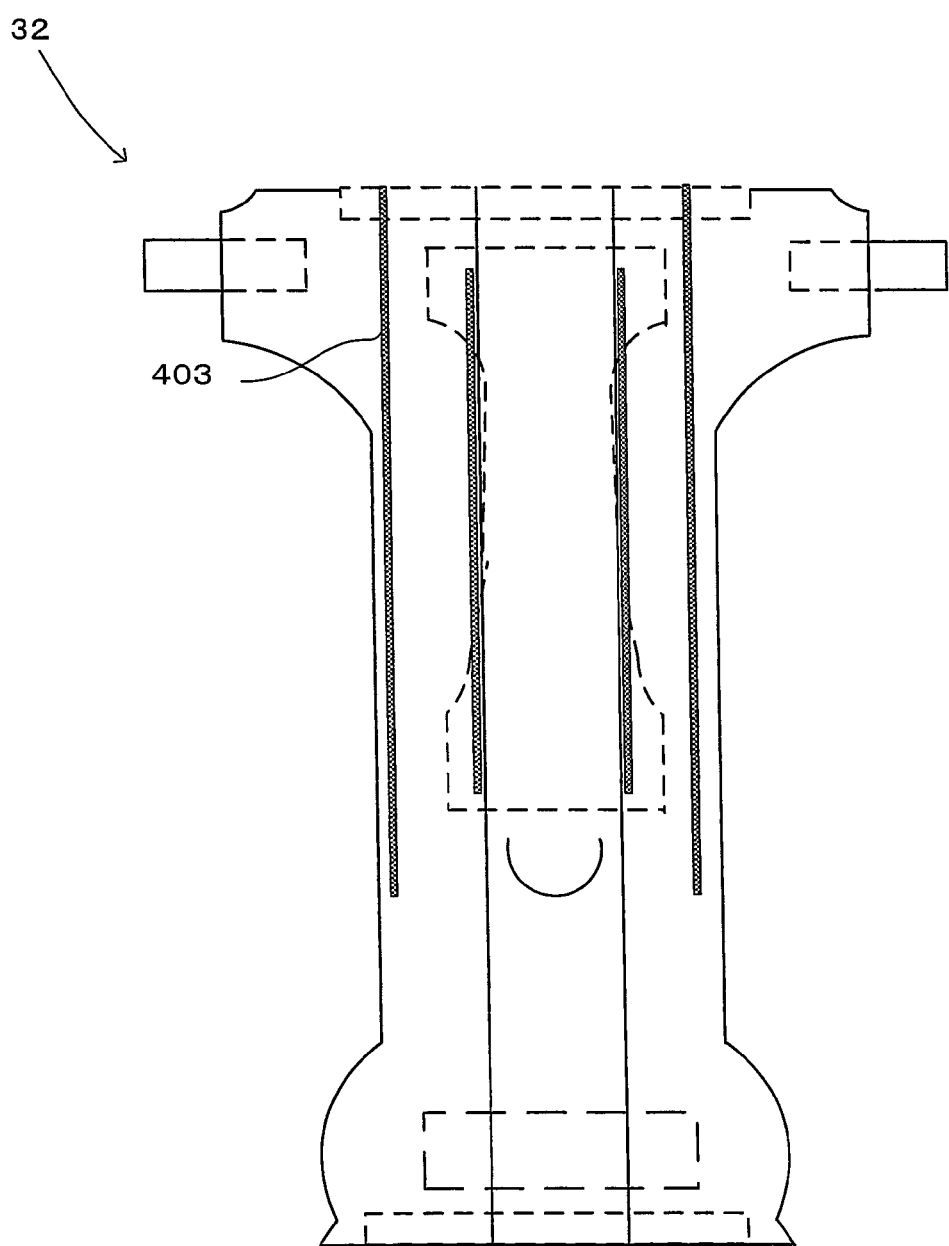
FIG. 44 is a plan view showing a disposable diaper for pets according to a 23rd embodiment of the present invention, in its unfolded state.

The 23rd embodiment of the present invention is explained with reference to FIG. 44. A disposable pet diaper 32 according to the 23rd embodiment is different from the disposable pet diaper 10 of the first embodiment in that a leg stretchable elastic member 403 is not provided in the back-side waist area. Further, the contraction force of the leakproof sheet stretchable elastic member exerts no influence on the abdomen-side end of the disposable pet diaper 32.

Compared with the disposable pet diaper 10 of the first embodiment, the disposable pet diaper 32 of the 23rd embodiment is different in that the leg gathers 410 and the fourth curved part 420 are formed only in the region of the leg stretchable elastic member 403. Further, the back-side erected section 720 of the erected section 700 and the second back-side curved part 185 of the second curved part 183 are not formed.

In this structure, the erected section 700 including the abdomen-side erected section 710 and the crotch-side erected section 730 is formed, and the leakproof wall 820 is formed. Further, the first curved part 540 including the first abdomen-side curved part 541 and the first back-side curved part 542, the second curved part 183 including the second abdomen-side curved part 184, the third curved part 640 and part of the fourth curved part 420 are formed. Further, part of the leg gathers 410, the waist gathers 530 and the leakproof gathers 840 are formed.

Therefore, the disposable pet diaper 32 according to the 23rd embodiment has all of the effects of the disposable pet diaper 10 of the first embodiment other than those exhibited by the whole leg gathers 410, the back-side erected section 720, the second back-side curved part 185 and the whole fourth curved part 420.

Further, a pocket space can be readily formed in back-side and abdomen-side end regions of the absorbent core.

24th Embodiment

Figure 45:
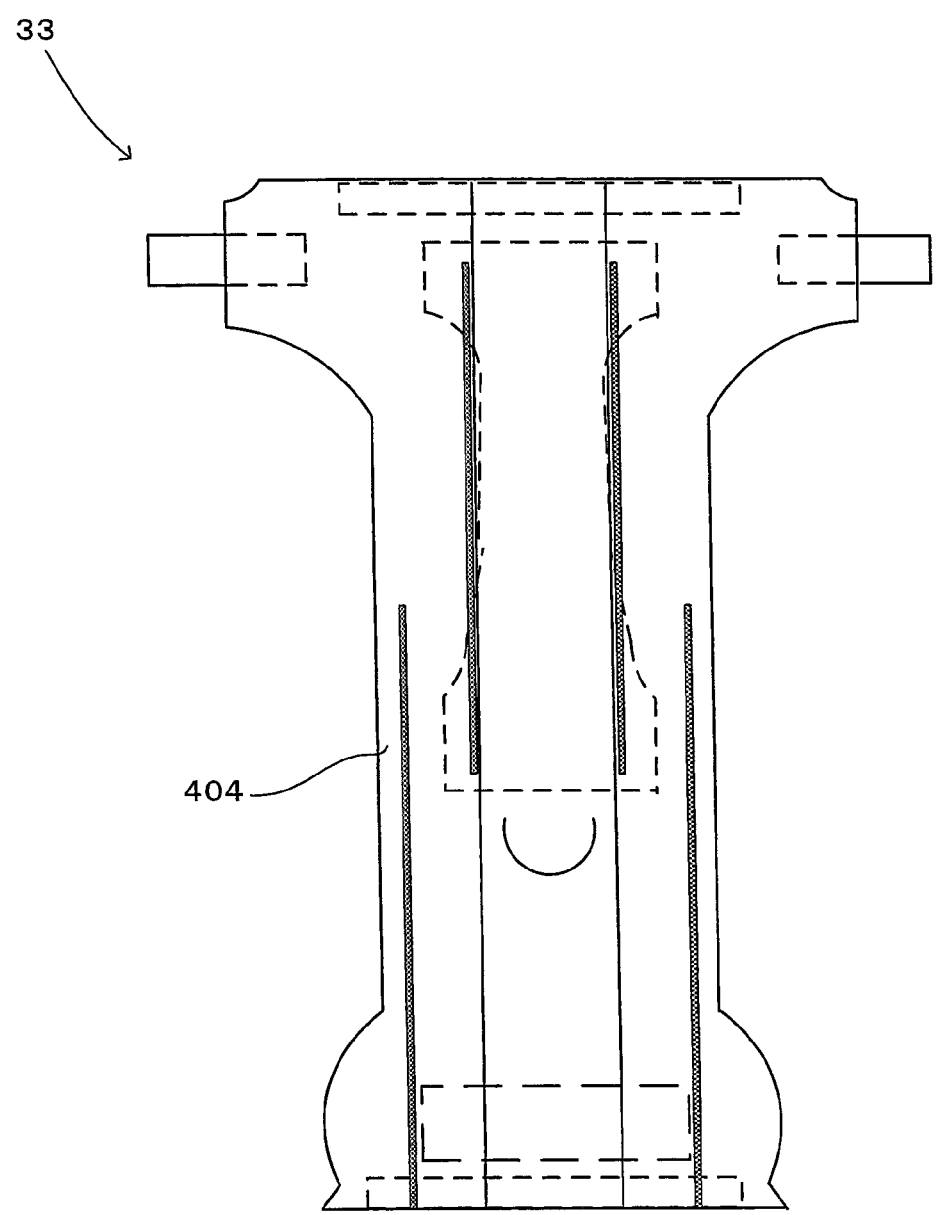
FIG. 45 is a plan view showing a disposable diaper for pets according to a 24th embodiment of the present invention, in its unfolded state.

The 24th embodiment of the present invention is explained with reference to FIG. 45. A disposable pet diaper 33 according to the 24th embodiment is different from the disposable pet diaper 10 of the first embodiment in that a leg stretchable elastic member 404 is not provided in the abdomen-side waist area. Further, the contraction force of the leakproof sheet stretchable elastic member exerts no influence on the back-side end of the disposable pet diaper 33.

Compared with the disposable pet diaper 10 of the first embodiment, the disposable pet diaper 33 of the 24th embodiment is different in that the leg gathers 410 are formed only in the region of the leg stretchable elastic member 404. Further, the abdomen-side erected section 710 of the erected section 700 and the second abdomen-side curved part 184 of the second curved part 183 are not formed.

In this structure, the erected section 700 including the back-side erected section 720 and the crotch-side erected section 730 is formed, and the leakproof wall 820 is formed. Further, the first curved part 540 including the first abdomen-side curved part 541 and the first back-side curved part 542, the second curved part 183 including the second back-side curved part 185, the third curved part 640 and the fourth curved part 420 are formed. Further, part of the leg gathers 410, the waist gathers 530 and the leakproof gathers 840 are formed.

Therefore, the disposable pet diaper 33 according to the 24th embodiment has all of the effects of the disposable pet diaper 10 of the first embodiment other than those exhibited by the whole leg gathers 410, the abdomen-side erected section 710 and the second abdomen-side curved part 184.

Further, the absorbent core is not subjected to a contraction force, so that the area of the absorbent core can be effectively used.

Moreover, by provision of the leg stretchable elastic member only in the back-side area, it is made easier to fit the disposable pet diaper along the back of the pet. As a result, the fastening part can be easily engaged with the fastening region.

25th Embodiment

Figure 46:
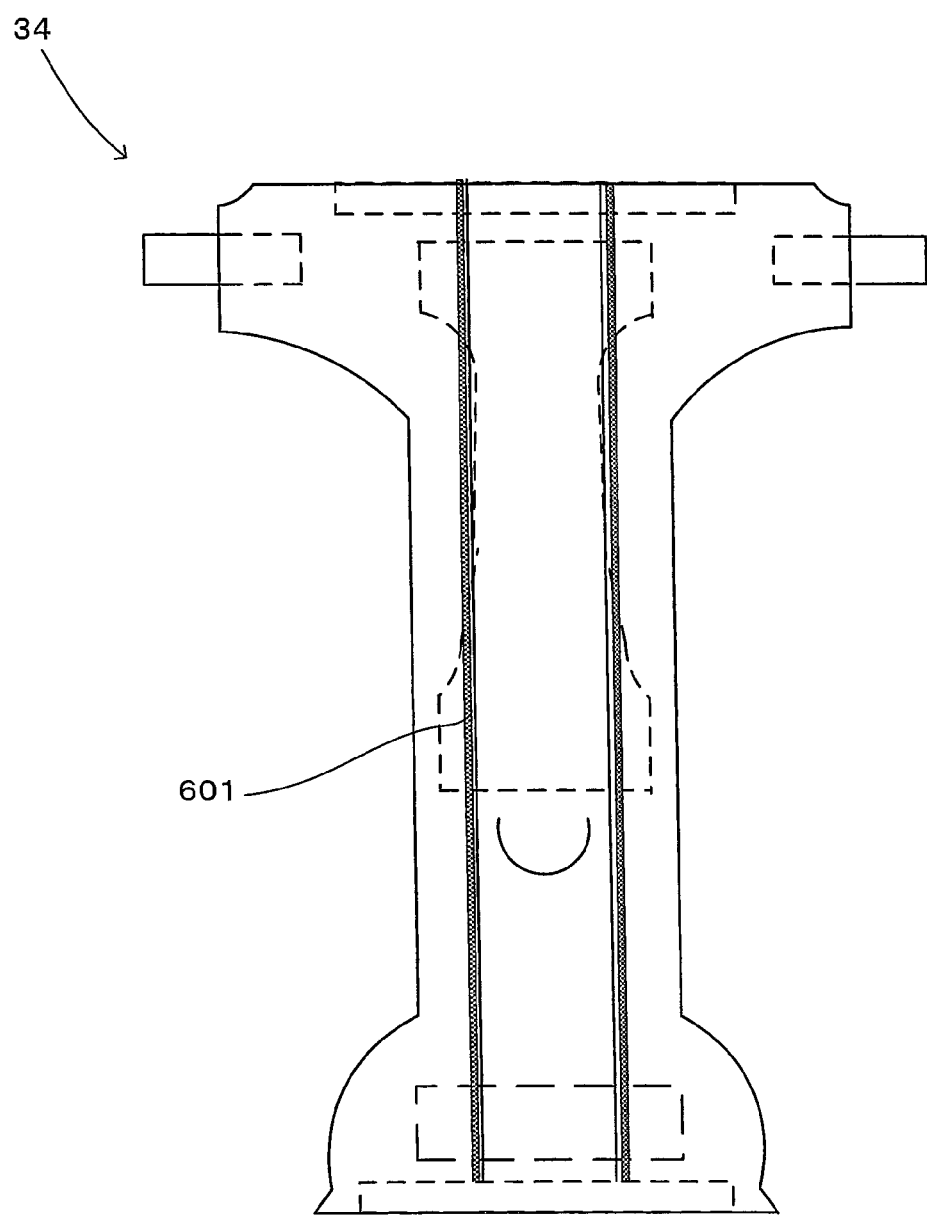
FIG. 46 is a plan view showing a disposable diaper for pets according to a 25th embodiment of the present invention, in its unfolded state.

The 25th embodiment of the present invention is explained with reference to FIG. 46. A disposable pet diaper 34 according to the 25th embodiment is different from the disposable pet diaper 10 of the first embodiment in that a leg stretchable elastic member is not provided, and a leakproof sheet stretchable elastic member 601 is arranged to extend from the abdomen-side end to the back-side end of the disposable pet diaper 34. The abdomen-side fixing part and the back-side fixing part are formed in the abdomen-side end and the back-side end of the disposable pet diaper 34, respectively, in the fixed part of the leakproof sheet. The leakproof sheet stretchable elastic member 601 is overlapped with the abdomen-side waist stretchable elastic member and the back-side waist stretchable elastic member of the waist stretchable elastic member.

A comparison is made between the disposable pet diaper 10 of the first embodiment and the disposable pet diaper 34 of the 25th embodiment. In the disposable pet diaper 34 of the 25th embodiment, the erected section 700 including the abdomen-side erected section 710 and the back-side erected section 720, the leakproof wall 820, the leakproof gathers 840, the third curved part 640 and the fourth curved part 420 are formed by the action of the leakproof sheet stretchable elastic member 601.

The first abdomen-side curved part 541 and the first back-side curved part 542 are formed by the action of the waist stretchable elastic member, or by the actions of the abdomen-side waist stretchable elastic member and the back-side waist stretchable elastic member, respectively.

The first contraction force intersecting region 181 is formed by the contraction force of the leakproof sheet stretchable elastic member 601 and the contraction force of the abdomen-side waist stretchable elastic member. As a result, the second abdomen-side curved part 184 is formed.

Further, the second contraction force intersecting region 182 is formed by the contraction force of the leakproof sheet stretchable elastic member 601 and the contraction force of the back-side waist stretchable elastic member. As a result, the second back-side curved part 185 is formed.

Specifically, in the disposable pet diaper 34 of the 25th embodiment, unlike in the disposable pet diaper 10 of the first embodiment, the crotch-side erected section 730 and the leg gathers 410 are not formed.

Therefore, the disposable pet diaper 34 of the 25th embodiment has all of the effects of the disposable pet diaper 10 of the first embodiment other than those exhibited by the leg gathers 410 and the crotch-side erected section 730.

Furthermore, in the disposable pet diaper 34 of the 25th embodiment, due to the absence of a leg stretchable elastic member, the ends of the disposable pet diaper 34 in the transverse direction can be located closer to the absorbent core. As a result, a portion of the disposable pet diaper 34 which comes in contact with the pet's legs can be further reduced.

Further, due to the absence of a sheet forming a portion around legs, the disposable pet diaper can be made neat around legs when worn.

26th Embodiment

Figure 47:
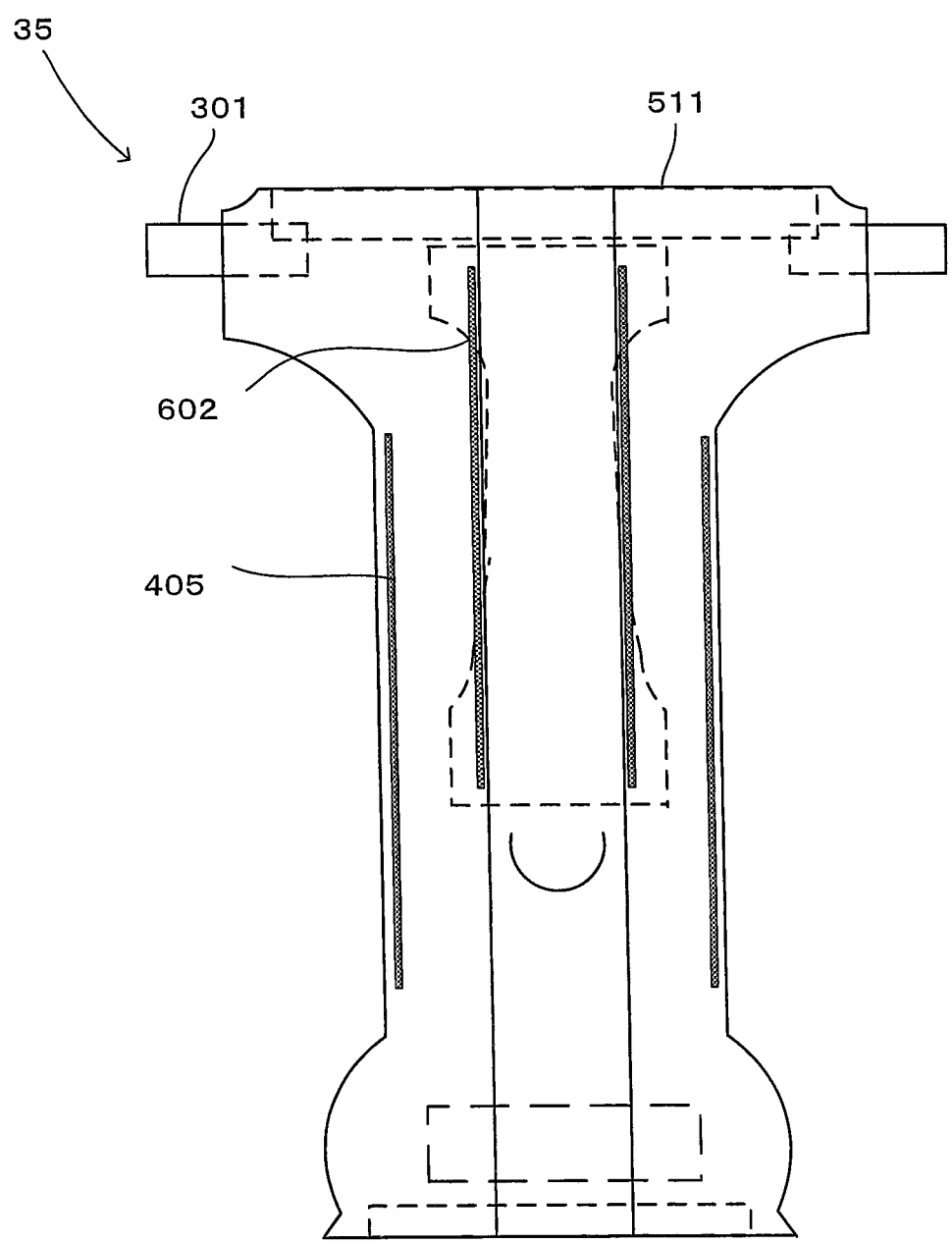
FIG. 47 is a plan view showing a disposable diaper for pets according to a 26th embodiment of the present invention, in its unfolded state.

The 26th embodiment of the present invention is explained with reference to FIG. 47. A disposable pet diaper 35 according to the 26th embodiment is different from the disposable pet diaper 10 of the first embodiment in that a leg stretchable elastic member 405 is not provided in the abdomen-side waist area and the back-side waist area. Further, the contraction force of the leakproof sheet stretchable elastic member exerts no influence on the abdomen-side end of the disposable pet diaper 35. Further, an abdomen-side waist stretchable elastic member 511 is overlapped with fastening parts 301. The feature that "an abdomen-side waist stretchable elastic member is overlapped with fastening parts" according to this invention does not mean that the abdomen-side waist stretchable elastic member is in direct contact with the fastening parts. Specifically, it means that the contraction force of the abdomen-side waist stretchable elastic member does not act on the fastening parts via flaps, but it directly act on them.

A comparison is made between the disposable pet diaper 10 of the first embodiment and the disposable pet diaper 35 of the 26th embodiment. In the disposable pet diaper 35 of the 26th embodiment, the leg gathers 410 are formed only in a region of a leg stretchable elastic member 405. Further, the abdomen-side erected section 710 and the back-side erected section 720 of the erected section 700 are not formed. The second abdomen-side curved part 184 and the second back-side curved part 185 of the second curved part 183 are not formed. The fourth curved part 420 is formed only in the region of the leg stretchable elastic member 405.

In this structure, the erected section 700 including the crotch-side erected section 730 is formed, and the leakproof wall 820 is formed. Further, the first curved part 540 including the first abdomen-side curved part 541 and the first back-side curved part 542, the third curved part 640 and part of the fourth curved part 420 are formed. Part of the leg gathers 410 and the leakproof gathers 840 are formed.

Therefore, the disposable pet diaper 35 according to the 26th embodiment has those of the effects of the disposable pet diaper 10 of the first embodiment which are exhibited by the crotch-side erected section 730, the leakproof wall 820, the first abdomen-side curved part 541 and the first back-side curved part 542, the third curved part 640, part of the fourth curved part 420, part of the leg gathers 410 and the leakproof gathers 840.

Furthermore, by provision of the abdomen-side waist stretchable elastic member 511 overlapped with the fastening parts 301, when the abdomen-side waist area is set on the abdomen of the pet in order to put the disposable pet diaper 35 on the pet, the fastening parts 301 are curved inside the disposable pet diaper under the influence of the contraction force of the abdomen-side waist stretchable elastic member 511. Thus, it is made easier for the user to grab the fastening parts 301.

27th Embodiment

Figure 48:
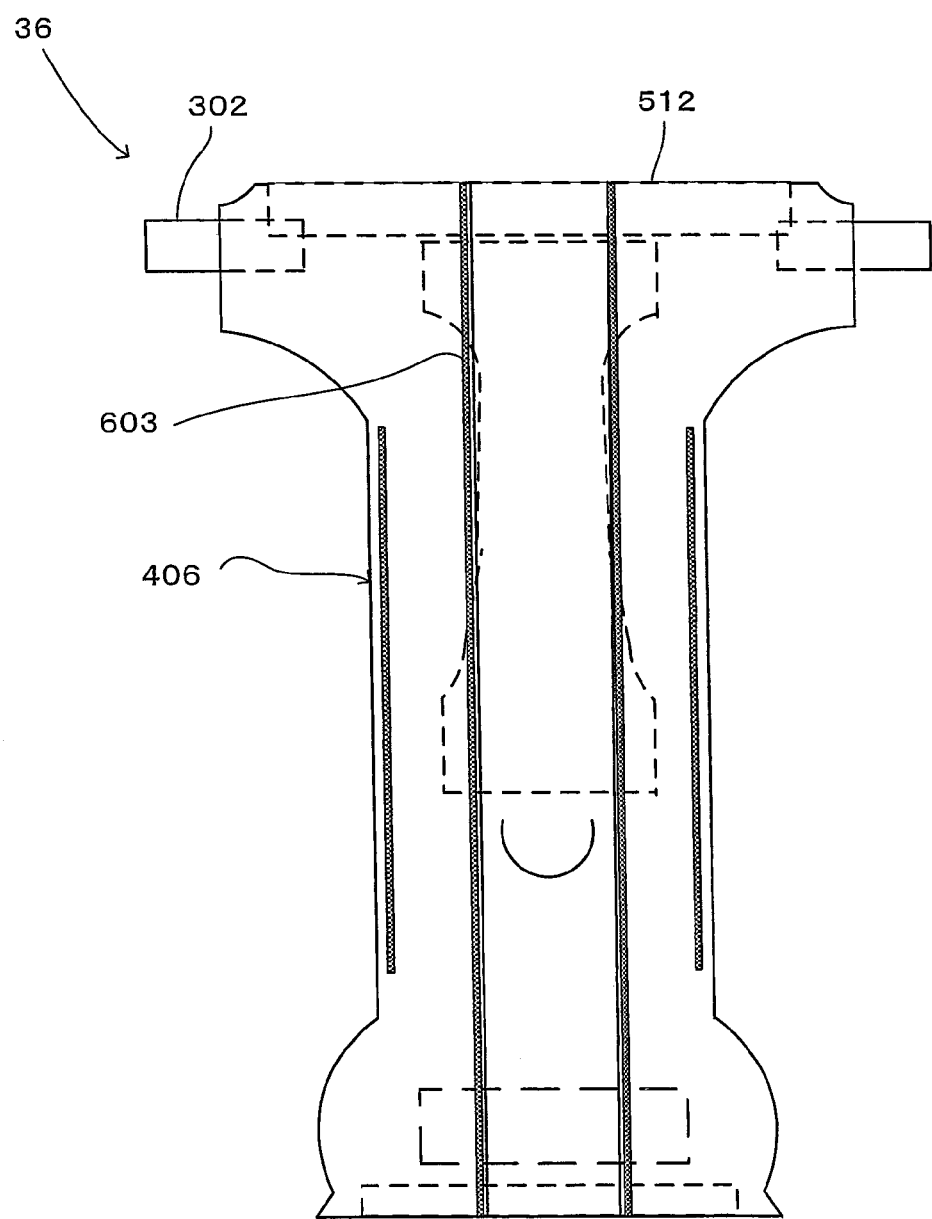
FIG. 48 is a plan view showing a disposable diaper for pets according to a 27th embodiment of the present invention, in its unfolded state.

The 27th embodiment of the present invention is explained with reference to FIG. 48. A disposable pet diaper 36 according to the 27th embodiment is different from the disposable pet diaper 10 of the first embodiment in that a leg stretchable elastic member 406 is not provided in the abdomen-side waist area and the back-side waist area of the disposable pet diaper 36, and a leakproof sheet stretchable elastic member 603 is arranged to extend from the abdomen-side end to the back-side end of the disposable pet diaper 36. The abdomen-side fixing part and the back-side fixing part are formed in the abdomen-side end and the back-side end of the disposable pet diaper 36, respectively, in the fixed part of the leakproof sheet. The leakproof sheet stretchable elastic member 603 is overlapped with an abdomen-side waist stretchable elastic member 512 and the back-side waist stretchable elastic member of the waist stretchable elastic member. The abdomen-side waist stretchable elastic member 512 is overlapped with the fastening parts 302.

A comparison is made between the disposable pet diaper 10 of the first embodiment and the disposable pet diaper 36 of the 27th embodiment. In the disposable pet diaper 36 of the 27th embodiment, the erected section 700 including the abdomen-side erected section 710 and the back-side erected section 720, the leakproof wall 820, the leakproof gathers 840, the third curved part 640 and the fourth curved part 420 are formed by the action of the leakproof sheet stretchable elastic member 603.

The first abdomen-side curved part 541 and the first back-side curved part 542 are formed by the action of the waist stretchable elastic member, or by the actions of the abdomen-side waist stretchable elastic member 512 and the back-side waist stretchable elastic member, respectively.

The first contraction force intersecting region 181 is formed by the contraction force of the leakproof sheet stretchable elastic member 603 and the contraction force of the abdomen-side waist stretchable elastic member. As a result, the second abdomen-side curved part 184 is formed.

Further, the second contraction force intersecting region 182 is formed by the contraction force of the leakproof sheet stretchable elastic member 603 and the contraction force of the back-side waist stretchable elastic member. As a result, the second back-side curved part 185 is formed.

Specifically, in the disposable pet diaper 36 of the 27th embodiment, unlike in the disposable pet diaper 10 of the first embodiment, the crotch-side erected section 730 and part of the leg gathers 410 are not formed.

Therefore, the disposable pet diaper 36 of the 27th embodiment has all of the effects of the disposable pet diaper 10 of the first embodiment other than those exhibited by the whole leg gathers 410 and the crotch-side erected section 730.

Furthermore, due to the absence of the leg stretchable elastic member in the abdomen-side region and the back-side region, the abdomen-side region and the back-side region can be fitted around the waist of the pet while the fastening member is engaged.

Further, a pocket can be formed in both end regions of the absorbent core in the diaper longitudinal direction.

Furthermore, by provision of the abdomen-side waist stretchable elastic member 512 overlapped with the fastening parts 302, when the abdomen-side waist area is set on the abdomen of the pet in order to put the disposable pet diaper 36 on the pet, the fastening parts 302 are curved inside the disposable pet diaper under the influence of the contraction force of the abdomen-side waist stretchable elastic member 512. Thus, it is made easier for the user to grab the fastening parts 302.

28th Embodiment

Figure 49:
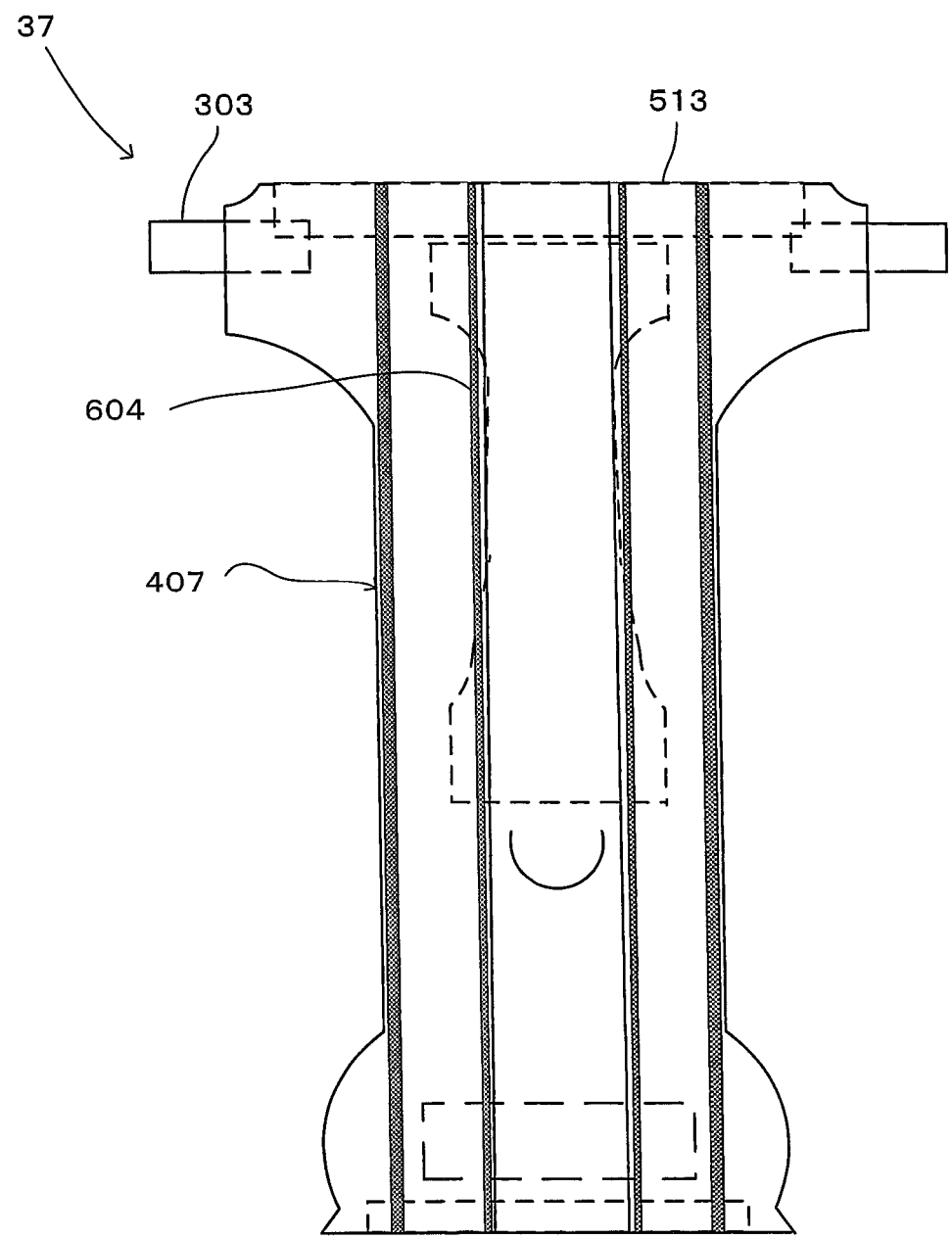
FIG. 49 is a plan view showing a disposable diaper for pets according to a 28th embodiment of the present invention, in its unfolded state.

The 28th embodiment of the present invention is explained with reference to FIG. 49. A disposable pet diaper 37 according to the 28th embodiment is different from the disposable pet diaper 10 of the first embodiment in that a leakproof sheet stretchable elastic member 604 is arranged to extend from the abdomen-side end to the back-side end of the disposable pet diaper 37. The abdomen-side fixing part and the back-side fixing part are formed in the abdomen-side end and the back-side end of the disposable pet diaper 37, respectively, in the fixed part of the leakproof sheet. The leakproof sheet stretchable elastic member 604 is overlapped with an abdomen-side waist stretchable elastic member 513 and the back-side waist stretchable elastic member of the waist stretchable elastic member. Further, the abdomen-side waist stretchable elastic member 513 is overlapped with fastening parts 303.

A comparison is made between the disposable pet diaper 10 of the first embodiment and the disposable pet diaper 37 of the 28th embodiment. In the disposable pet diaper 37 of the 28th embodiment, the erected section 700 including the abdomen-side erected section 710 and the back-side erected section 720, the leg gathers 410, the leakproof wall 820, the leakproof gathers 840, the third curved part 640 and the fourth curved part 420 are formed by the actions of a leg stretchable elastic member 407 and the leakproof sheet stretchable elastic member 604.

The first abdomen-side curved part 541 and the first back-side curved part 542 are formed by the action of the waist stretchable elastic member, or by the actions of the abdomen-side waist stretchable elastic member 513 and the back-side waist stretchable elastic member, respectively.

Two structures of the first contraction force intersecting regions 181 are formed. One is formed by intersection of the contraction forces of the leg stretchable elastic member 407 and the abdomen-side waist stretchable elastic member 513, and the other is formed by the contraction force of the leakproof sheet stretchable elastic member 604 and the contraction force of the abdomen-side waist stretchable elastic member 513. Accordingly, two structures of the second abdomen-side curved parts 184 are formed by formation of the two structures of the first contraction force intersecting regions 181.

Similarly, two structures of the second contraction force intersecting regions 182 are formed. One is formed by intersection of the contraction forces of the leg stretchable elastic member 407 and the back-side waist stretchable elastic member, and the other is formed by the contraction force of the leakproof sheet stretchable elastic member 604 and the contraction force of the back-side waist stretchable elastic member. Accordingly, two structures of the second back-side curved parts 185 are formed by formation of the two structures of the second contraction force intersecting regions 182.

Specifically, unlike in the disposable pet diaper 10 of the first embodiment, the crotch-side erected section 730 is not formed in the disposable pet diaper 37 of the 28th embodiment.

Therefore, the disposable pet diaper 37 of the 28th embodiment has all of the effects of the disposable pet diaper 10 of the first embodiment other than those exhibited by the crotch-side erected section 730.

Furthermore, by provision of the abdomen-side waist stretchable elastic member 513 overlapped with the fastening parts 303, when the abdomen-side waist area is set on the abdomen of the pet in order to put the disposable pet diaper 37 on the pet, the fastening parts 303 are curved inside the disposable pet diaper under the influence of the contraction force of the abdomen-side waist stretchable elastic member 513. Thus, it is made easier for the user to grab the fastening parts 303.

Further, the contraction forces act over the whole diaper in the diaper longitudinal direction, so that leakage of excrement can be prevented. Therefore, this disposable pet diaper is particularly suitable for bedridden pets.

29th Embodiment

Figure 50:
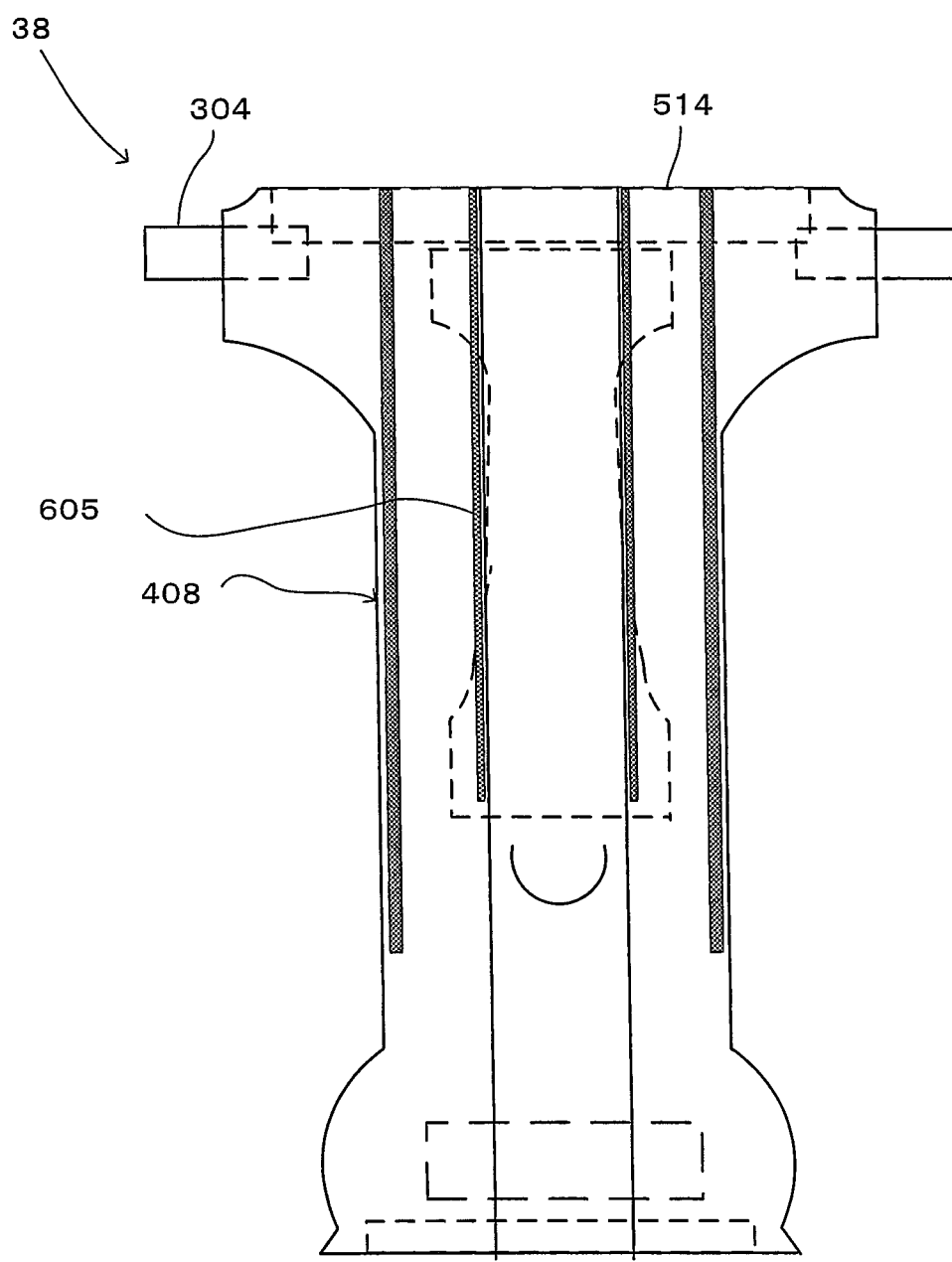
FIG. 50 is a plan view showing a disposable diaper for pets according to a 29th embodiment of the present invention, in its unfolded state.
Figure 51:
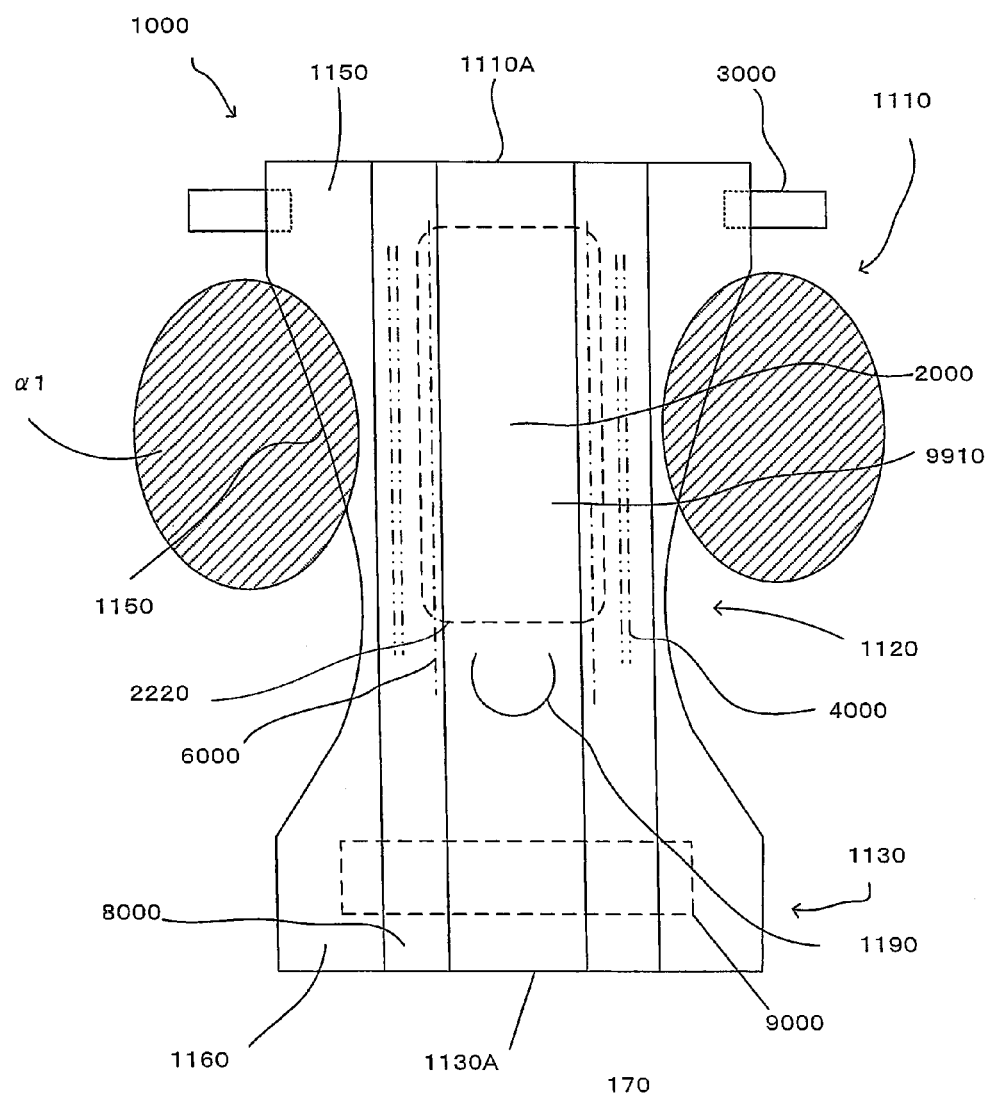
FIG. 51 is a plan view showing a prior art disposable diaper for pets in its unfolded state.
Figure 52:
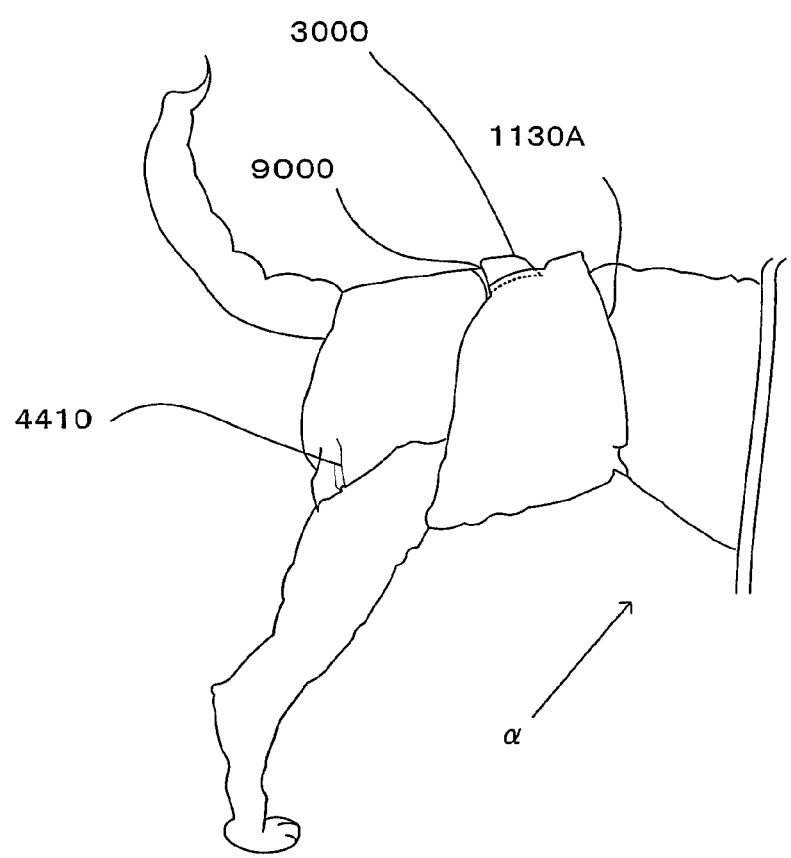
FIG. 52 is an explanatory drawing for illustrating a state of the prior art disposable diaper worn by a pet.

The 29th embodiment of the present invention is explained with reference to FIG. 50. A disposable pet diaper 38 according to the 29th embodiment is different from the disposable pet diaper 10 of the first embodiment in that a leg stretchable elastic member 408 is not provided in the back-side waist area. Further, a leakproof sheet stretchable elastic member 605 is arranged to extend up to the abdomen-side end of the disposable pet diaper 38. The abdomen-side fixing part is formed in the abdomen-side end of the disposable pet diaper 38 in the fixed part of the leakproof sheet. The leakproof sheet stretchable elastic member 605 is overlapped with an abdomen-side waist stretchable elastic member 514 of the waist stretchable elastic member. Further, the abdomen-side waist stretchable elastic member 514 is overlapped with fastening parts 304.

A comparison is made between the disposable pet diaper 10 of the first embodiment and the disposable pet diaper 38 of the 29th embodiment. In the disposable pet diaper 38 of the 29th embodiment, the erected section 700 including the abdomen-side erected section 710 and the crotch-side erected section 730, part of the leg gathers 410, the leakproof wall 820, the leakproof gathers 840, the third curved part 640 and part of the fourth curved part 420 are formed by the actions of the leg stretchable elastic member 408 and the leakproof sheet stretchable elastic member 605.

The first abdomen-side curved part 541 is formed by the action of the waist stretchable elastic member or the abdomen-side waist stretchable elastic member 514.

Two structures of the first contraction force intersecting regions 181 are formed. One is formed by intersection of the contraction forces of the leg stretchable elastic member 408 and the abdomen-side waist stretchable elastic member 514, and the other is formed by the contraction force of the leakproof sheet stretchable elastic member 605 and the contraction force of the abdomen-side waist stretchable elastic member 514. Accordingly, two structures of the second abdomen-side curved parts 184 are formed by formation of the two structures of the first contraction force intersecting regions 181.

Specifically, unlike in the disposable pet diaper 10 of the first embodiment, the back-side erected section 720, part of the leg gathers 410, the first back-side curved part 542, the second back-side curved part 185 and part of the fourth curved part 420 are not formed in the disposable pet diaper 38 of the 29th embodiment.

Therefore, the disposable pet diaper 38 of the 29th embodiment has all of the effects of the disposable pet diaper 10 of the first embodiment other than those exhibited by the back-side erected section 720, the whole leg gathers 410, the first back-side curved part 542, the second back-side curved part 185 and the whole fourth curved part 420.

In this structure, the contraction forces strongly act only on the abdomen-side region, so that a pocket can be readily formed in an abdomen-side region of the absorbent core. Therefore, this disposable pet diaper is suitable as a disposable diaper for male pets.

Furthermore, by provision of the abdomen-side waist stretchable elastic member 514 overlapped with the fastening parts 304, when the abdomen-side waist area is set on the abdomen of the pet in order to put the disposable pet diaper 38 on the pet, the fastening parts 304 are curved inside the disposable pet diaper under the influence of the contraction force of the abdomen-side waist stretchable elastic member 514. Thus, it is made easier for the user to grab the fastening parts 304.

The structures or features of the disposable pet diaper according to this invention are not limited to those described above. The structures or features of the first to 29th embodiments can be appropriately used in combination.

(Correspondences Between the Features of the Embodiments and the Features of the Invention)

The disposable pet diaper 10, 11, 12, 13, 14, 15, 16, 17, 18, 19, 20, 21, 22, 23, 24, 25, 26, 27, 28, 29, 30, 31, 32, 33, 34, 35, 36, 37, 38 is an example embodiment that corresponds to the "disposable diaper for pets" according to this invention. The back-side waist area 130 is an example embodiment that corresponds to the "back-side waist area" according to this invention. The abdomen-side waist area 110 is an example embodiment that corresponds to the "abdomen-side waist area" according to this invention. The crotch area 120 is an example embodiment that corresponds to the "crotch area" according to this invention. The diaper longitudinal direction Y and the diaper transverse direction X are example embodiments that correspond to the "diaper longitudinal direction" and the "diaper transverse direction", respectively, according to this invention. The end 130A of the back-side waist area is an example embodiment that corresponds to the "back-side waist area end" according to this invention. The end 110A of the abdomen-side waist area is an example embodiment that corresponds to the "abdomen-side waist area end" according to this invention. The ends 100A in the diaper transverse direction are an example embodiment that corresponds to the "ends" according to this invention. The back-side flap 160, 161, 162, 163, 164 is an example embodiment that corresponds to the "back-side flap" according to this invention. The abdomen-side flap 150 is an example embodiment that corresponds to the "abdomen-side flap" according to this invention. The tail insertion opening 190 is an example embodiment that corresponds to the "tail insertion opening" according to this invention. The absorbent core 200 is an example embodiment that corresponds to the "absorbent core" according to this invention. The fastening part 300, 301, 302, 303, 304 is an example embodiment that corresponds to the "fastening part" according to this invention. The fastening region 900, 901, 902, 903, 904, 905, 906, 907 is an example embodiment that corresponds to the "fastening region" according to this invention. The identification region 10A, 11A, 12A, 13A, 14A, 15A, 16A is an example embodiment that corresponds to the "identification region" according to this invention. The first extended identification region 10A1 is an example embodiment that corresponds to the "first extended identification region" according to this invention. The second extended identification region 11A1 is an example embodiment that corresponds to the "second extended identification region" according to this invention. The colored identification region 12A1 is an example embodiment that corresponds to the "colored identification region" according to this invention. The first virtual line 10A11, the second virtual line 900BC1, the third virtual line D160, the fourth virtual line 300C1, the fifth virtual line 150A1 and the sixth virtual line D150 are example embodiments that correspond to the "first virtual line", the "second virtual line", the "third virtual line", the "fourth virtual line", the "fifth virtual line" and the "sixth virtual line", respectively, according to this invention. The visible region 13A1, 14A1, 15A1, 16A1 is an example embodiment that corresponds to the "visible region" according to this invention. The light transmissive identification region 13A2 is an example embodiment that corresponds to the "light transmissive identification region" according to this invention. The cutout identification region 14A2 is an example embodiment that corresponds to the "cutout identification region" according to this invention. The first open identification region 15A2 is an example embodiment that corresponds to the "first open identification region" according to this invention. The second open identification region 16A2 is an example embodiment that corresponds to the "second open identification region" according to this invention. The cover region 16A22 is an example embodiment that corresponds to the "cover region" according to this invention.

In view of the nature of the above-described invention, various features can be provided as follows.

(Aspect 1)

A disposable diaper for pets, comprising:

a back-side waist area, an abdomen-side waist area, and a crotch area between the back-side waist area and the abdomen-side waist area, a diaper longitudinal direction in which the back-side waist area, the crotch area and the abdomen-side waist area contiguously extend when the disposable diaper is not worn by a pet, and a diaper transverse direction crossing the diaper longitudinal direction, a back-side waist area end in the diaper longitudinal direction, an abdomen-side waist area end in the diaper longitudinal direction, and both ends in the diaper transverse direction, a back-side flap formed in the back-side waist area, an abdomen-side flap formed in the abdomen-side waist area, a tail insertion opening formed in a prescribed region in the diaper longitudinal direction, an absorbent core formed on one side of the tail insertion opening in the diaper longitudinal direction and disposed in a prescribed region extending over the crotch area and the abdomen-side waist area, a fastening part having a prescribed length and provided in the abdomen-side flap, and a fastening region provided in the back-side waist area and configured to receive the fastening part, wherein:

at least one of the back-side flap and the abdomen-side flap has an identification region;

when the disposable diaper is put on the pet, the crotch area and the abdomen-side waist area cover a crotch and an abdomen of the pet, while the back-side waist area is closely fitted to a back of the pet, and the fastening part is fastened to the fastening region, and while the disposable diaper is worn by the pet, the weight of the absorbent core after excretion is received in the longitudinal direction of the fastening part, and the identification region is configured such that an abnormality of the back-side flap can be identified based on visual information of the identification region from outside the disposable diaper.

(Aspect 2)

The disposable diaper as defined in aspect 1, wherein the back-side flap is determined to be in a normal state if the identification region is visible from outside the disposable diaper, while the back-side flap is determined to be in an abnormal state if the identification region is not visible from outside the disposable diaper.

(Aspect 3)

The disposable diaper as defined in aspect 1 or 2, wherein the normal state of the back-side flap refers to a state that the back-side flap is not creased when the disposable diaper is worn by the pet, while the abnormal state of the back-side flap refers to a state that at least part of the back-side flap is creased when the disposable diaper is worn by the pet (Aspect 4)

The disposable diaper as defined in any one of aspects 1 to 3, wherein the identification region is formed in the back-side flap.

(Aspect 5)

The disposable diaper as defined in aspect 4, wherein the identification region comprises a first extended identification region extended in a transverse direction from the back-side flap.

(Aspect 6)

The disposable diaper as defined in aspect 4, wherein the identification region comprises a second extended identification region extended in a longitudinal direction from the back-side flap.

(Aspect 7)

The disposable diaper as defined in aspect 4, wherein the identification region comprises a colored identification region that is differently colored from the other region of the back-side flap.

(Aspect 8)

The disposable diaper as defined in aspect 4, wherein the identification region in the back-side flap protrudes from an end of the abdomen-side flap in the longitudinal direction when the disposable diaper is worn by the pet (Aspect 9)

The disposable diaper as defined in aspect 8, comprising:

a first virtual line extending in the diaper transverse direction from a back-side end of the identification region in the back-side flap, a second virtual line extending in the diaper transverse direction from a back-side end of the fastening region in the back-side flap, a third virtual line connecting the first virtual line and the second virtual line and extending in the diaper longitudinal direction, a fourth virtual line extending in the diaper transverse direction from a back-side end of the fastening part in the abdomen-side flap, a fifth virtual line extending in the diaper transverse direction from an abdomen-side end of the abdomen-side flap, and a sixth virtual line connecting the fourth virtual line and the fifth virtual line and extending in the diaper longitudinal direction, wherein:

the third virtual line is longer than the sixth virtual line.

(Aspect 10)

The disposable diaper as defined in any one of aspects 1 to 3, wherein the identification region is formed in the abdomen-side flap.

(Aspect 11)

The disposable diaper as defined in aspect 10, wherein the identification region comprises a visible region that is formed in the abdomen-side flap for checking the state of the back-side flap.

(Aspect 12)

The disposable diaper as defined in aspect 10, wherein the visible region comprises a light transmissive identification region which is capable of transmitting light.

(Aspect 13)

The disposable diaper as defined in aspect 10, wherein the visible region comprises a cutout identification region formed by cutting out an abdomen-side end portion of the abdomen-side flap.

(Aspect 14)

The disposable diaper as defined in aspect 10, wherein the visible region comprises a first open identification region formed by an opening in the abdomen-side flap.

(Aspect 15)

The disposable diaper as defined in aspect 10, wherein the visible region comprises a second open identification region formed by an opening in the abdomen-side flap, and a cover region configured to cover the second open identification region and to be freely opened and closed with respect to the second open identification region.

(Aspect 16)

The disposable diaper as defined in any one of aspects 1 to 15, wherein the identification region comprises a back-side flap identification region formed in the back-side flap and an abdomen-side flap identification region formed in the abdomen-side flap.

DESCRIPTION OF THE NUMERALS 10, 11, 12, 13, 14, 15, 16, 17, 18, 19, 20, 21, 22, 23, 24, 25, 26, 27, 28, 29, 30, 31, 32, 33, 34, 35, 36, 37, 38, 1000 disposable pet diaper
10A, 11A, 12A, 13A, 14A, 15A, 16A identification region
10A1 first extended identification region
10A11 first virtual line
11A1 second extended identification region
12A1 colored identification region
13A1, 14A1, 15A1, 16A1 visible region
13A2 light transmissive identification region
14A2 cutout identification region
15A2 first open identification region
16A2 second open identification region
16A22 cover region
100A end in the diaper transverse direction
100AP diaper minimum width point
100P diaper center point
100Y1 flap boundary line
100Y2 diaper longitudinal center line
100Z1 inside surface
100Z2 outside surface
110, 1110 abdomen-side waist area
110A, 1110A abdomen-side end
110AP abdomen-side end center point
120, 1120 crotch area
120A leg-side end
130, 1130 back-side waist area
130A, 1130A back-side end
130AP back-side end center point
140A flap
140B body
150, 1150 abdomen-side flap
150A end in the diaper longitudinal direction
150A1 fifth virtual line
150B end in the diaper transverse direction
150C, 1150B back-side end
150L length of the abdomen-side flap in the diaper transverse direction
160, 161, 162, 163, 164, 1160 back-side flap
160B, 161B, 162B, 163B end of the back-side flap in the transverse direction
160B1, 161B1, 162B1, 163B1 maximum width region
160L length of the back-side flap in the diaper transverse direction
170 absorbent-core non-arrangement region
171 abdomen-side erected region
172 back-side erected region
173 crotch-side erected region
180 contraction force intersecting region
181 first contraction force intersecting region
182 second contraction force intersecting region
183 second curved part
184 second abdomen-side curved part
185 second back-side curved part
190, 1190 tail insertion opening
191 cut
200, 2000 absorbent core
210 abdomen-side end
220 back-side end
230 end in the diaper transverse direction
300, 301, 302, 303, 304, 3000 fastening part
300C1 fourth virtual line
310 free part
320 fixed part
300P1 fastening part midpoint
300P2 shortest line point
300L shortest straight-line distance
300X fastening part longitudinal direction
300Y fastening part transverse direction
400, 401, 401A, 401B, 401C, 402, 402A, 402B, 403, 404, 405, 406, 407, 408, 4000 leg stretchable elastic member
410, 4410 leg gather
420 fourth curved part
500 waist stretchable elastic member
510, 511, 512, 513, 514 abdomen-side waist stretchable elastic member
520 back-side waist stretchable elastic member
530 waist gather
540 first curved part
541 first abdomen-side curved part
542 first back-side curved part
600, 601, 602, 603, 604, 605, 6000 leakproof sheet stretchable elastic member
610 contraction force fixing part
620 abdomen-side contraction force fixing part
630 back-side contraction force fixing part
640 third curved part
700 erected section
710 abdomen-side erected section
720 back-side erected section
730 crotch-side erected section
740 erection sheet
800, 8000 leakproof sheet
810 folded part
820 leakproof wall
830 leakproof sheet fixed part
840 leakproof gather
850 excrement storage space
900, 901, 902, 903, 904, 905, 906, 907, 9000 fastening region
900A, 901A, 902A, 903A, 904A, 905A, 906A, 907A first fastening region
900B, 901B, 902B second fastening region
900BC1 second virtual line
910 liquid-permeable sheet
920 liquid-resistant sheet
930 outer sheet
930A, 931A, 932A, 933A, 934A first welded part
930AA first welded part group
930AB, 931AB, 932AB first adjacent welded part group
930A1, 931A1 first welded continuous line
932A2, 933A2, 934A2 first welded short line
930B, 931B, 932B, 933B, 934B second welded part
930BA second welded part group
930BB, 931BB, 932BB second adjacent welded part group
930B1, 931B1 second welded continuous line
932B2, 933B2, 934B2 second welded short line
930C, 931C, 932C, 933C, 934C third welded part
930CA third welded part group
930CB, 931CB third adjacent welded part group
930C1 third welded continuous line
931C2, 932C2, 933C2, 934C2 third welded short line 930D, 931D, 932D, 933D, 934D surrounding part
930D1, 930D2 first diagonal line
930L1, 931L1 first loop part
930L2, 931L2 second loop part
931L3 third loop part
931L4 fourth loop part
931L5 fifth loop part
D1 diaper longitudinal length
D2 measured length
D150 sixth virtual line
D160 third virtual line
F1 contraction force of the leg stretchable elastic member
F2 contraction force of the waist stretchable elastic member
F3 contraction force acting on the contraction force intersecting region
X diaper transverse direction
Y diaper longitudinal direction
α pet
α1 leg of pet
α2 back of pet
α3 abdomen of pet

The invention claimed is:

1. A disposable diaper for pets, said disposable diaper comprising:
    a back-side waist area, an abdomen-side waist area, and a crotch area between the back-side waist area and the abdomen-side waist area,
    a diaper longitudinal direction in which the back-side waist area, the crotch area and the abdomen-side waist area contiguously extend when the disposable diaper is not worn on a pet, and a diaper transverse direction crossing the diaper longitudinal direction,
    a back-side waist area end and an abdomen-side waist area end opposing each other in the diaper longitudinal direction,
    two transverse ends opposing each other in the diaper transverse direction,
    a back-side flap formed in the back-side waist area,
    an abdomen-side flap formed in the abdomen-side waist area,
    a tail insertion opening formed in a prescribed region in the diaper longitudinal direction,
    an absorbent core formed on one side of the tail insertion opening in the diaper longitudinal direction and extending over the crotch area and the abdomen-side waist area,
    a fastening part having a prescribed length and provided in the abdomen-side flap, and
    a fastening region provided in the back-side waist area and configured to receive the fastening part,
    wherein
    at least one of the back-side flap and the abdomen-side flap has an identification region;
    when the disposable diaper is worn on the pet,
        the crotch area and the abdomen-side waist area are adapted to cover a crotch and an abdomen of the pet, respectively,
        the back-side waist area is adapted to be fitted to a back of the pet, and
        the fastening part is fastened to the fastening region,
        the weight of the absorbent core after excretion is received in a fastening part longitudinal direction of the fastening part, and
        the identification region is configured to cause an abnormality of the back-side flap to be visually identifiable based on visual information of the identification region from outside the disposable diaper, and
    a width of the back-side flap in the diaper transverse direction is increased and decreased to form an arc curved shape of the back-side flap, and then further increased to form the identification region in the back-side flap.

2. The disposable diaper as defined in claim 1, wherein
    the identification region being visible from outside the disposable diaper indicates that the back-side flap is in a normal state, and
    the identification region are not visible from outside the disposable diaper indicates that the back-side flap is in an abnormal state.

3. The disposable diaper as defined in claim 2, wherein
    the normal state of the back-side flap corresponds to a state in which the back-side flap is not creased when the disposable diaper is worn on the pet, and
    the abnormal state of the back-side flap corresponds to a state in which at least part of the back-side flap is creased when the disposable diaper is worn on the pet.

4. The disposable diaper as defined in claim 1, wherein the identification region comprises an extended identification region elongated in the diaper transverse direction in the back-side flap.

5. The disposable diaper as defined in claim 1, wherein the identification region comprises an extended identification region elongated in the diaper longitudinal direction in the back-side flap.

6. The disposable diaper as defined in claim 1, wherein the identification region comprises a colored identification region that is differently colored from the other region of the back-side flap.

7. The disposable diaper as defined in claim 1, wherein the identification region in the back-side flap protrudes from an end of the abdomen-side flap in the diaper longitudinal direction when the disposable diaper is worn on the pet.

8. The disposable diaper as defined in claim 7, further comprising:
    a first virtual line extending in the diaper transverse direction from a back-side end of the identification region in the back-side flap,
    a second virtual line extending in the diaper transverse direction from a back-side end of the fastening region in the back-side flap,
    a third virtual line connecting the first virtual line and the second virtual line and extending in the diaper longitudinal direction,
    a fourth virtual line extending in the diaper transverse direction from a back-side end of the fastening part in the abdomen-side flap,
    a fifth virtual line extending in the diaper transverse direction from an abdomen-side end of the abdomen-side flap, and
    a sixth virtual line connecting the fourth virtual line and the fifth virtual line and extending in the diaper longitudinal direction,
    wherein
    the third virtual line is longer than the sixth virtual line.

9. The disposable diaper as defined in claim 1, wherein the abdomen-side flap includes a further identification region.

10. The disposable diaper as defined in claim 9, wherein the further identification region in the abdomen-side flap comprises a visible region configured to indicate the abnormality of the back-side flap.

11. The disposable diaper as defined in claim 10, wherein the visible region comprises a light transmissive identification region which is light transmittable.

12. The disposable diaper as defined in claim 10, wherein the visible region comprises a cutout identification region in an abdomen-side end portion of the abdomen-side flap.

13. The disposable diaper as defined in claim 10, wherein the visible region comprises an open identification region including an opening in the abdomen-side flap.

14. The disposable diaper as defined in claim 10, wherein the visible region comprises
- an open identification region including an opening in the abdomen-side flap, and
- a cover region configured to cover the open identification region and to be freely opened and closed with respect to the open identification region.

15. The disposable diaper as defined in claim 1, further comprising:
- an abdomen-side waist stretchable elastic member in the abdomen-side waist area,
- a back-side waist stretchable elastic member in the back-side waist area, and
- a leg sheet stretchable elastic member extending in the diaper longitudinal direction between the absorbent core and each of the two transverse ends, and configured to form leg gathers,
- wherein the leg sheet stretchable elastic member overlap the abdomen-side waist stretchable elastic member or the back-side waist stretchable elastic member in a diaper thickness direction crossing the diaper longitudinal direction and the diaper transverse direction.

16. The disposable diaper as defined in claim 15, further comprising:
- a leakproof sheet adapted to face toward the pet when the disposable pet diaper is worn on the pet; and
- a leakproof sheet stretchable elastic member disposed in a folded end of the leakproof sheet,
wherein
a length of the leg stretchable elastic member in the diaper longitudinal direction is greater than a length of the leakproof sheet stretchable elastic member in the diaper longitudinal direction.

* * * * *